United States Patent
Kawabata et al.

(10) Patent No.: US 8,962,233 B2
(45) Date of Patent: Feb. 24, 2015

(54) ACTINIC-RAY—OR RADIATION-SENSITIVE RESIN COMPOSITION AND METHOD OF FORMING PATTERN USING THE COMPOSITION

(75) Inventors: Takeshi Kawabata, Haibara-gun (JP); Tomotaka Tsuchimura, Haibara-gun (JP); Takayuki Ito, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 250 days.

(21) Appl. No.: 13/015,874

(22) Filed: Jan. 28, 2011

(65) Prior Publication Data

US 2011/0189609 A1    Aug. 4, 2011

(30) Foreign Application Priority Data

Jan. 29, 2010    (JP) ................. 2010-019284

(51) Int. Cl.
| | | |
|---|---|---|
| G03F 7/004 | (2006.01) | |
| G03F 7/039 | (2006.01) | |
| G03F 7/038 | (2006.01) | |
| G03F 7/20 | (2006.01) | |
| G03F 7/30 | (2006.01) | |

(52) U.S. Cl.
USPC ........ 430/270.1; 430/311; 430/325; 430/326; 430/905; 430/910; 430/919; 430/921; 430/925; 430/942; 430/966; 562/30; 562/45; 562/74; 562/79; 562/82; 562/91; 562/100; 564/82; 564/96

(58) Field of Classification Search
None
See application file for complete search history.

(56) References Cited

U.S. PATENT DOCUMENTS

| | | | |
|---|---|---|---|
| 6,548,221 B2 | 4/2003 | Uetani et al. | |
| 7,026,098 B2 | 4/2006 | Komatsu et al. | |
| 7,541,131 B2 | 6/2009 | Kawanishi | |
| 2005/0008864 A1 | 1/2005 | Ingen Schenau et al. | |
| 2005/0233245 A1 | 10/2005 | Koitabashi et al. | |
| 2007/0037091 A1 | 2/2007 | Koitabashi et al. | |
| 2008/0187860 A1 * | 8/2008 | Tsubaki et al. | ............ 430/270.1 |
| 2008/0248421 A1 * | 10/2008 | Fukuhara et al. | ............ 430/281.1 |
| 2010/0167207 A1 | 7/2010 | Tanaka et al. | |
| 2011/0076615 A1 * | 3/2011 | Kawabata et al. | ............ 430/270.1 |

FOREIGN PATENT DOCUMENTS

| | | |
|---|---|---|
| EP | 1 480 078 A1 | 11/2004 |
| JP | 11-030856 A | 2/1999 |
| JP | 2004-157158 A | 6/2004 |
| JP | 2004-158287 A | 6/2004 |
| JP | 2005-326833 A | 11/2005 |
| JP | 2006-251551 A | 9/2006 |
| JP | 2006-276760 A | 10/2006 |
| JP | 2006-350212 A | 12/2006 |
| JP | 2007-094356 A | 4/2007 |
| JP | 2007-206639 A | 8/2007 |
| JP | 2008-076559 A | 4/2008 |
| JP | 2008-162101 A | 7/2008 |
| JP | 2010-170094 A | 8/2010 |

OTHER PUBLICATIONS

JPO English abstract for JP11-30856 (Feb. 1999).*
Machine-assisted English translation of JP11-30856, provided by JPO (Feb. 1999).*
Edited by Hirai, Y., Fundamentals of nanoimprint and its technology development/application deployment—technology of nanoimprint substrate and its latest technology deployment—Science and New Technology in Nanoprint, Jun. 2006, Frontier Publishing.
Japanese Office Action dated Apr. 15, 2014 issued in application No. 2010-019284.
Japanese Office Action issued in application No. 2010-019284 dated Sep. 17, 2013.

* cited by examiner

*Primary Examiner* — Sin J. Lee
(74) *Attorney, Agent, or Firm* — Sughrue Mion, PLLC

(57) ABSTRACT

According to one embodiment, an actinic-ray- or radiation-sensitive resin composition includes an arylsulfonium salt that when exposed to actinic rays or radiation, generates an acid, the arylsulfonium salt containing at least one aryl ring on which there are a total of one or more electron donating groups, the acid generated upon exposure to actinic rays or radiation having a volume of 240 Å$^3$ or greater.

21 Claims, No Drawings

ACTINIC-RAY—OR RADIATION-SENSITIVE RESIN COMPOSITION AND METHOD OF FORMING PATTERN USING THE COMPOSITION

CROSS-REFERENCE TO RELATED APPLICATIONS

This application is based upon and claims the benefit of priority from prior Japanese Patent Application No. 2010-019284, filed Jan. 29, 2010, the entire contents of which are incorporated herein by reference.

BACKGROUND OF THE INVENTION

1. Field of the Invention

The present invention relates to an actinic-ray- or radiation-sensitive resin composition that when exposed to actinic rays or radiation, makes a reaction to thereby change its properties and a method of forming a pattern using the composition. More particularly, the present invention relates to an actinic-ray- or radiation-sensitive resin composition for use in a semiconductor production process for an IC and the like, a circuit board production for a liquid crystal, a thermal head and the like, the fabrication of an imprint mold structure, other photofabrication processes, a lithographic printing plate and an acid-hardenable composition and also relates to a method of forming a pattern with the use of the composition.

In the present invention, the terms "actinic rays" and "radiation" mean, for example, brightline spectra from a mercury lamp, far ultraviolet represented by an excimer laser, extreme ultraviolet, X-rays, soft X-rays, an electron beam and the like. In the present invention, the term "light" means actinic rays or radiation.

2. Description of the Related Art

A resist composition of chemical amplification type is a pattern forming material that is capable of, upon exposure to far ultraviolet or other radiation, generating an acid in exposed areas and, by a reaction catalyzed by the acid, changing the solubility in a developer between the areas having been exposed to actinic radiation and the nonexposed areas to thereby attain pattern formation on a substrate.

When a KrF excimer laser is used as an exposure radiation source, a resin whose fundamental skeleton is formed of a poly(hydroxystyrene) exhibiting a low absorption mainly in the region of 248 nm is employed as a major component of a resist composition. Accordingly, there can be attained a high sensitivity, high resolution and favorable pattern formation. Thus, a system superior to the conventional naphthoquinone diazide/novolak resin system is realized.

However, in using a radiation source of a further shorter wavelength, for example, an exposure radiation source of an ArF excimer laser (193 nm), as the compounds containing aromatic groups inherently exhibit a sharp absorption in the region of 193 nm, the above-mentioned chemical amplification system has not been satisfactory.

Consequently, resists for ArF excimer laser containing a resin with an alicyclic hydrocarbon structure have been developed.

It is generally known to use a triphenylsulfonium salt as a photoacid generator being a major component of any of chemical amplification resists (see, for example, patent reference 1).

In this connection, when use is made of, for example, a radiation source capable of emitting an electron beam, X-rays or EUV, the exposure is carried out in vacuum. This might cause any low-boiling-point compounds, such as solvents, and resist materials decomposed by high energy to evaporate to thereby dirty the exposure apparatus. This outgassing problem is becoming serious. In recent years, various researches have been conducted toward the reduction of the outgassing, and various improvements have been proposed for photoacid generators (see, for example, patent reference 2).

There is a demand in the art for the development of a photosensitive composition that not only can reduce outgassing but also is enhanced in sensitivity, resolution, pattern configuration, roughness characteristic, etc. through the improvement of a photoacid generator (see, for example, patent references 3 and 4).

In particular, the roughness characteristic and resolution become important in accordance with the reduction of pattern dimension. In the field of lithography using X-rays, an electron beam or EUV, as the formation of a fine pattern of several tens of nanometers is targeted, it is required to realize, in particular, excellent resolution and roughness characteristic.

Further, the microfabrication using a resist composition is not only directly used in the manufacturing of integrated circuits but also, in recent years, finds application in the fabrication of so-called imprint mold structures, etc. (see, for example, patent references 5 and 6 and non-patent reference 1). Therefore, in the use of X-rays, soft X-rays or an electron beam as an exposure radiation source as well, it is an important task to simultaneously realize high sensitivity, high resolution, favorable pattern configuration and favorable roughness characteristic, and it is now needed to resolve the task.

PRIOR ART REFERENCE

Patent Reference

Patent reference 1: U.S. Pat. No. 6,548,221,
Patent reference 2: European Patent No. 1480078,
Patent reference 3: Jpn. Pat. Appln. KOKAI Publication No. (hereinafter referred to as JP-A-) 2007-94356,
Patent reference 4: JP-A-H11-30856,
Patent reference 5: JP-A-2004-158287, and
Patent reference 6: JP-A-2008-162101.

Non-Patent Reference

[Non-patent reference 1] "Fundamentals of nanoimprint and its technology development/application deployment—technology of nanoimprint substrate and its latest technology deployment" edited by Yoshihiko Hirai, published by Frontier Publishing (issued in June, 2006).

BRIEF SUMMARY OF THE INVENTION

It is an object of the present invention to provide an actinic-ray- or radiation-sensitive resin composition exhibiting enhanced resolution, roughness characteristic, pattern configuration and outgassing performance without detriment to sensitivity. It is another object of the present invention to provide a method of forming a pattern using the composition.

The above objects are attained by employing as a photoacid generator a novel compound characterized in that an electron donating group is introduced in the sulfonium cation thereof and that the acid generated thereby exhibits a low diffusion.

Namely, the above problem can be solved by the present invention identified by the following features.

(1) An actinic-ray- or radiation-sensitive resin composition comprising an arylsulfonium salt that when exposed to actinic rays or radiation, generates an acid, the arylsulfonium salt containing at least one aryl ring on which there are a total of one or more electron donating groups, the acid generated upon exposure to actinic rays or radiation having a volume of 240 Å$^3$ or greater.

(2) The actinic-ray- or radiation-sensitive resin composition according to item (1), wherein the arylsulfonium salt contains any of cation moieties of general formula:

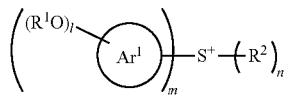
(I)

in which

Ar$^1$ represents an aromatic ring, in which a substituent other than —(OR$^1$) groups may further be introduced, R$^1$ represents a linear or branched alkyl group or a cycloalkyl group, R$^2$ represents an optionally substituted aryl group, an optionally substituted alkyl group or an optionally substituted cycloalkyl group, l is an integer of 1 or greater, and m is an integer of 1 to 3, and n an integer of 0 to 2, provided that m+n=3 is satisfied, provided that two members selected from among m Ar$^1$s and n R$^2$s may be bonded to each other to thereby form a ring in cooperation with the sulfur atom appearing in the formula.

(3) The actinic-ray- or radiation-sensitive resin composition according to item (1) or (2), wherein the arylsulfonium salt contains any of anion moieties of general formula:

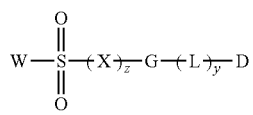
(II)

in which

X represents an optionally substituted alkylene group or an optionally substituted fluoroalkylene group, z being an integer of 0 or greater, G represents an alkylene group or arylene group optionally containing an ether oxygen, a group constituted of a combination thereof, or a single bond, L represents a bivalent connecting group, y being an integer of 0 or greater, D represents an optionally substituted organic group, and W represents any of groups of formulae:

O$^-$—
(III)

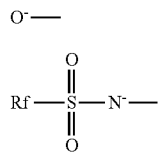
(IV)

wherein Rf represents a fluoroalkyl group having at least one fluorine atom introduced therein as a substituent.

(4) The actinic-ray- or radiation-sensitive resin composition according to any of items (1) to (3), wherein in general formula (II), D represents any of groups of formula:

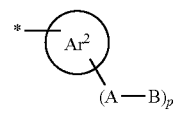
(V)

in which

Ar$^2$ represents an aromatic ring, in which a substituent other than -(A-B) groups may further be introduced, p is an integer of 1 or greater, A represents a single bond or any one, or a combination of two or more members selected from among an alkylene group, —O—, —S—, —C(=O)—, —C(=O)O—, —S(=O)—, —S(=O)$_2$— and —OS(=O)$_2$—, B represents a group containing an aliphatic group having 3 or more carbon atoms, provided that when p is 2 or greater, a plurality of -(A-B) groups may be identical to or different from each other, and

* represents a site of connection to L of general formula (II).

(5) The actinic-ray- or radiation-sensitive resin composition according to any of items (1) to (4), wherein in general formula (I), m is 2 or 3.

(6) The actinic-ray- or radiation-sensitive resin composition according to any of items (1) to (5), further comprising a resin that when acted on by an acid, is decomposed to thereby increase its solubility in an alkali developer.

(7) The actinic-ray- or radiation-sensitive resin composition according to any of items (1) to (6), further comprising a resin soluble in an alkali developer and an acid crosslinking agent capable of crosslinking with the resin soluble in an alkali developer under the action of an acid.

(8) A resist film formed from the actinic-ray- or radiation-sensitive resin composition according to any of items (1) to (7).

(9) A method of forming a pattern, comprising forming the actinic-ray- or radiation-sensitive resin composition according to any of items (1) to (7) into a film, exposing the film and developing the exposed film.

(10) The method of forming a pattern according to item (9), wherein the exposure is performed using X-rays, an electron beam or EUV.

(11) A compound of general formula (VI) that when exposed to actinic rays or radiation, generates an acid having a volume of 240 Å$^3$ or greater,

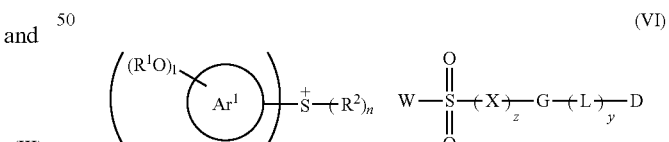
(VI)

in which

Ar$^1$ represents an aromatic ring, in which a substituent other than —(OR$^1$) groups may further be introduced, R$^1$ represents a linear or branched alkyl group or a cycloalkyl group, R$^2$ represents an optionally substituted aryl group, an optionally substituted alkyl group or an optionally substituted cycloalkyl group, l is an integer of 1 or greater, m is an integer of 1 to 3, and n an integer of 0 to 2, provided that m+n=3 is satisfied, provided that two members selected from among m $Ar^1$s and n $R^2$s may be bonded to each other to thereby form a ring in cooperation with the sulfur atom appearing in the formula, X represents an optionally substituted alkylene group or an optionally substituted fluoroalkylene group, z being an integer of 0 or greater, G represents an alkylene group or arylene group optionally containing an ether oxygen, a group constituted of a combination thereof, or a single bond, L represents a bivalent connecting group, y being an integer of 0 or greater, D represents an optionally substituted organic group, and W represents any of groups of formulae:

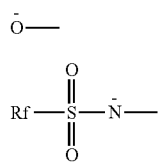

(III)

(IV)

wherein Rf represents a fluoroalkyl group having at least one fluorine atom introduced therein as a substituent.

(12) The compound according to item (11), wherein in general formula (VI), D represents any of groups of formula:

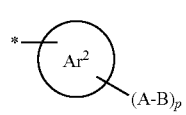

(V)

in which $Ar^2$ represents an aromatic ring, in which a substituent other than -(A-B) groups may further be introduced, p is an integer of 1 or greater, A represents a single bond or any one, or a combination of two or more members selected from among an alkylene group, —O—, —S—, —C(=O)—, —C(=O)O—, —S(=O)—, —S(=O)$_2$— and —OS(=O)$_2$—, B represents a group containing an aliphatic group having 3 or more carbon atoms, provided that when p is 2 or greater, a plurality of -(A-B) groups may be identical to or different from each other, and

* represents a site of connection to L of general formula (II).

(13) The compound according to items (11) to (12), wherein in general formula (VI), m is 2 or 3.

The present invention has made it feasible to provide an actinic-ray- or radiation-sensitive resin composition excelling in resolution, roughness characteristic, pattern configuration and outgassing performance without detriment to sensitivity and to provide a method of forming a pattern using the composition.

DETAILED DESCRIPTION OF THE INVENTION

The present invention will be described in detail below.

With respect to the term of a group (atomic group) used in this specification, the term even when there is no mention of "substituted and unsubstituted" encompasses groups not only having no substituent but also having substituents. For example, the term "alkyl groups" encompasses not only alkyls having no substituent (unsubstituted alkyls) but also alkyls having substituents (substituted alkyls).

The present invention is based on the finding of novel compounds (photoacid generators, hereinafter also referred to as "photoacid generators (A1)") that when exposed to actinic rays or radiation, generate an acid, which novel compounds are useful in an actinic-ray- or radiation-sensitive resin composition.

The actinic-ray- or radiation-sensitive resin composition of the present invention comprising any of the photoacid generators (A1) in its one form is a positive actinic-ray- or radiation-sensitive resin composition and in its other form is a negative actinic-ray- or radiation-sensitive resin composition.

The positive actinic-ray- or radiation-sensitive resin composition (more preferably positive resist composition) of the present invention may contain the photoacid generator (A1) and a resin (B) that is decomposed by the action of an acid to thereby exhibit an increased solubility in an alkali developer.

The negative actinic-ray- or radiation-sensitive resin composition (more preferably negative resist composition) of the present invention may contain the acid generator (A1), a resin (C) soluble in an alkali developer and an acid crosslinking agent (D) capable of crosslinking with the resin soluble in an alkali developer by the action of an acid.

[1] Compound that when Exposed to Actinic Rays or Radiation, Generates an Acid (Photoacid Generator (A1))

The photoacid generator (A1) to be contained in the actinic-ray- or radiation-sensitive resin composition of the present invention is an arylsulfonium salt containing at least one aryl ring on which there are a total of one or more electron donating groups, characterized in that the acid generated thereby upon exposure to actinic rays or radiation has a volume of 240 Å$^3$ or greater.

The photoacid generator (A1), as an electron donating group is introduced in its cation moiety, ensures favorable solubility in a developer or a solvent and exhibits favorable compatibility with the resin (B) or (C). Further, the occurrence of volatile low-molecular components can be suppressed. Moreover, as the anion moiety thereof has a bulky structure, the diffusion of generated acid in the resist film can be suppressed, so that the acid can be generated at desired localities only. Thus, the resolution and roughness characteristic can be enhanced.

With respect to the photoacid generator (A1), the cation moiety of the sulfonium salt will be described in detail below.

With respect to the photoacid generator (A1), a total of one or more electron donating groups are necessarily and satisfactorily introduced on at least one aryl ring of the cation structure of the arylsulfonium salt. When there are a plurality of aryl rings, the electron donating groups may be introduced on any one of the plurality of aryl rings or on a plurality of aryl rings thereof.

When a total of two or more electron donating groups are introduced on the aryl ring(s) of the photoacid generator (A1), if feasible, two or more electron donating groups may be bonded to each other to thereby form a ring.

The electron donating group is preferably any of an alkyl group, an alkoxy group, an amino group, a urea group, an alkoxyalkyl group, a cycloalkyloxyalkyl group, an acyloxyamino group, a cycloalkyl group, a cycloalkyloxy group and an allyl group. Each of these groups may be substituted with any of an alkyl group, an alkenyl group, an alkynyl group, an aryl group, a hydroxyl group, an alkoxy group, a thiol group, a thioalkoxy group, an amino group, a halogen atom and the like to such an extent that the electron donating capability is not lost. These substituents may further be substituted with these substituents, and, if feasible, may be bonded to each other to thereby form a ring.

Especially preferred electron donating groups are an alkyl group, an alkoxy group, an alkoxyalkyl group, a cycloalkyloxyalkyl group and a cycloalkyloxy group. Most preferred groups are an alkoxy group and a cycloalkyloxy group.

In the aryl groups contained in the cation moiety of the photoacid generator (A1), the sum of the Hammett values of all the substituents with reference to the sulfonium group is preferably in the range of −3.0 to −0.2, more preferably −2.5 to −0.5 and further more preferably −2.0 to −0.8. The expression "all the substituents with reference to the sulfonium group" means all the substituents bonded to the aryl skeleton of the cation structure of the sulfonium salt, provided that the sulfonium group is excluded. The Hammett values of substituents are based on the sulfonium group of the relevant aryl skeleton.

The Hammett's substituent constant σp value used in this description will be described below. The Hammett rule is an empirical rule proposed by L. P. Hammett in 1935 to quantitatively treat the effects of substituents on the reactions or equilibriums of benzene derivatives. The Hammett rule is now widely considered to be appropriate. Values σp and σm are used as substituent constants in the Hammett rule. These substituent constant values can be found in many common books, and are described in detail in, for example, "Lange's Handbook of Chemistry", edited by J. A. Dean, 12th edition, 1979, The McGraw-Hill Companies; Kagaku no Ryoiki (Realm of Chemistry), extra edition, No. 122, pages 96 to 103, 1979, (Nankodo Co., Ltd.); and Kagaku Seminar 10 (Chemical Seminar 10), Hammett rule-Structure and Reactivity, edited by Naoki Inamoto (1983, published by Maruzen Co., Ltd.).

In the present invention, individual substituents are defined by the Hammett's substituent constant σp and described with reference to the same. This is not limited to the substituents whose substituent constant values can be found in the literature such as the above common books, and naturally applies to the substituents whose substituent constant values cannot be found in the literature but, when measured according to the Hammett rule, would fall within stated ranges. In the present invention, use is made of Hammett values that can be found in Kagaku Seminar 10, Hammett rule-Structure and Reactivity, edited by Naoki Inamoto (1983, published by Maruzen Co., Ltd.) and kagaku Binran (Chemical Handbook), Basic Edition, Revised 5th Edition, edited by The Chemical Society of Japan (2004, published by Maruzen Co., Ltd.).

The generally used Hammett values are those at the m- or p-position. With respect to the Hammett values for use in the present invention, the value at the o-position is computed as being identical to the value at the p-position in terms of electronic effects.

An electron withdrawing group may be introduced as a substituent on the aryl rings of the photoacid generator (A1). However, it is preferred for the sum of the Hammett values of all the substituents with reference to the sulfonium group to be 0 or less. In this connection, the value of —OCH$_3$ is used for the alkoxy group and the value of —CH$_3$ is used for the alkyl group, and the value of the group linking two aryl groups to each other is not included in the sum.

In the photoacid generator (A1) according to the present invention, it is preferred for the cation moiety of the sulfonium salt thereof to be any of those of general formula (I) below.

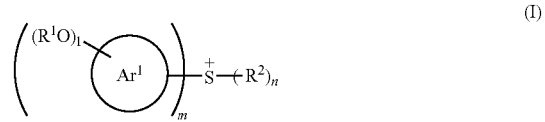

In the formula,

Ar$^1$ represents an aromatic ring, in which a substituent other than —(OR$^1$) groups may further be introduced.

R$^1$ represents a linear or branched alkyl group or a cycloalkyl group.

R$^2$ represents an optionally substituted aryl group, alkyl group or cycloalkyl group.

In the formula, l is an integer of 1 or greater, m is an integer of 1 to 3, and n an integer of 0 to 2, provided that m+n=3 is satisfied, and provided that two members selected from among m Ar$^1$s and n R$^2$s may be bonded to each other to thereby form a ring in cooperation with the sulfur atom appearing in the formula.

General formula (I) will be described in detail below.

In general formula (I), as the aromatic ring represented by Ar$^1$, there can be mentioned, for example, a phenyl group, a naphthyl group and the like, preferably a phenyl group.

In general formula (I), the linear or branched alkyl group represented by R$^1$ is preferably a linear or branched alkyl group having 1 to 20 carbon atoms, more preferably a linear or branched alkyl group having 1 to 12 carbon atoms. As such, there can be mentioned, for example, a methyl group, an ethyl group, a propyl group, an isopropyl group, an n-butyl group, an isobutyl group and the like.

The cycloalkyl group represented by R$^1$ is preferably a cycloalkyl group having 3 to 20 carbon atoms, more preferably a cycloalkyl group having 5 to 15 carbon atoms. As such, there can be mentioned, for example, a cyclopentyl group, a cyclohexyl group, a cycloheptyl group, a norbornyl group, an adamantyl group and the like.

The substitution of Ar$^1$ with the —(OR$^1$) group preferably occurs at the p- or m-position, more preferably at the m-position, from the viewpoint of roughness enhancement.

Substituents other than the —(OR$^1$) group may further be introduced in Ar$^1$. As such substituents, there can be mentioned, for example, a halogen group such as a fluorine atom, a chlorine atom, a bromine atom or an iodine atom; an aryloxy group such as a phenoxy group or a p-tolyloxy group; an alkylthioxy group such as a methylthioxy group, an ethylthioxy group or a tert-butylthioxy group; an arylthioxy group such as a phenylthioxy group or a p-tolylthioxy group; an alkoxycarbonyl group such as a methoxycarbonyl group or a butoxycarbonyl group; an aryloxycarbonyl group such as a phenoxycarbonyl group or a p-tolyloxycarbonyl group; an acetoxy group; a linear or branched alkyl group such as a methyl group, an ethyl group, a propyl group, a butyl group, a heptyl group, a hexyl group, a dodecyl group or a 2-ethylhexyl group; an alkenyl group such as a vinyl group, a propenyl group or a hexenyl group; an alkynyl group such as an acetylene group, a propynyl group or a hexynyl group; a cycloalkyl group; an aryl group such as a phenyl group or a tolyl group; a hydroxyl group; a carboxyl group; and a sulfonate group. Of these, a linear or branched alkyl group and a cycloalkyl group are preferred from the viewpoint of roughness enhancement.

In general formula (I), as the aryl group represented by R², there can be mentioned, for example, a phenyl group, a naphthyl group and the like, preferably a phenyl group.

The alkyl group represented by R² is preferably a linear or branched alkyl group having 1 to 20 carbon atoms, more preferably a linear or branched alkyl group having 1 to 12 carbon atoms. As such, there can be mentioned, for example, a methyl group, an ethyl group, a propyl group, an isopropyl group, an n-butyl group, an isobutyl group and the like.

The cycloalkyl group represented by R² is preferably a cycloalkyl group having 3 to 20 carbon atoms, more preferably a cycloalkyl group having 5 to 15 carbon atoms. As such, there can be mentioned, for example, a cyclopentyl group, a cyclohexyl group, a cycloheptyl group, a norbornyl group, an adamantyl group and the like.

A substituent may be introduced in R². For example, as such, there can be mentioned a halogen atom, an alkyl group, an alkenyl group, an alkynyl group, an aryl group, a cyano group, a hydroxyl group, a nitro group, a carboxyl group, an alkoxy group, an aryloxy group, a silyloxy group, an acyloxy group, a carbamoyloxy group, an alkoxycarbonyloxy group, an aryloxycarbonyloxy group, an aminocarbonylamino group, an alkoxycarbonylamino group, an aryloxycarbonylamino group, a sulfamoylamino group, an alkyl- or arylsulfonylamino group, a mercapto group, an alkylthio group, an arylthio group, a sulfamoyl group, a sulfo group, an alkyl- or arylsulfinyl group, an alkyl- or arylsulfonyl group, an acyl group, an aryloxycarbonyl group, an alkoxycarbonyl group, a carbamoyl group, an imido group, a silyl group, a ureido group and the like.

In general formula (I), m is preferably 2 or 3, more preferably 3.

When m is 1 and n is 2, two R²s may be bonded to each other to thereby form a ring structure. The ring may contain, besides the sulfur atom appearing in the formula, an oxygen atom, a sulfur atom, an ester bond, an amido bond or a carbonyl group. As a preferred form, there can be mentioned a structure in which two R²s are bonded to each other to thereby form an alkylene group, which alkylene group forms a 5 or 6-membered ring (namely, a tetrahydrothiophene ring or a tetrahydrothiopyran ring) in cooperation with the sulfur atom appearing in the formula.

When m is 2 and n is 1, or when m is 3 and n is 0, two Ar¹s, or Ar¹ and R² may be bonded to each other to thereby form a ring structure. The formed ring may contain, besides the sulfur atom appearing in the formula, an oxygen atom, a sulfur atom, an ester bond, an amido bond or a carbonyl group. The ring may be monocyclic or polycyclic, and may be a condensed ring. As a preferred form, there can be mentioned a structure in which two Ar¹s, or Ar¹ and R² are simultaneously phenyl groups and two phenyl groups are combined with each other to thereby form a dibenzothiophene ring or a dibenzothiopyran ring.

Preferred examples of the sulfonium cations of general formula (I) will be shown below, which however in no way limit the present invention. With respect to each of compound examples (C-1) to (C-53), the sum of the Hammett values of all the substituents with reference to the sulfonium group is given in Table 1.

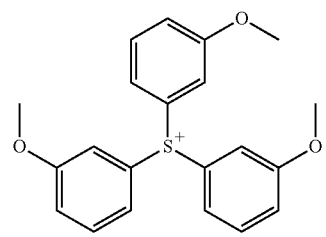
(C-1)

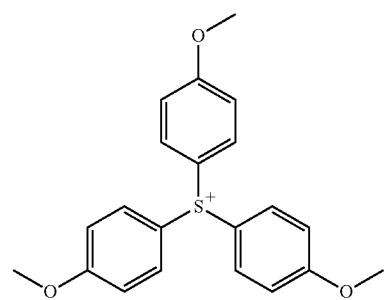
(C-2)

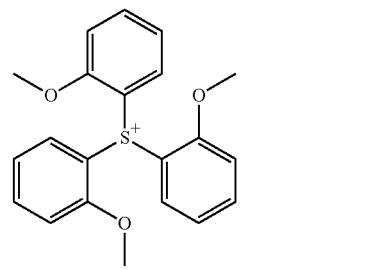
(C-3)

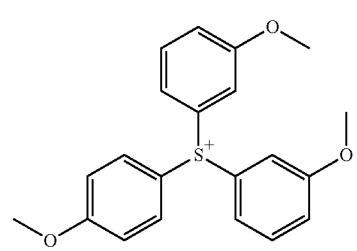
(C-4)

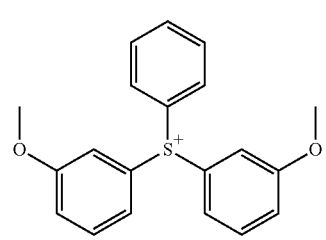
(C-5)

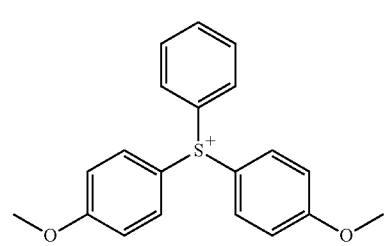
(C-6)

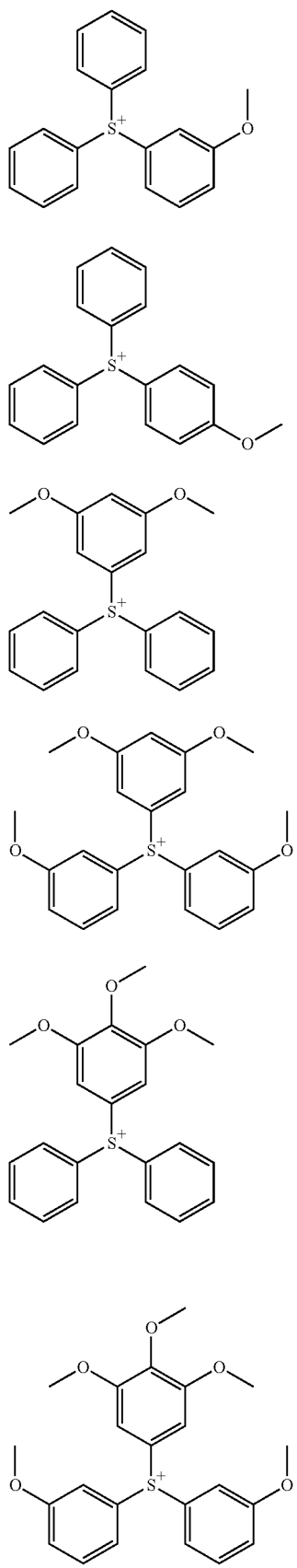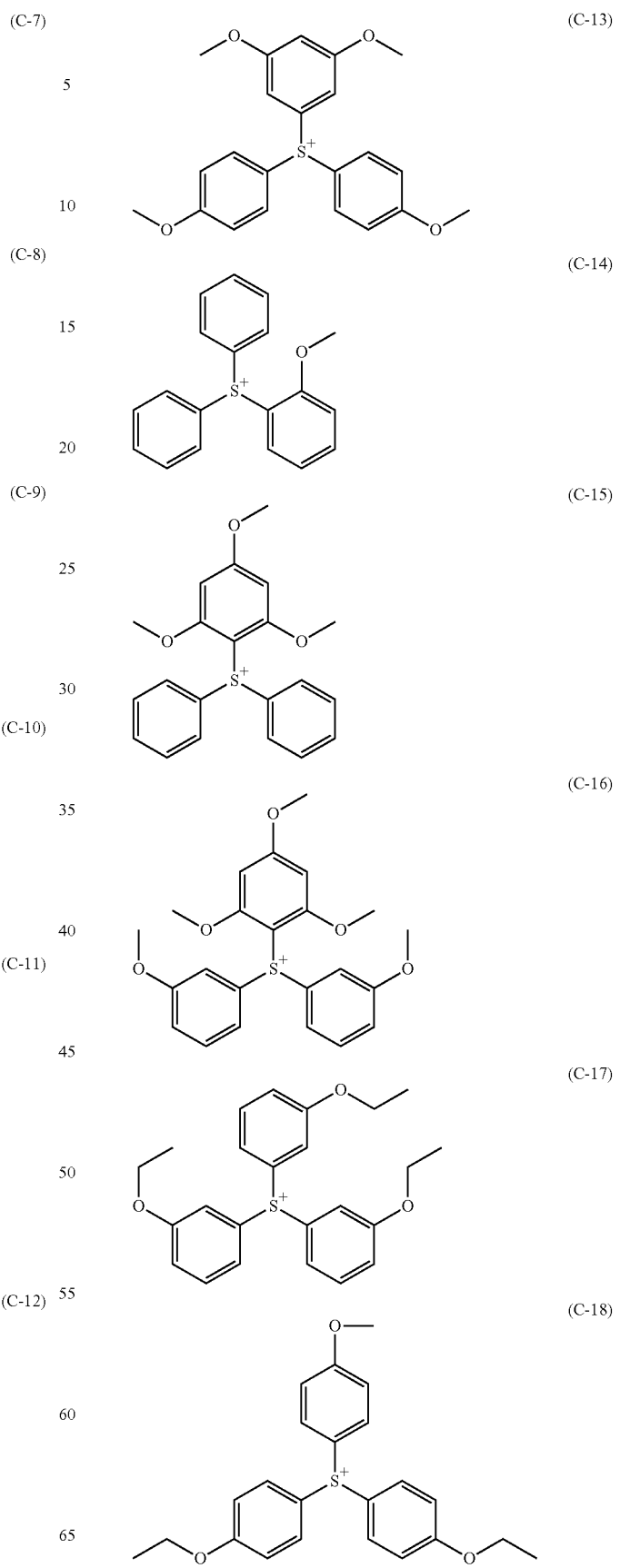

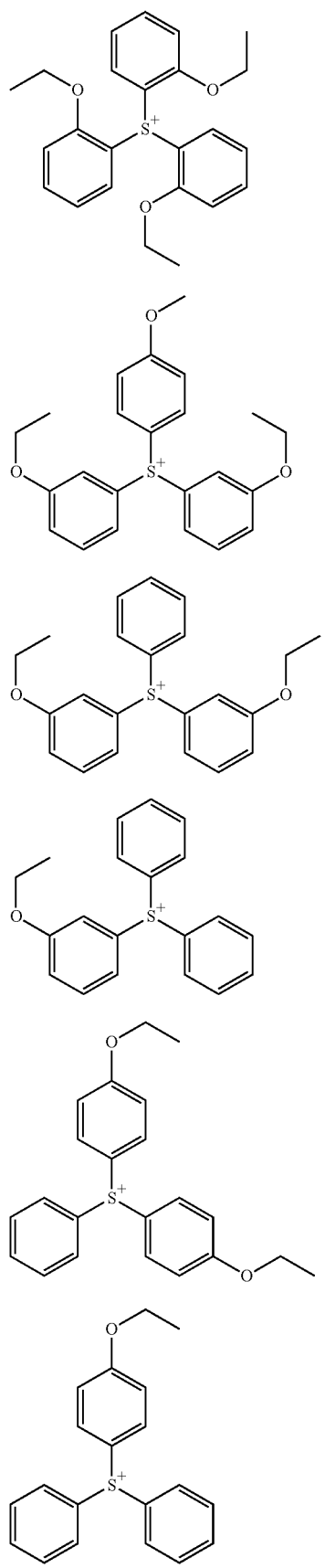
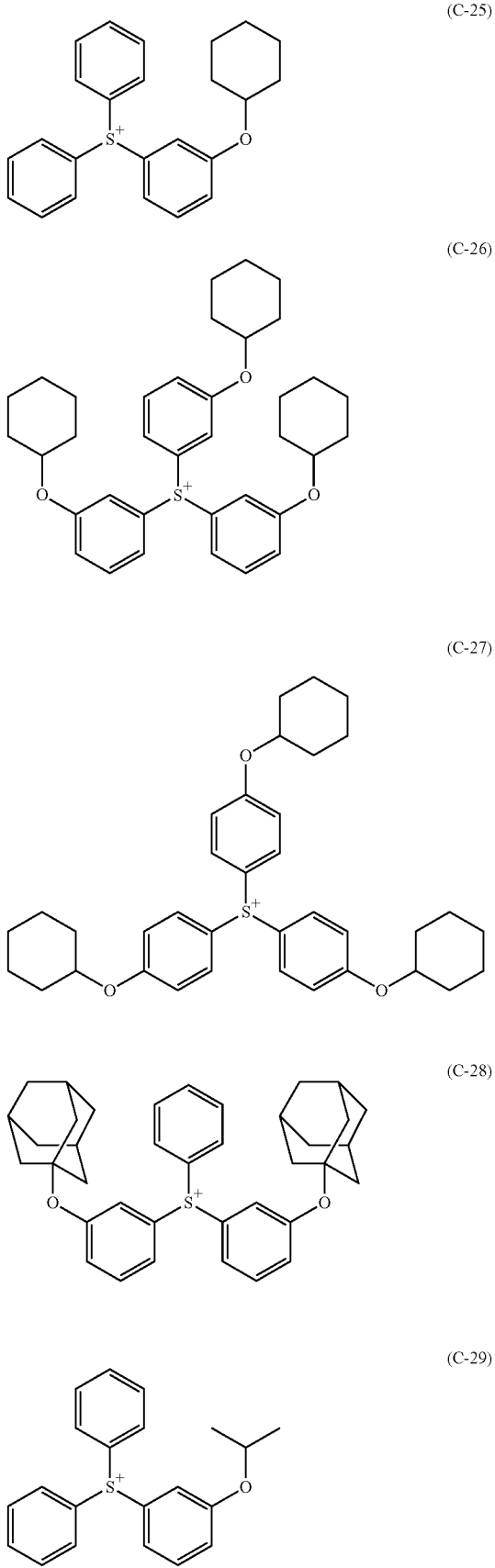

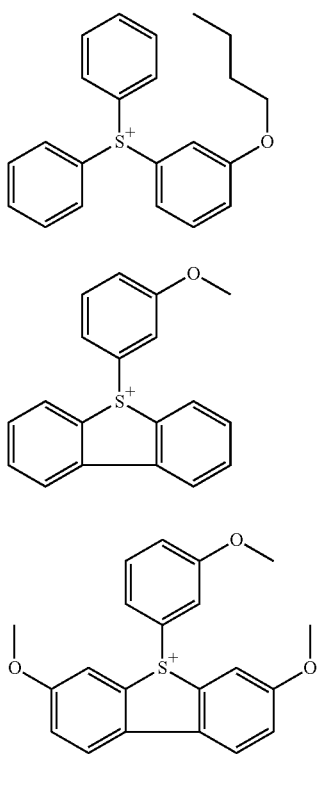
(C-30)
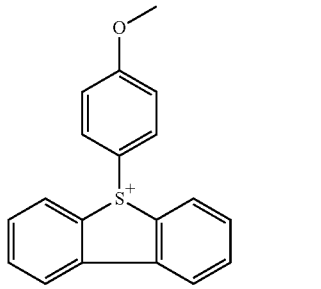
(C-31)
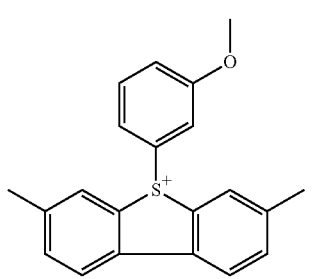
(C-32)
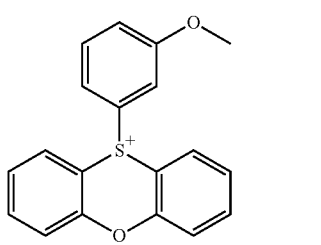
(C-33)
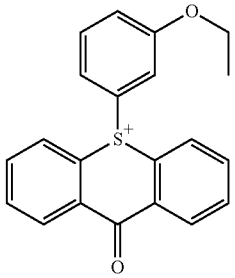
(C-34)
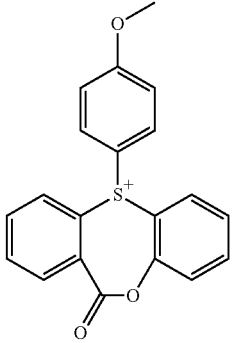
(C-35)
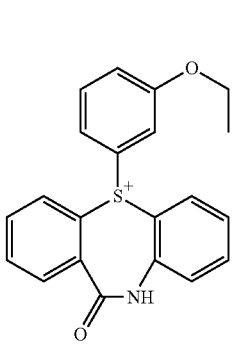
(C-36)
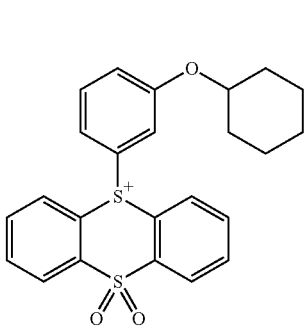
(C-37)
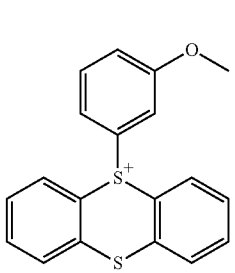
(C-38)
(C-39)
(C-40)

(C-41)
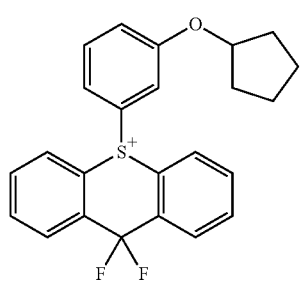
(C-42)
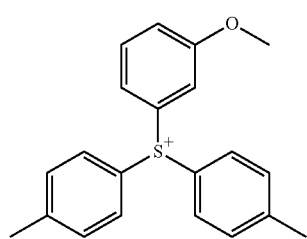
(C-43)
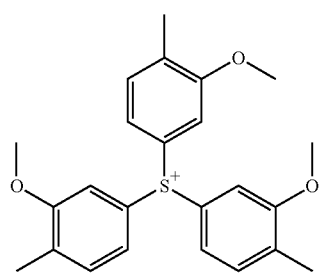
(C-44)
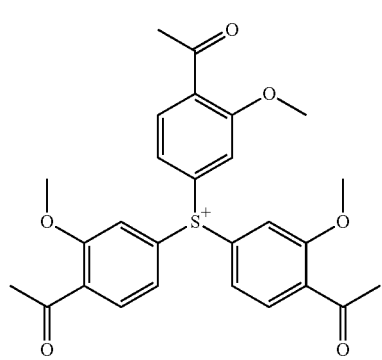
(C-45)
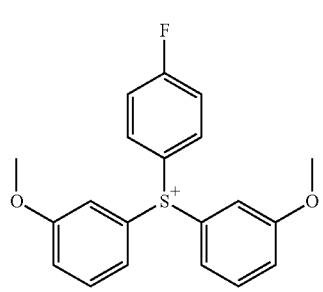
(C-46)
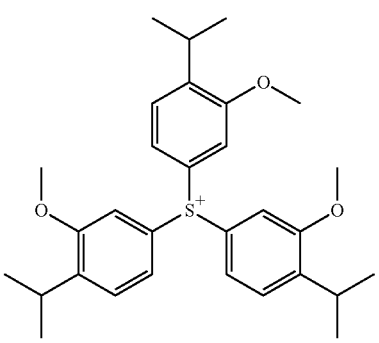
(C-47)
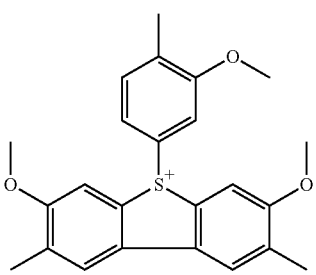
(C-48)
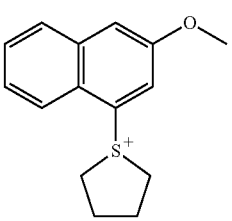
(C-49)
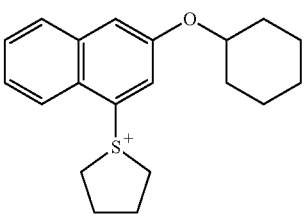
(C-50)
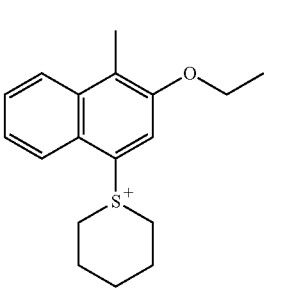
(C-51)
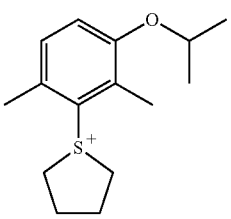

(C-52)

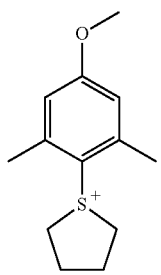

(C-53)

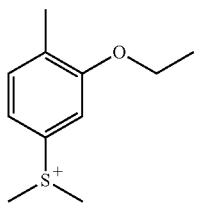

TABLE 1

| Compound ex. No. | Sum of Hammett Values |
|---|---|
| (C-1) | −0.81 |
| (C-2) | −0.81 |
| (C-3) | −0.81 |
| (C-4) | −0.81 |
| (C-5) | −0.54 |
| (C-6) | −0.54 |
| (C-7) | −0.27 |
| (C-8) | −0.27 |
| (C-9) | −0.81 |
| (C-10) | −1.08 |
| (C-11) | −0.81 |
| (C-12) | −1.35 |
| (C-13) | −1.08 |
| (C-14) | −0.27 |
| (C-15) | −0.81 |
| (C-16) | −1.35 |
| (C-17) | −0.81 |
| (C-18) | −0.81 |
| (C-19) | −0.81 |
| (C-20) | −0.81 |
| (C-21) | −0.54 |
| (C-22) | −0.27 |
| (C-23) | −0.54 |
| (C-24) | −0.27 |
| (C-25) | −0.27 |
| (C-26) | −0.81 |
| (C-27) | −0.81 |
| (C-28) | −0.54 |
| (C-29) | −0.27 |
| (C-30) | −0.27 |
| (C-31) | −0.27 |
| (C-32) | −0.81 |
| (C-33) | −0.27 |
| (C-34) | −0.27 |
| (C-35) | −0.27 |
| (C-36) | −0.27 |
| (C-37) | −0.27 |
| (C-38) | −0.27 |
| (C-39) | −0.27 |
| (C-40) | −0.27 |
| (C-41) | −0.27 |
| (C-42) | −0.61 |
| (C-43) | −1.32 |
| (C-44) | −0.27 |
| (C-45) | −0.89 |
| (C-46) | −1.32 |
| (C-47) | −1.32 |

TABLE 1-continued

| Compound ex. No. | Sum of Hammett Values |
|---|---|
| (C-48) | −0.27 |
| (C-49) | −0.27 |
| (C-50) | −0.44 |
| (C-51) | −0.61 |
| (C-52) | −0.61 |
| (C-53) | −0.44 |

With respect to the photoacid generator (A1), the anion moiety of the sulfonium salt will be described in detail below.

The photoacid generator (A1) is characterized in that the acid generated thereby upon exposure to actinic rays or radiation has a volume of 240 Å³ or greater. Namely, the anion moiety of the sulfonium salt as the photoacid generator (A1) has a bulky group. Preferably, the volume of the generated acid is in the range of 300 to 600 Å³.

It is preferred for the anion moiety of the sulfonium salt as the photoacid generator (A1) according to the present invention to be any of those of general formula (II) below.

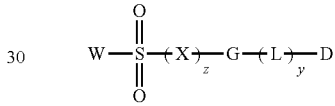

(II)

In the formula,

X represents an optionally substituted alkylene group or an optionally substituted fluoroalkylene group, z being an integer of 0 or greater.

G represents an alkylene group or arylene group optionally containing an ether oxygen, a group constituted of a combination thereof, or a single bond.

L represents a bivalent connecting group, y being an integer of 0 or greater.

D represents an optionally substituted organic group.

W represents any of groups of formulae (III) and (IV) below.

(III)

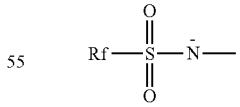

(IV)

In the formulae, Rf represents a fluoroalkyl group having at least one fluorine atom introduced therein as a substituent.

General formula (II) will be described in detail below.

Each of the alkylene group and fluoroalkylene group represented by X preferably has 1 to 10 carbon atoms, more preferably 1 to 5 carbon atoms. X is preferably a fluoroalkylene group, more preferably any of fluoroalkylene groups of formula below.

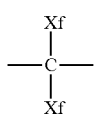

In the formula, each of Xf's independently represents a fluorine atom or an alkyl group substituted with at least one fluorine atom, and z is preferably an integer of 0 to 5, more preferably 0 to 3.

G represents a single bond, an alkylene group (including a cycloalkylene group) or arylene group optionally containing an ether oxygen, or a group constituted of a combination thereof. The combined groups may be connected to each other through an oxygen atom. When G is a group other than a single bond, the group preferably has 1 to 10 carbon atoms, more preferably 1 to 5 carbon atoms.

As the bivalent connecting group represented by L, there can be mentioned, for example, —COO—, —OCO—, —CO—, —O—, —S—, —SO—, —SO$_2$—, —SO$_3$—, —NH—, an alkylene group, a cycloalkylene group or an alkenylene group. Of these, —COO—, —OCO—, —CO—, —O—, —S—, —SO—, —SO$_2$— and —SO$_3$— are preferred. —COO—, —OCO—, —SO$_2$— and —SO$_3$— are more preferred.

In the formula, y is preferably an integer of 0 to 4, more preferably 0 to 2.

As the optionally substituted organic group represented by D, there can be mentioned an optionally substituted aromatic group or aliphatic group. The aromatic group or aliphatic group may contain a heteroatom. The organic group represented by D preferably has 1 to 50 carbon atoms, more preferably 1 to 30 carbon atoms.

It is preferred for the optionally substituted aromatic group represented by D to be any of groups of general formula (V) below.

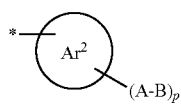

(V)

In the formula,

Ar$^2$ represents an aromatic ring, in which a substituent other than -(A-B) groups may further be introduced, and p is an integer of 1 or greater.

A represents a single bond or any one, or a combination of two or more members selected from among an alkylene group, —O—, —S—, —C(=O)—, —C(=O)O—, —S(=O)—, —S(=O)$_2$— and —OS(=O)$_2$—.

B represents a group containing an aliphatic group having 3 or more carbon atoms.

When p is 2 or greater, a plurality of -(A-B) groups may be identical to or different from each other.

* represents a site of connection to L of general formula (II).

The aromatic ring represented by Ar$^2$ preferably has 6 to 30 carbon atoms, and may contain a heteroatom. A substituent other than -(A-B) groups may further be introduced in the aromatic ring represented by Ar$^2$.

As the aromatic ring, there can be mentioned, for example, a benzene ring, a naphthalene ring, a pentalene ring, an indene ring, an azulene ring, a heptalene ring, an indecene ring, a perylene ring, a pentacene ring, an acenaphthalene ring, a phenanthrene ring, an anthracene ring, a naphthacene ring, a chrysene ring, a triphenylene ring, a fluorene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an iodolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiin ring, a phenothiazine ring, a phenazine ring and the like. Of these, a benzene ring, a naphthalene ring and an anthracene ring are preferred from the viewpoint of simultaneous attainment of roughness enhancement and sensitivity increase. A benzene ring is more preferred.

When a substituent other than -(A-B) groups is further introduced in the aromatic ring, as such a substituent, there can be mentioned, for example, a halogen group such as a fluorine atom, a chlorine atom, a bromine atom or an iodine atom; a methoxy group or an ethoxy group; an aryloxy group such as a phenoxy group or a p-tolyloxy group; a methylthioxy group or an ethylthioxy group; an arylthioxy group such as a phenylthioxy group or a p-tolylthioxy group; a methoxycarbonyl group or an ethoxycarbonyl group; an aryloxycarbonyl group such as a phenoxycarbonyl group; an acetoxy group; a methyl group or an ethyl group; a vinyl group; an acetylene group; an aryl group such as a phenyl group or a tolyl group; a non-acetyl acyl group such as a benzoyl group or a toluoyl group; a hydroxyl group; a carboxyl group; a sulfonate group and the like. Of these, a methyl group, an ethyl group and a hydroxyl group are preferred from the viewpoint of roughness improvement.

It is preferred for A to be constituted of fewer atoms from the viewpoint of resolution and roughness. Preferably, A represents a single bond, —O—, —S— or —CO$_2$—. A single bond is most preferred.

As the aliphatic group having 3 or more carbon atoms represented by B, there can be mentioned a noncyclic hydrocarbon group or a cycloaliphatic group.

As the noncyclic hydrocarbon group having 3 or more carbon atoms, there can be mentioned an isopropyl group, a t-butyl group, a t-pentyl group, a neopentyl group, an s-butyl group, an isobutyl group, an isohexyl group, a 3,3-dimethylpentyl group, a 2-ethylhexyl group and the like. The noncyclic hydrocarbon group more preferably has 3 to 20 carbon atoms. A substituent may be introduced in the noncyclic hydrocarbon group.

As the cycloaliphatic group having 3 or more carbon atoms, there can be mentioned a cycloalkyl group such as a cyclobutyl group, a cyclopentyl group, a cyclohexyl group, a cycloheptyl group or a cyclooctyl group, an adamantyl group, a norbornyl group, a bornyl group, a camphenyl group, a decahydronaphthyl group, a tricyclodecanyl group, a tetracyclodecanyl group, a camphoroyl group, a dicyclohexyl group, a pinenyl group and the like. The cycloaliphatic group preferably has 5 to 20 carbon atoms. A substituent may be introduced in the cycloaliphatic group.

When a substituent is introduced in the noncyclic hydrocarbon group or cycloaliphatic group, as such a substituent, there can be mentioned, for example, a halogen group such as a fluorine atom, a chlorine atom, a bromine atom or an iodine atom; an alkoxy group such as a methoxy group, an ethoxy group or a tert-butoxy group; an aryloxy group such as a phenoxy group or a p-tolyloxy group; an alkylthioxy group such as a methylthioxy group, an ethylthioxy group or a tert-butylthioxy group; an arylthioxy group such as a phenylthioxy group or a p-tolylthioxy group; an alkoxycarbonyl group such as a methoxycarbonyl group or a butoxycarbonyl group; an aryloxycarbonyl group such as a phenoxycarbonyl group; an acetoxy group; a linear or branched alkyl group such as a methyl group, an ethyl group, a propyl group, a butyl group, a heptyl group, a hexyl group, a dodecyl group or a 2-ethylhexyl group; a cycloalkyl group such as a cyclohexyl group; an alkenyl group such as a vinyl group, a propenyl group or a hexenyl group; an alkynyl group such as an acetylene group, a propynyl group or a hexynyl group; an aryl group such as a phenyl group or a tolyl group; a hydroxyl group; a carboxyl group; a sulfonate group; a carbonyl group; and the like. Of these, a linear or branched alkyl group is preferred from the viewpoint of the simultaneous attainment of roughness improvement and sensitivity enhancement.

Specific examples of the groups having these cycloaliphatic groups or noncyclic hydrocarbon groups will be shown below. In the formulae, * represents a site of connection to A (when A is a single bond, Ar).

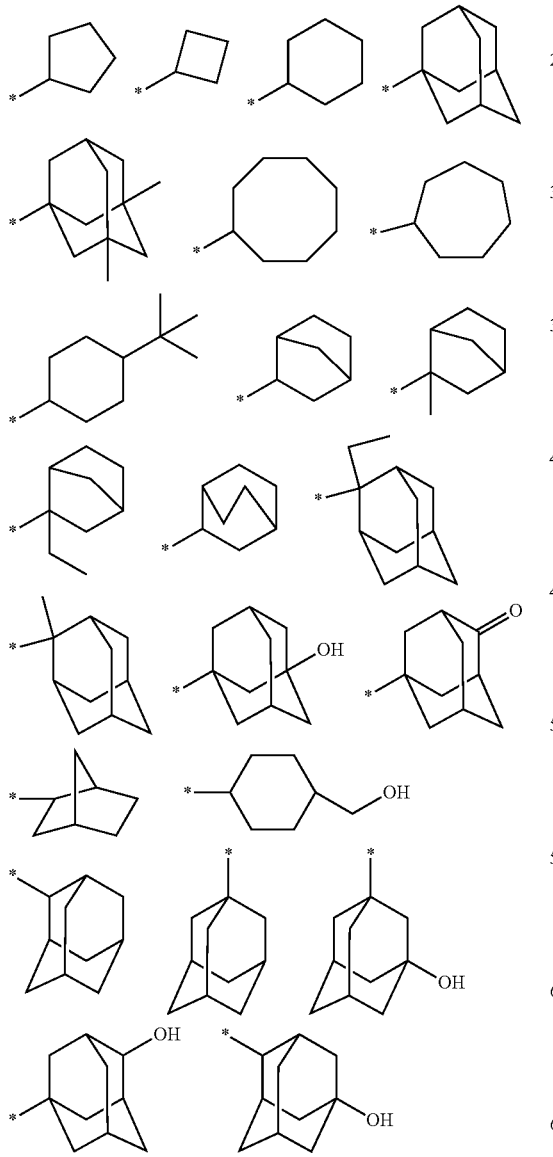

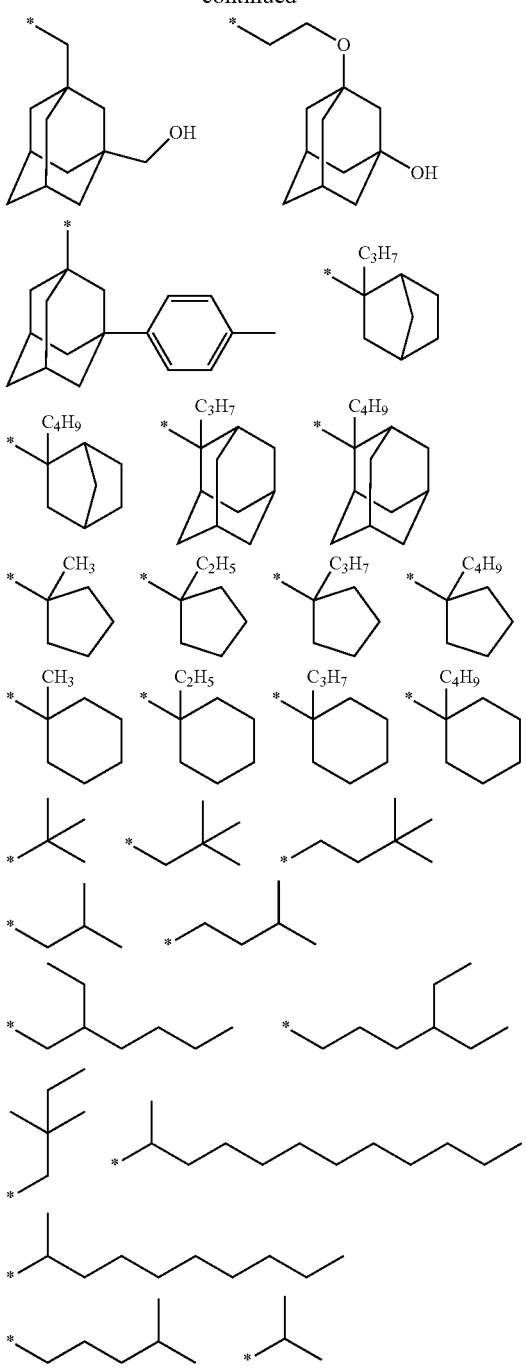

Of these, the following structures are preferred.

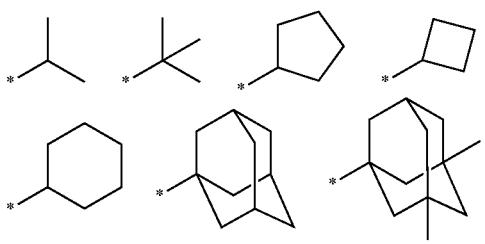

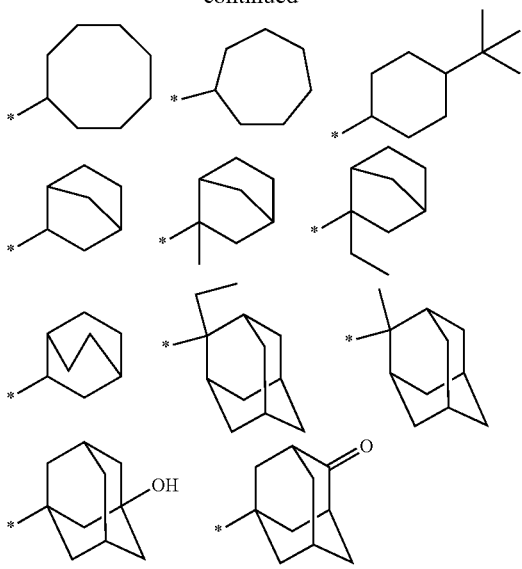

Each of the indicated computed values is the value of the volume of the acid resulting from bonding of a proton to the relevant anion moiety.

The values were determined in the following manner using "WinMOPAC" available from Fujitsu Limited. First, the chemical structure of the acid from each of the examples was inputted. Subsequently, assuming that this structure is an initial structure, the most stable conformation of relevant individual acid was determined by the molecular force field calculation according to the MM3 method. Thereafter, the "accessible volume" of the relevant individual acid was computed by carrying out a molecular orbit calculation according to the PM3 method with respect to the above most stable conformation.

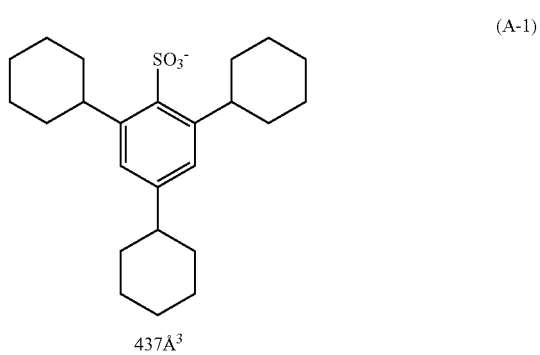

(A-1)

437Å$^3$

Among the aliphatic groups each having 3 or more carbon atoms represented by B, cycloaliphatic groups are preferred from the viewpoint of resolution and roughness. Among the cycloaliphatic groups, a cycloalkyl group, an adamantyl group and a norbornyl group are preferred from the viewpoint of roughness improvement. A cycloalkyl group is more preferred. Among cycloalkyl groups, a cyclohexyl group is most preferred.

Further, p is an integer of 1 or greater. From the viewpoint of roughness improvement, 2 to 5 are preferred, and 2 to 4 are more preferred. Most preferably, p is 3.

It is preferred for the substitution with -(A-B) group to occur at least one o-position with respect to the site of connection to L from the viewpoint of roughness improvement. More preferably, two o-positions are substituted with -(A-B) groups.

As the optionally substituted aliphatic group containing a heteroatom represented by D, there can be mentioned, for example, a lactone ring, a lactam ring, a piperidine ring, a pyrrolidine ring and the like.

W represents any of groups of formulae (III) and (IV) below.

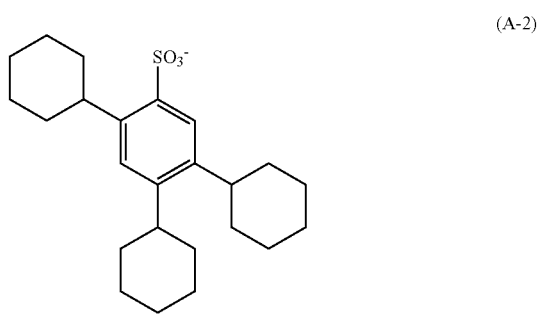

(A-2)

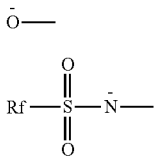

(III)

$$\bar{O}—$$

(IV)

$$Rf—\overset{\overset{O}{\|}}{\underset{\underset{O}{\|}}{S}}—\bar{N}—$$

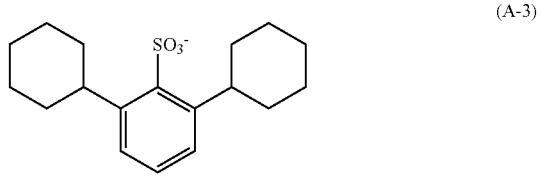

(A-3)

In the formulae, Rf represents a fluoroalkyl group having at least one fluorine atom introduced therein as a substituent. The fluoroalkyl group preferably has 1 to 10 carbon atoms, more preferably 1 to 5 carbon atoms. Rf is preferably a perfluoroalkyl group, more preferably $CF_3$, $C_2F_5$, $C_3F_7$, $C_4F_9$ or $C_5F_{11}$.

Preferred examples of the anion moieties of general formula (II) will be shown below, which however in no way limit the present invention. With respect to some of these examples, the computed value of volume of each thereof is indicated.

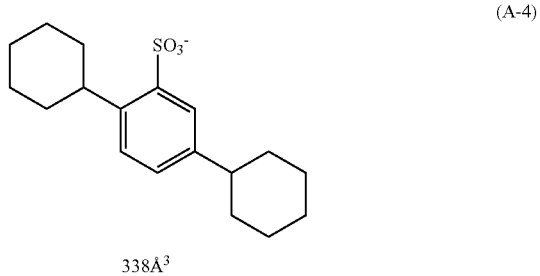

(A-4)

338Å$^3$ (A-5) 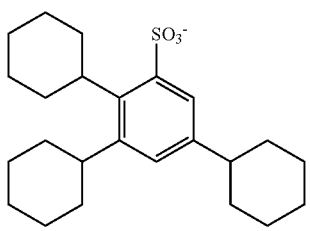
(A-6) 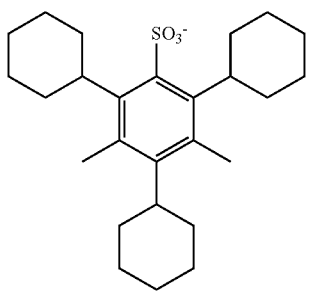
(A-7) 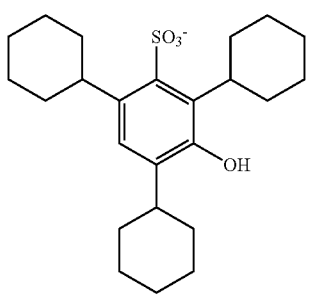
(A-8) 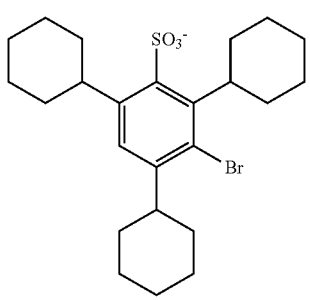
(A-9) 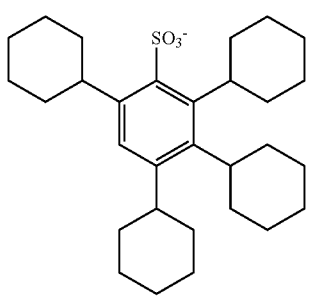
(A-10) 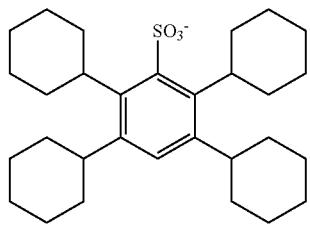
529Å$^3$
(A-11) 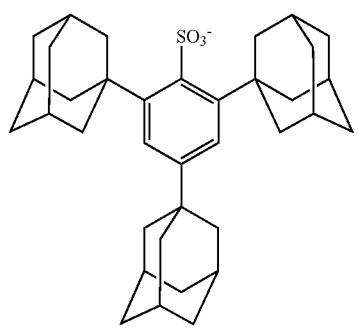
(A-12) 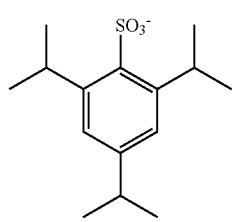
303Å$^3$
(A-13) 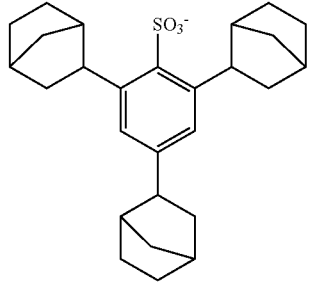
(A-14) 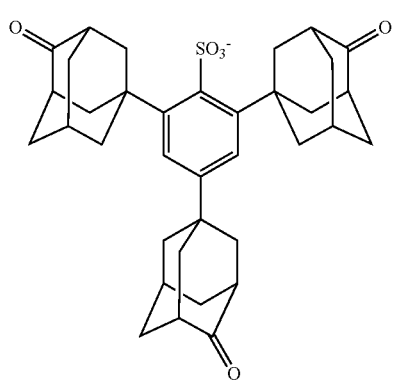

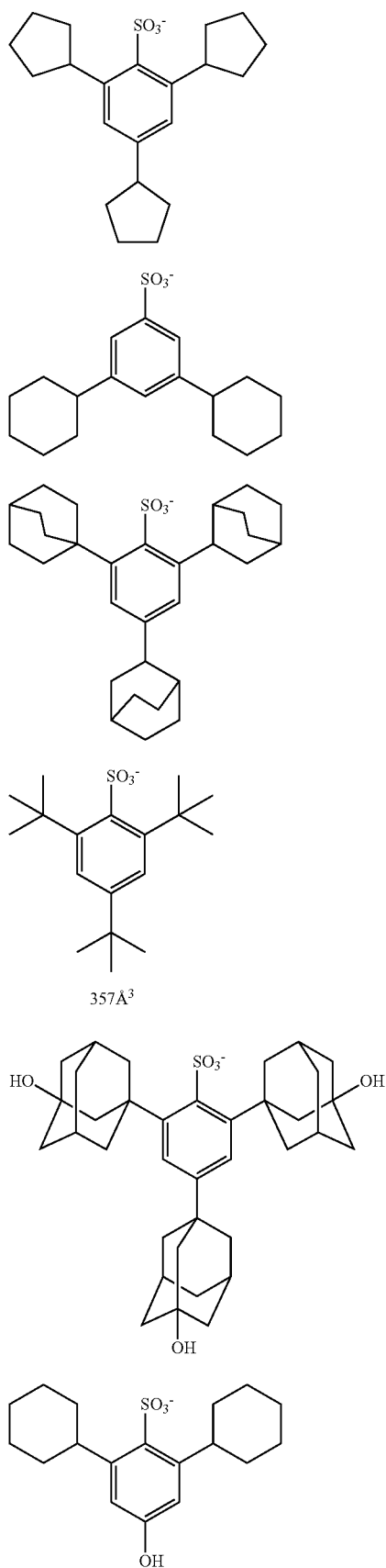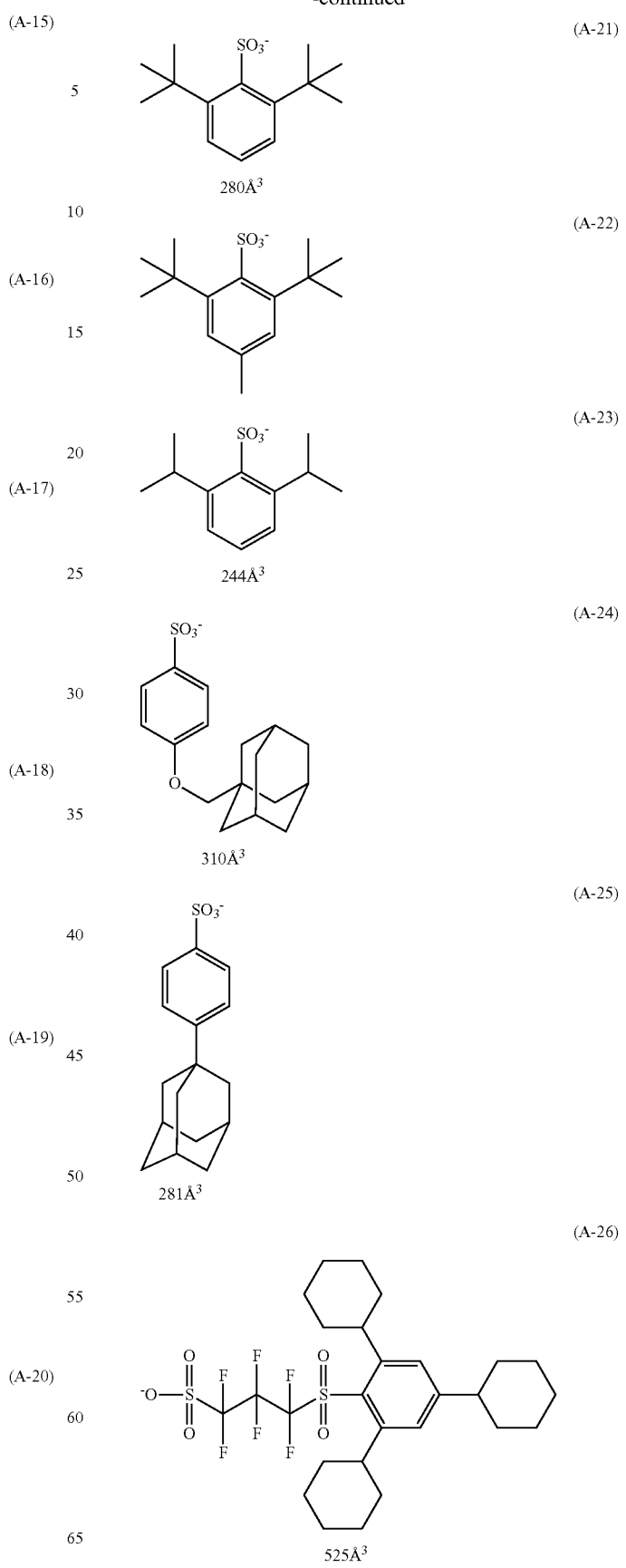

(A-27)
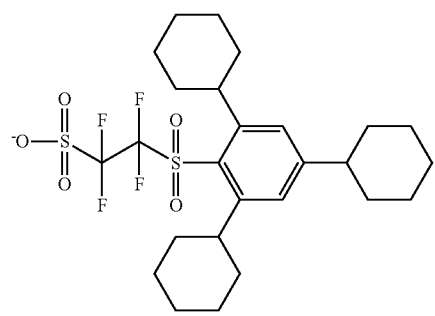
(A-28)
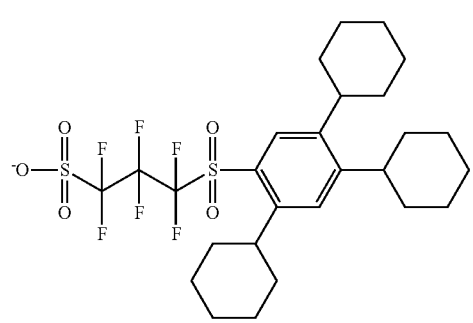
(A-29)
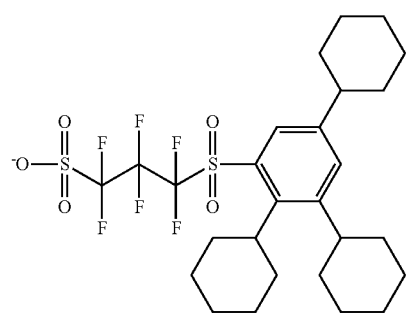
(A-30)
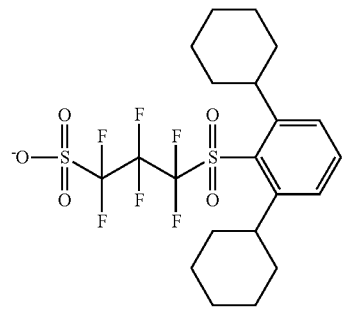
(A-31)
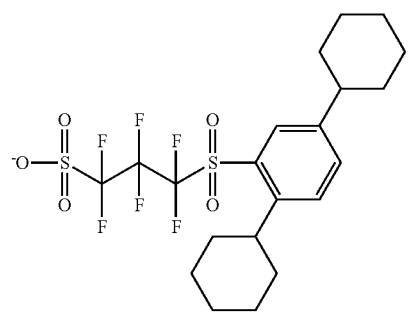
(A-32)
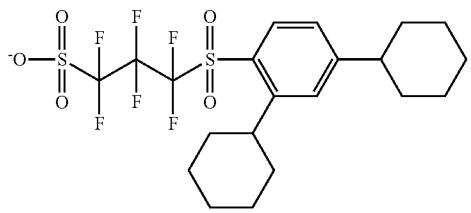
(A-33)
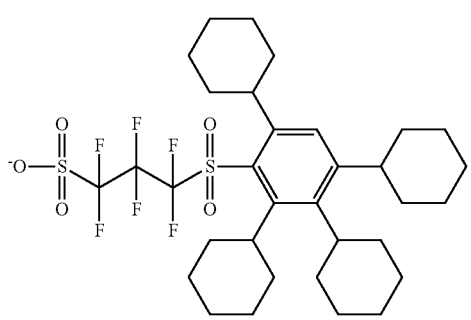
(A-34)
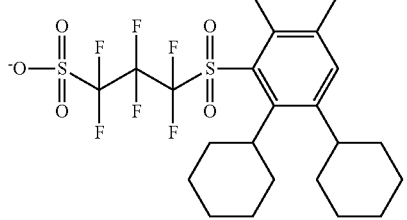
(A-35)
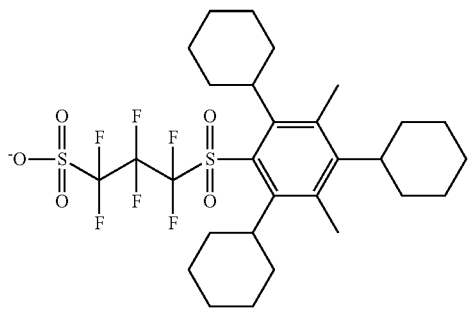
(A-36)
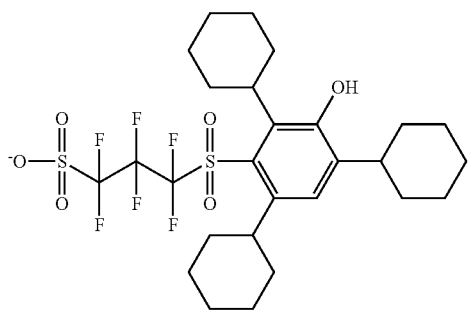

-continued
(A-37)
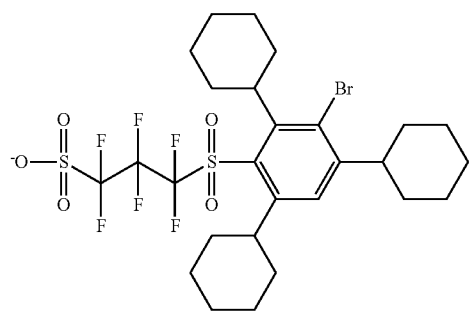
(A-38)
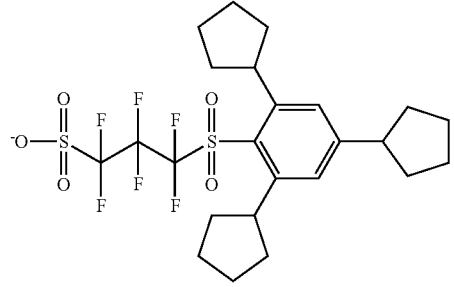
(A-39)
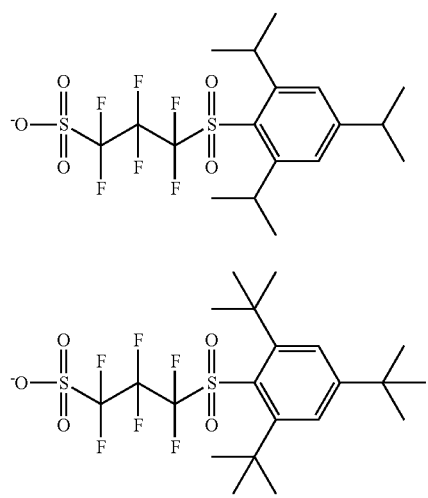
(A-40)
395Å³
(A-41)
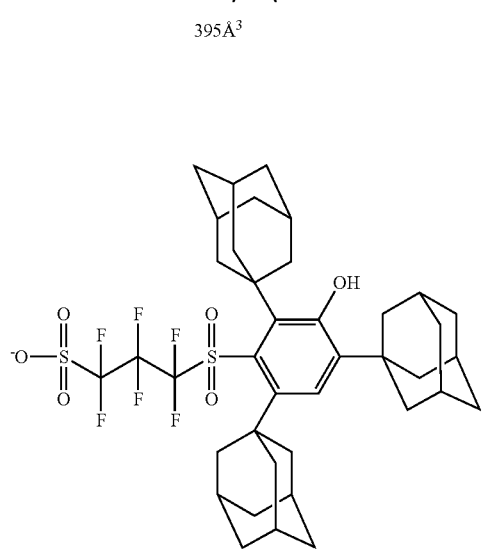
-continued
(A-42)
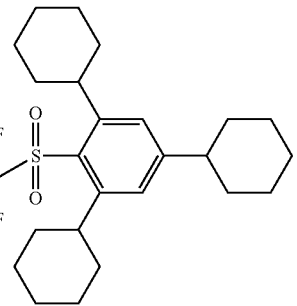
582Å³
(A-43)
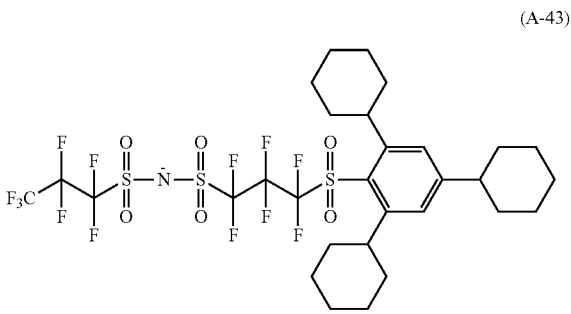
(A-44)
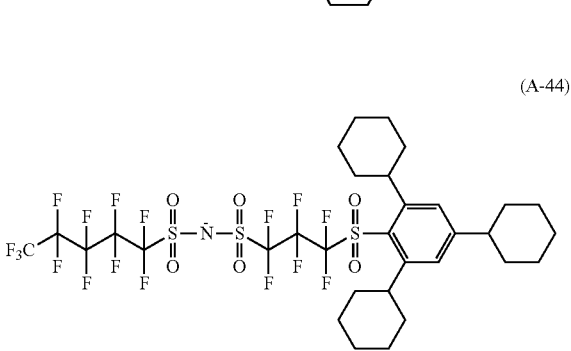
(A-45)
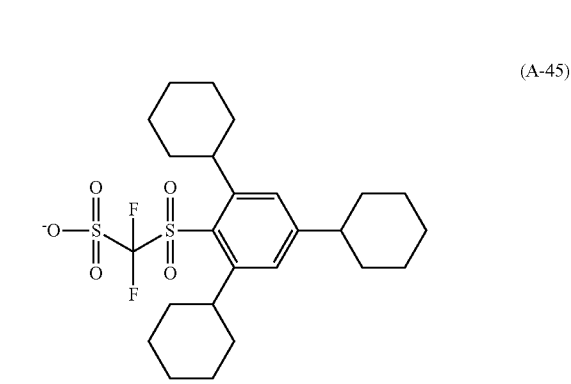
(A-46)
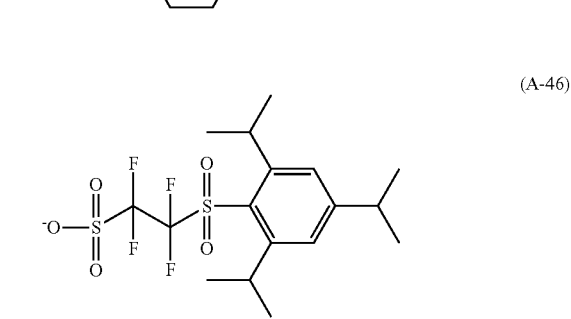

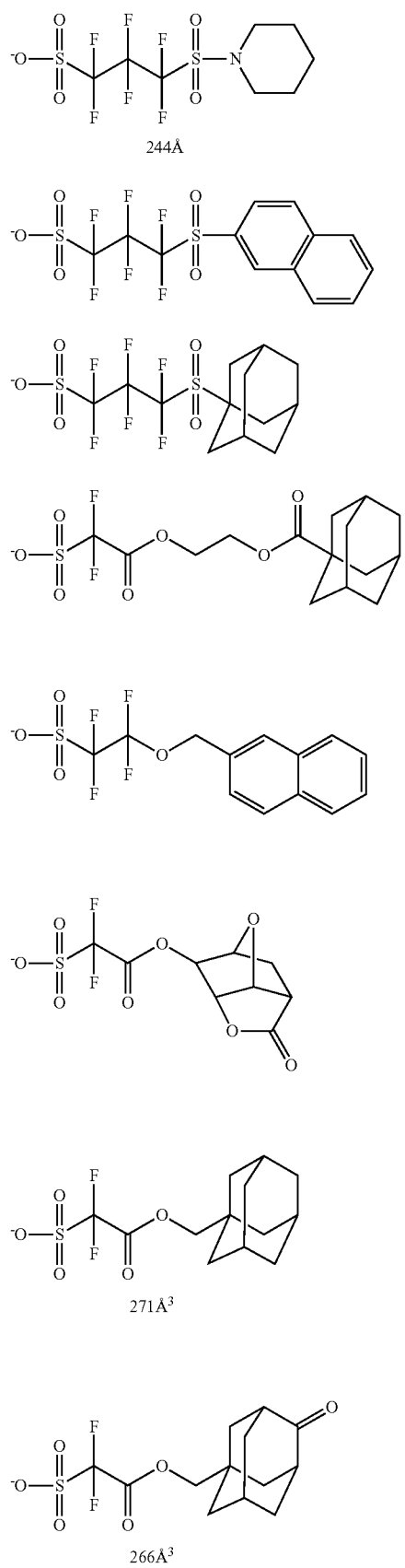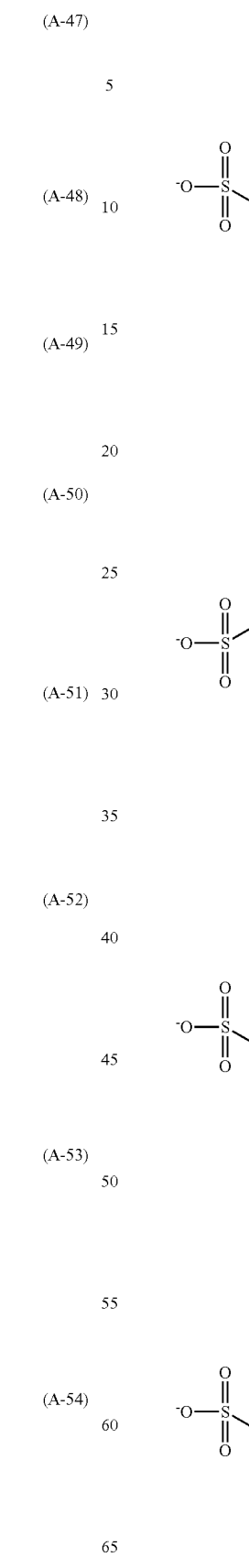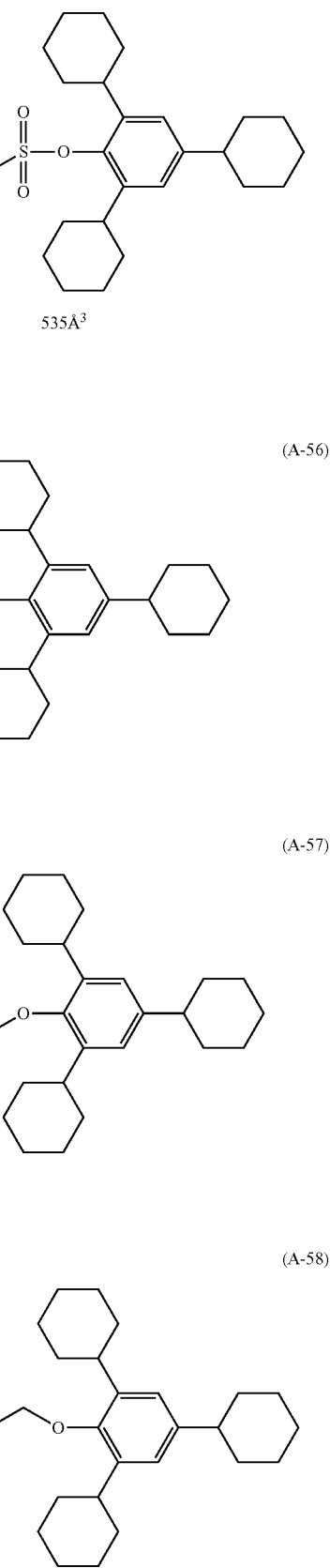

(A-59) 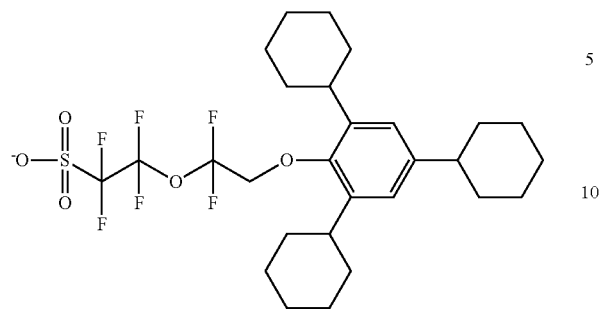
(A-60) 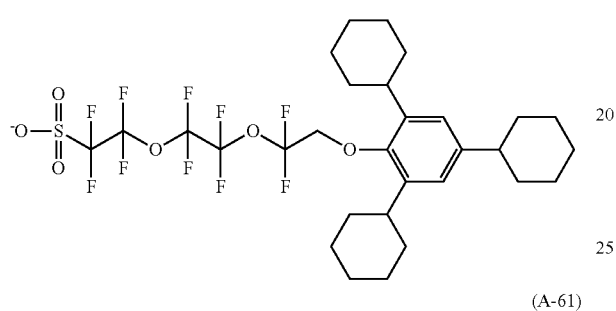
(A-61) 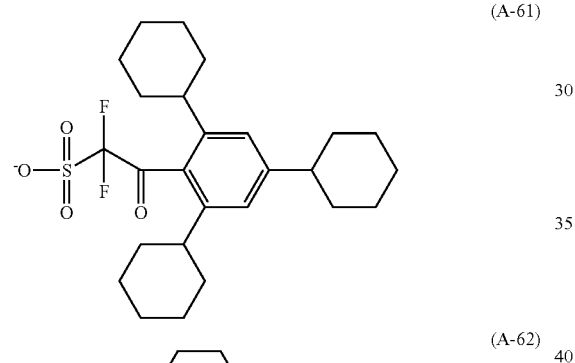
(A-62) 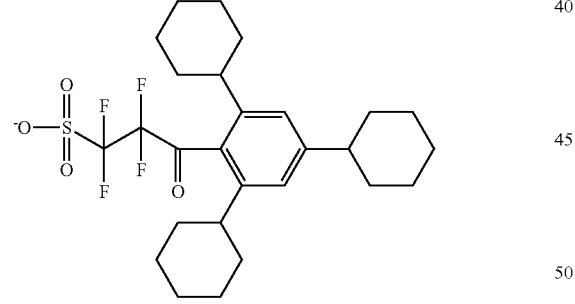
(A-63) 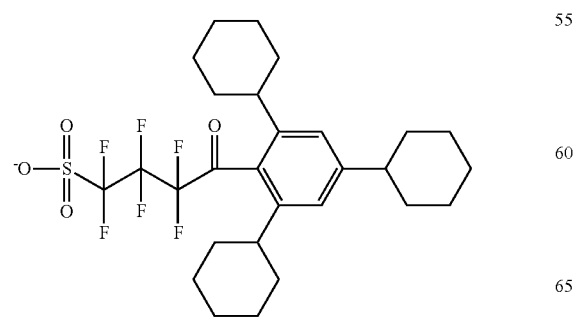
(A-64) 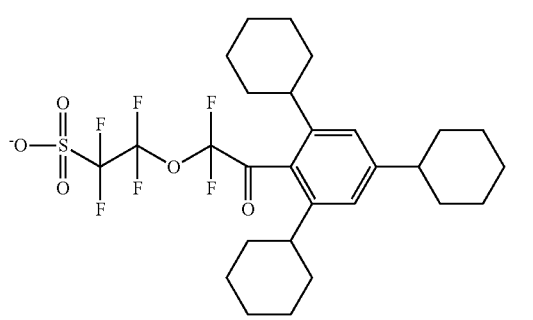
(A-65) 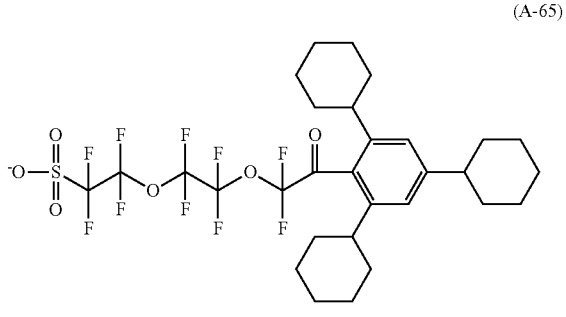
(A-66) 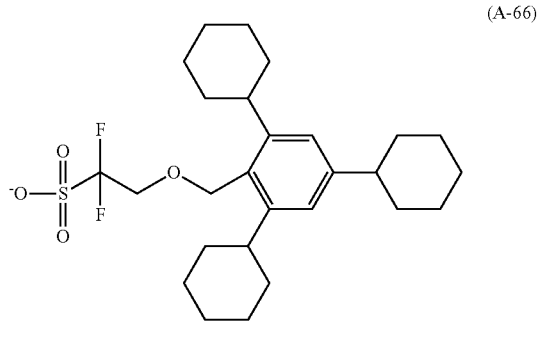
(A-67) 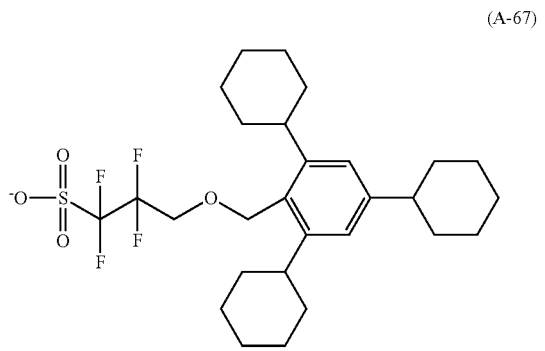
(A-68) 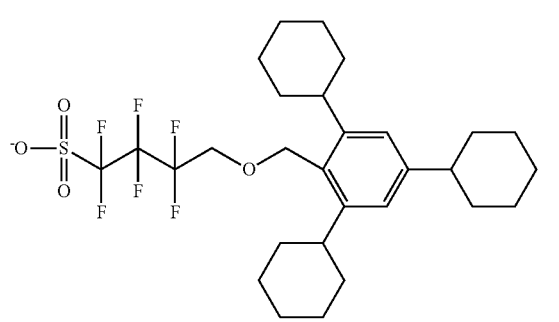

-continued
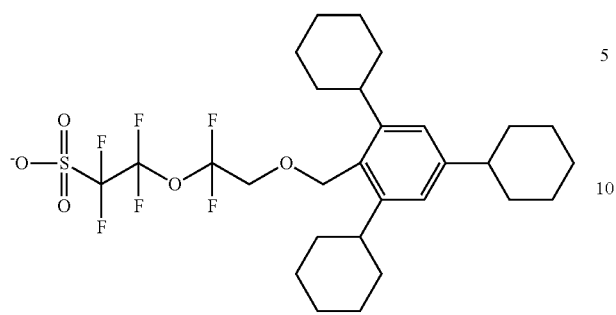
(A-69)
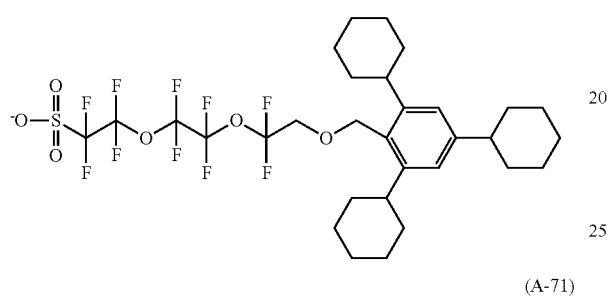
(A-70)
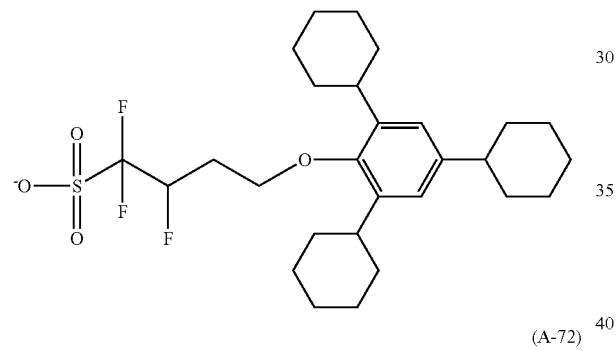
(A-71)
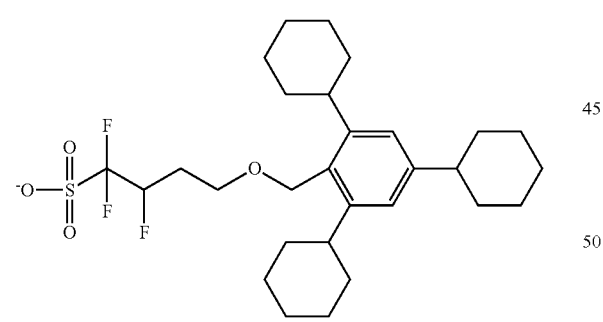
(A-72)
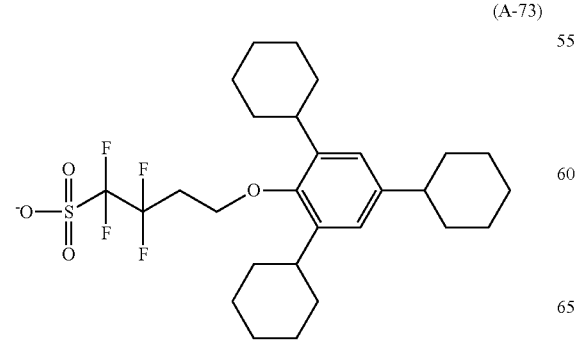
(A-73)
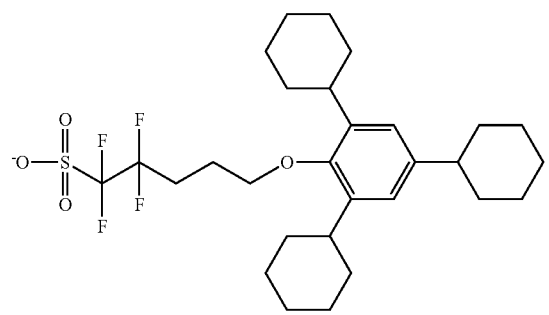
(A-74)
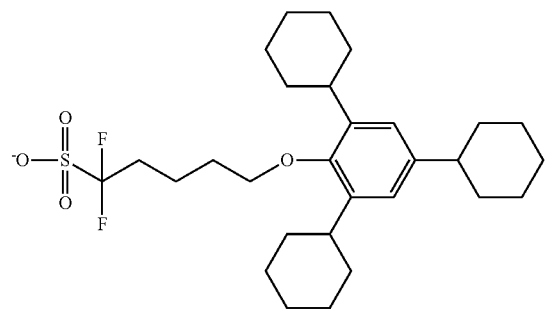
(A-75)
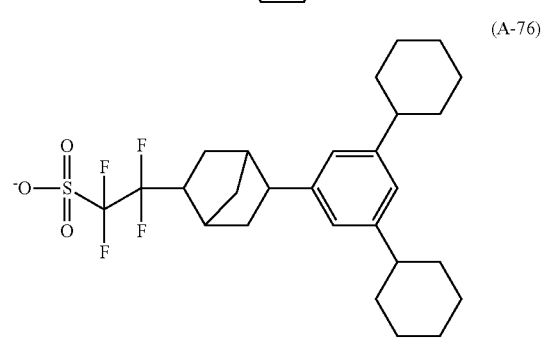
(A-76)
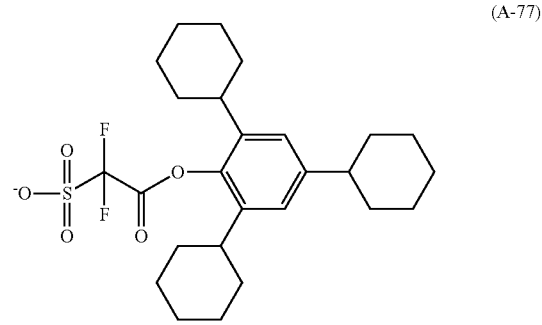
(A-77)
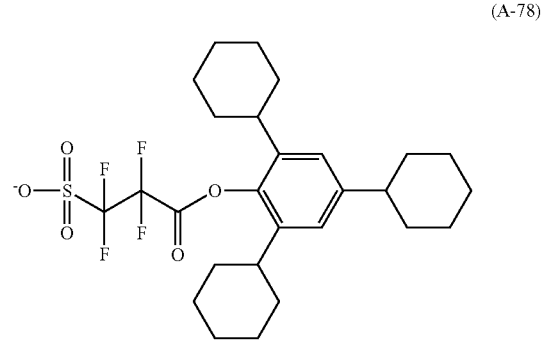
(A-78)

(A-79)
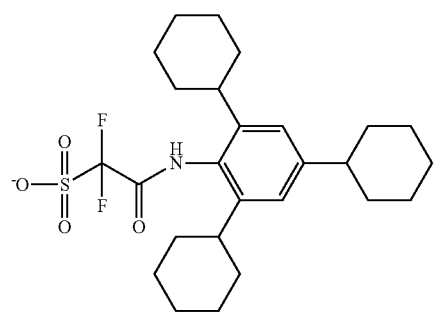
(A-80)
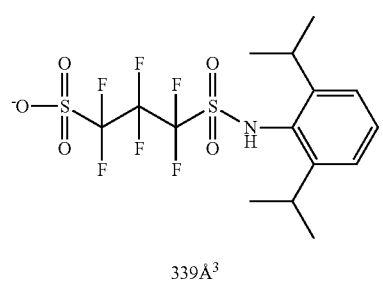
339Å³
(A-81)
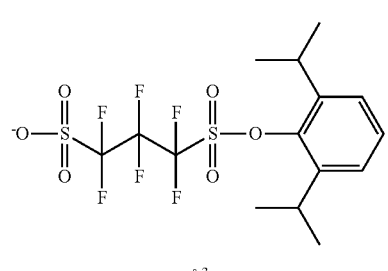
347Å³
(A-82)
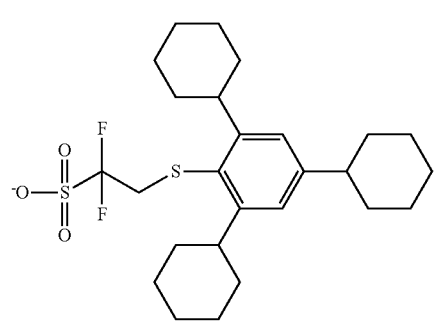
(A-83)
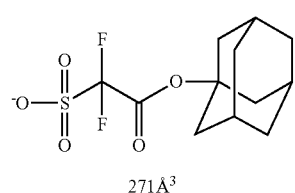
271Å³
(A-84)
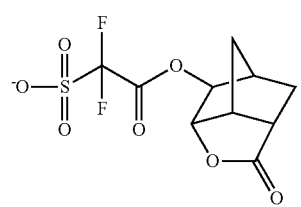
(A-85)
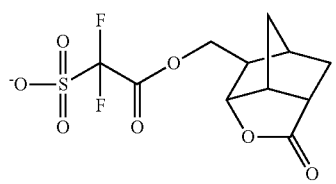
(A-86)
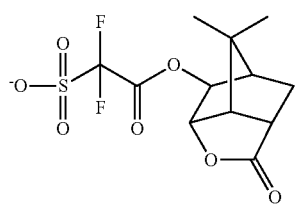
(A-87)
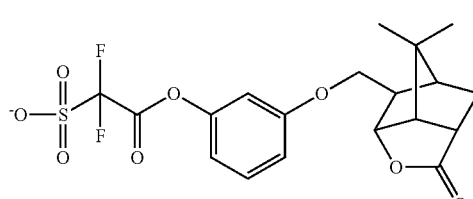
(A-88)
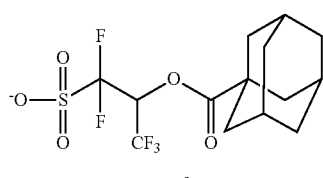
291Å³
(A-89)
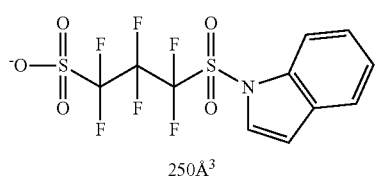
250Å³
(A-90)
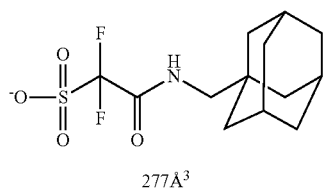
277Å³
(A-91)
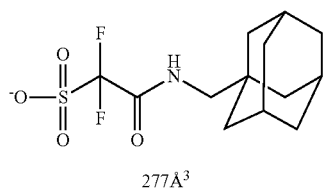
297Å³

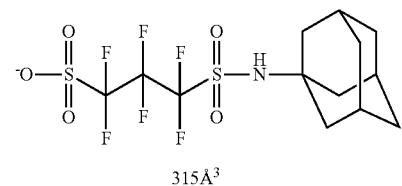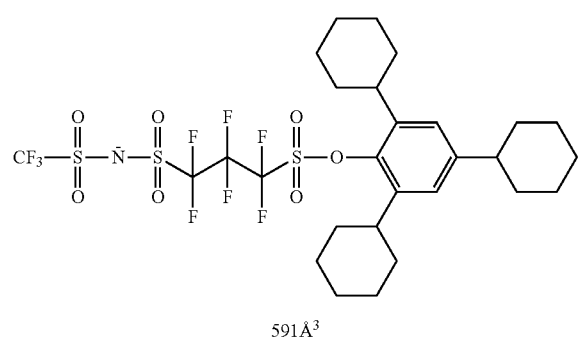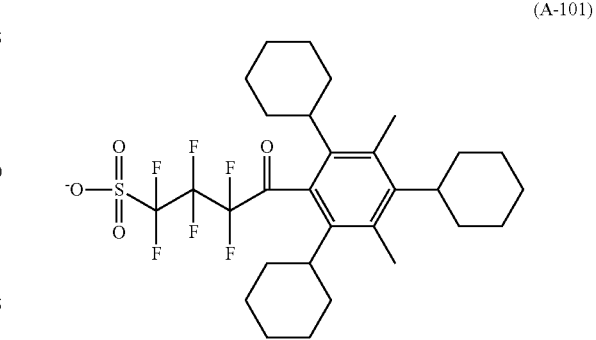

(A-102)
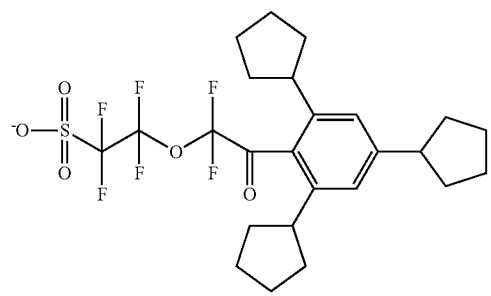
(A-103)
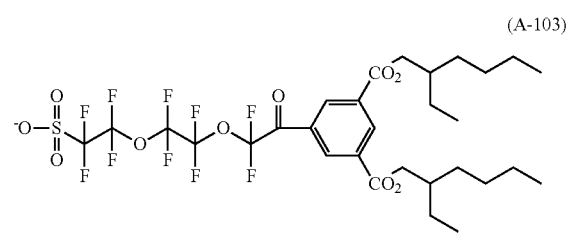
(A-104)
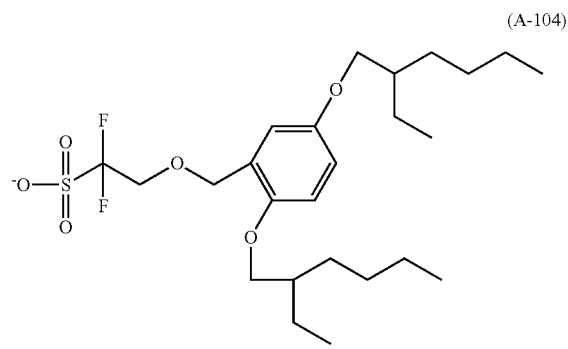
(A-105)
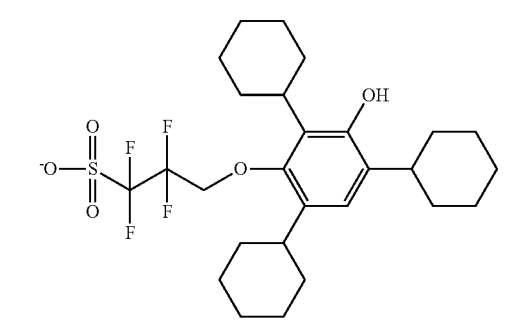
(A-106)
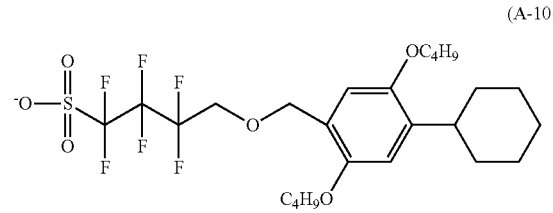
(A-107)
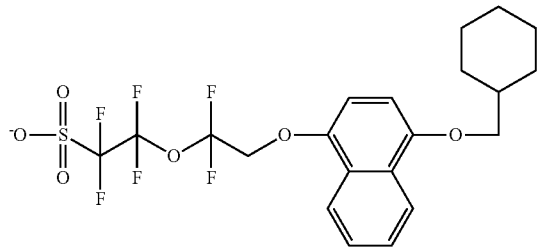
(A-108)
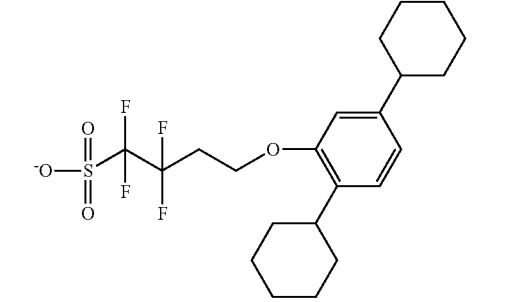
(A-109)
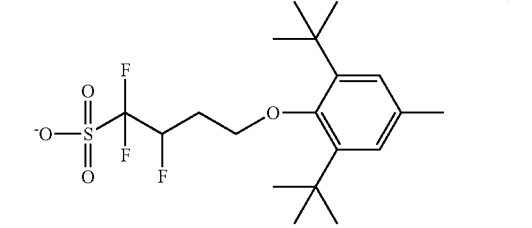
(A-110)
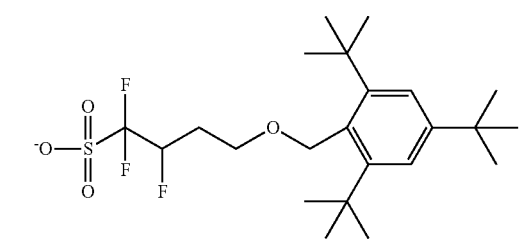
(A-111)
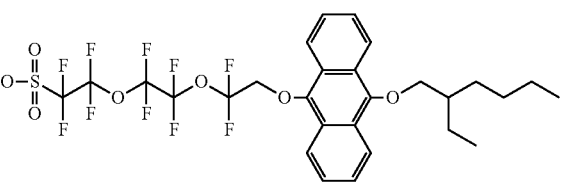
(A-112)
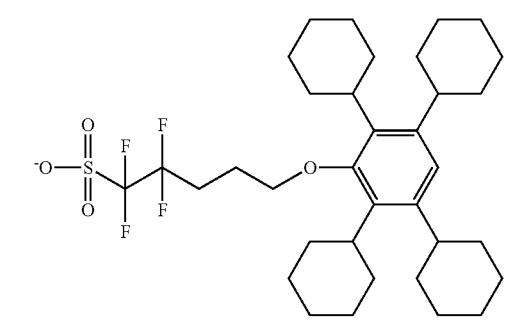

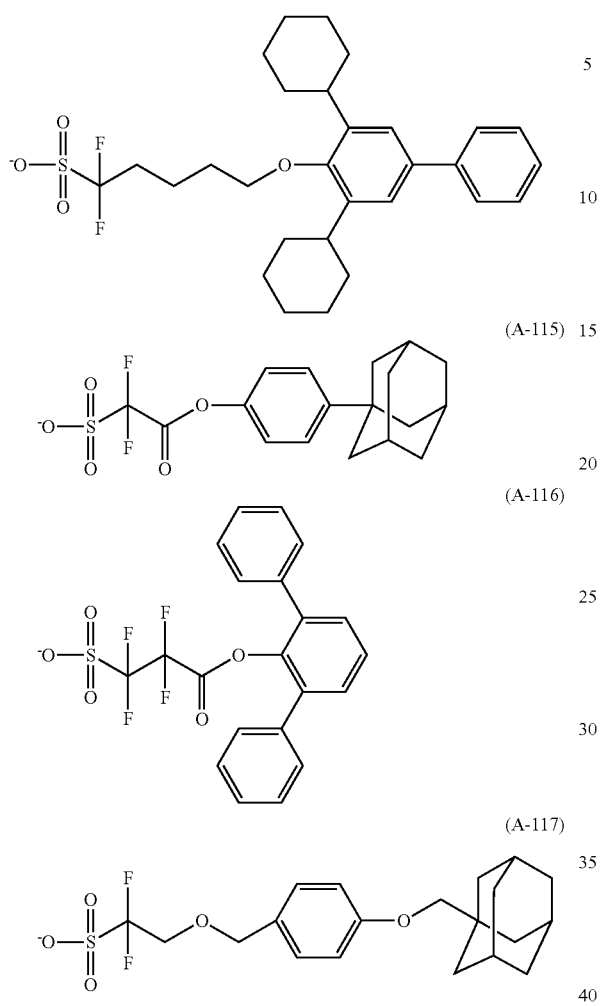

Particular examples of the photoacid generators (A1) (combinations of cation moiety and anion moiety) will be indicated in Table 2, which however in no way limit the present invention.

TABLE 2

| Photoacid generator (A1) | Anion | Cation |
| --- | --- | --- |
| A1-1 | (A-1) | (C-1) |
| A1-2 | (A-1) | (C-2) |
| A1-3 | (A-1) | (C-3) |
| A1-4 | (A-1) | (C-4) |
| A1-5 | (A-1) | (C-5) |
| A1-6 | (A-1) | (C-6) |
| A1-7 | (A-1) | (C-7) |
| A1-8 | (A-1) | (C-8) |
| A1-9 | (A-1) | (C-9) |
| A1-10 | (A-1) | (C-11) |
| A1-11 | (A-1) | (C-14) |
| A1-12 | (A-1) | (C-15) |
| A1-13 | (A-1) | (C-18) |
| A1-14 | (A-1) | (C-19) |
| A1-15 | (A-1) | (C-26) |
| A1-16 | (A-1) | (C-31) |
| A1-17 | (A-1) | (C-32) |
| A1-18 | (A-1) | (C-33) |
| A1-19 | (A-1) | (C-35) |
| A1-20 | (A-1) | (C-48) |
| A1-21 | (A-2) | (C-1) |
| A1-22 | (A-10) | (C-2) |
| A1-23 | (A-11) | (C-1) |
| A1-24 | (A-12) | (C-1) |
| A1-25 | (A-12) | (C-2) |
| A1-26 | (A-12) | (C-15) |
| A1-27 | (A-12) | (C-31) |
| A1-28 | (A-12) | (C-36) |
| A1-29 | (A-12) | (C-43) |
| A1-30 | (A-12) | (C-48) |
| A1-31 | (A-18) | (C-1) |
| A1-32 | (A-21) | (C-32) |
| A1-33 | (A-23) | (C-1) |
| A1-34 | (A-23) | (C-31) |
| A1-35 | (A-26) | (C-1) |
| A1-36 | (A-26) | (C-2) |
| A1-37 | (A-26) | (C-5) |
| A1-38 | (A-26) | (C-7) |
| A1-39 | (A-26) | (C-9) |
| A1-40 | (A-26) | (C-15) |
| A1-41 | (A-26) | (C-17) |
| A1-42 | (A-26) | (C-18) |
| A1-43 | (A-26) | (C-31) |
| A1-44 | (A-26) | (C-35) |
| A1-45 | (A-26) | (C-45) |
| A1-46 | (A-26) | (C-48) |
| A1-47 | (A-27) | (C-1) |
| A1-48 | (A-34) | (C-33) |
| A1-49 | (A-37) | (C-22) |
| A1-50 | (A-39) | (C-1) |
| A1-51 | (A-39) | (C-2) |
| A1-52 | (A-39) | (C-31) |
| A1-53 | (A-40) | (C-1) |
| A1-54 | (A-42) | (C-1) |
| A1-55 | (A-42) | (C-2) |
| A1-56 | (A-42) | (C-5) |
| A1-57 | (A-42) | (C-31) |
| A1-58 | (A-42) | (C-35) |
| A1-59 | (A-42) | (C-48) |
| A1-60 | (A-43) | (C-49) |
| A1-61 | (A-44) | (C-51) |
| A1-62 | (A-45) | (C-1) |
| A1-63 | (A-46) | (C-1) |
| A1-64 | (A-47) | (C-36) |
| A1-65 | (A-49) | (C-48) |
| A1-66 | (A-52) | (C-48) |
| A1-67 | (A-53) | (C-1) |
| A1-68 | (A-53) | (C-50) |
| A1-69 | (A-55) | (C-1) |
| A1-70 | (A-55) | (C-2) |
| A1-71 | (A-55) | (C-3) |
| A1-72 | (A-55) | (C-5) |
| A1-73 | (A-55) | (c-6) |
| A1-74 | (A-55) | (C-7) |
| A1-75 | (A-55) | (C-15) |
| A1-76 | (A-55) | (C-17) |
| A1-77 | (A-55) | (C-18) |
| A1-78 | (A-55) | (C-21) |
| A1-79 | (A-55) | (C-31) |
| A1-80 | (A-55) | (C-32) |
| A1-81 | (A-55) | (C-33) |
| A1-82 | (A-55) | (C-35) |
| A1-83 | (A-55) | (C-48) |
| A1-84 | (A-56) | (C-1) |
| A1-85 | (A-58) | (C-2) |
| A1-86 | (A-61) | (C-1) |
| A1-87 | (A-68) | (C-1) |
| A1-88 | (A-71) | (C-31) |
| A1-89 | (A-77) | (C-1) |
| A1-90 | (A-79) | (C-1) |
| A1-91 | (A-81) | (C-1) |
| A1-92 | (A-86) | (C-35) |
| A1-93 | (A-88) | (C-1) |
| A1-94 | (A-91) | (C-1) |

TABLE 2-continued

| Photoacid generator (A1) | Anion | Cation |
|---|---|---|
| A1-95 | (A-91) | (C-31) |
| A1-96 | (A-93) | (C-1) |
| A1-97 | (A-93) | (C-2) |
| A1-98 | (A-93) | (C-35) |
| A1-99 | (A-93) | (C-31) |
| A1-100 | (A-93) | (C-48) |
| A1-101 | (A-94) | (C-17) |
| A1-102 | (A-115) | (C-37) |

The photoacid generators (A1) may be used individually or in combination.

The content of photoacid generator(s) (A1) is preferably in the range of 0.1 to 30 mass %, more preferably 0.5 to 25 mass % and further more preferably 1 to 20 mass % based on the total solids of the composition of the present invention.

[Other Photoacid Generator]

In the present invention, other acid generators may be used in combination with the photoacid generator (A1). As such other photoacid generators usable in combination (hereinafter referred to as "photoacid generator (A2)" and the like), there can be mentioned a member appropriately selected from among a photoinitiator for photocationic polymerization, an initiator for photoradical polymerization, a photo-achromatic agent and photo-discoloring agent for dyes, any of heretofore known compounds that when exposed to actinic rays or radiation, generate an acid, employed in microresists, etc., and mixtures thereof. For example, there can be mentioned a diazonium salt, a phosphonium salt, a sulfonium salt, an iodonium salt, an imide sulfonate, an oxime sulfonate, diazosulfone, disulfone and o-nitrobenzyl sulfonate.

[2] Resin that when Acted on by an Acid, is Decomposed to Thereby Increase its Solubility in an Alkali Developer The positive actinic-ray- or radiation-sensitive resin composition of the present invention may contain a resin (B) that when acted on by an acid, is decomposed to thereby increase its solubility in an alkali developer. This resin (B) typically contains a group that is decomposed by the action of an acid to thereby generate an alkali soluble group (hereinafter also referred to as an acid-decomposable group). This resin may contain the acid-decomposable group in either its principal chain or side chain, or both thereof. The resin containing the acid-decomposable group in its side chain is preferred.

The acid-decomposable group is preferably a group resulting from substitution of the hydrogen atom of an alkali-soluble group, such as a —COOH group or an —OH group, with an acid-eliminable group. The acid-eliminable group is especially preferably an acetal group or a tertiary ester group.

As the matrix resin for bonding of the acid-decomposable group as a side chain, there can be mentioned, for example, an alkali-soluble resin having, in its side chain, an —OH or —COOH group. For example, there can be mentioned the alkali-soluble resins to be described hereinafter.

The alkali dissolution rate of the alkali-soluble resin as measured in a 0.261 N tetramethylammonium hydroxide (TMAH) (23° C.) is preferably 17 nm/sec or greater. The alkali dissolution rate is especially preferably 33 nm/sec or greater.

The alkali-soluble resins especially preferred from this viewpoint include alkali-soluble resins having hydroxystyrene structural units, such as o-, m- or p-poly(hydroxystyrene) and copolymers thereof, hydrogenated poly(hydroxystyrene), halogenated or alkylated poly(hydroxystyrene), poly(hydroxystyrene) having its part O-alkylated or O-acylated, styrene-hydroxystyrene copolymer, α-methylstyrene-hydroxystyrene copolymer and hydrogenated novolak resin and include alkali-soluble resins having carboxylated repeating units, such as those of (meth)acrylic acid and norbornene carboxylic acid.

As repeating units having an acid-decomposable group preferred in the present invention, there can be mentioned, for example, repeating units derived from t-butoxycarbonyloxystyrene, a 1-alkoxyethoxystyrene and a (meth)acrylic acid tertiary alkyl ester. As such, repeating units derived from a 2-alkyl-2-adamantyl (meth)acrylate and a dialkyl(1-adamantyl)methyl (meth)acrylate are more preferred.

The resin that when acted on by an acid, is decomposed to thereby increase its solubility in an alkali developer can be obtained by reaction of a precursor of acid-eliminable group with a resin or by copolymerization of an alkali-soluble resin monomer having an acid-eliminable group bonded thereto with various monomers, as disclosed in, for example, EP 254853 and JP-A's 2-25850, 3-223860 and 4-251259.

When the composition of the present invention is exposed to KrF excimer laser beams, electron beams, X-rays or high-energy light rays of 50 nm or less wavelength (EUV, etc.), it is preferred for the resin to have hydroxystyrene repeating units. More preferably, the resin is a copolymer of hydroxystyrene/hydroxystyrene protected by an acid-eliminable group or a copolymer of hydroxystyrene/(meth)acrylic acid tertiary alkyl ester.

In particular, the resin is preferably, for example, one having any of the repeating structures of general formula (A) below.

(A)

In the formula, each of $R_{01}$, $R_{02}$ and $R_{03}$ independently represents a hydrogen atom, an alkyl group, a cycloalkyl group, a halogen atom, a cyano group or an alkoxycarbonyl group.

$Ar^1$ represents, for example, an aromatic ring group. Alternatively, $R_{03}$ and $Ar_1$ may be simultaneously alkylene groups and bonded to each other so as to form a 5-membered or 6-membered ring in cooperation with —C—C—.

In the formula, each of n Y's independently represents a hydrogen atom or a group that is eliminated by the action of an acid, provided that at least one of the Y's is a group that is eliminated by the action of an acid.

In the formula, n is an integer of 1 to 4, preferably 1 or 2 and more preferably 1.

As alkyl groups represented by $R_{01}$ to $R_{03}$, there can be mentioned, for example, alkyl groups having up to 20 carbon atoms, such as a methyl group, an ethyl group, a propyl group, an isopropyl group, an n-butyl group, a sec-butyl group, a hexyl group, a 2-ethylhexyl group, an octyl group and a dodecyl group. Alkyl groups having up to 8 carbon atoms are more preferred. These alkyl groups may have a substituent.

The alkyl groups contained in the alkoxycarbonyl groups are preferably the same as the above-mentioned alkyl groups represented by $R_{01}$ to $R_{03}$.

The cycloalkyl groups may be monocyclic or polycyclic. As preferred examples thereof, there can be mentioned monocyclic alkyl groups having 3 to 8 carbon atoms, such as a cyclopropyl group, a cyclopentyl group and a cyclohexyl group. These cycloalkyl groups may have a substituent.

As the halogen atom, there can be mentioned a fluorine atom, a chlorine atom, a bromine atom or an iodine atom. A fluorine atom is preferred.

As preferred alkylene groups represented by $R_{03}$, there can be mentioned those having 1 to 8 carbon atoms, such as a methylene group, an ethylene group, a propylene group, a butylene group, a hexylene group and an octylene group.

The aromatic ring group represented by $Ar_1$ is preferably aromatic ring group having 6 to 14 carbon atoms. In particular, there can be mentioned a benzene ring, a toluene ring, a naphthalene ring or the like. These aromatic ring groups may have a substituent.

As the group (Y) that is eliminated by the action of an acid, there can be mentioned, for example, —C($R_{36}$)($R_{37}$)($R_{38}$), —C(=O)—O—C($R_{36}$)($R_{37}$)($R_{38}$), —C($R_{01}$)($R_{02}$)(O$R_{39}$), —C($R_{01}$)($R_{02}$)—C(=O)—O—C($R_{36}$)($R_{37}$)($R_{38}$), —CH($R_{36}$)(Ar) or the like.

In the formulae, each of $R_{36}$ to $R_{39}$ independently represents an alkyl group, a cycloalkyl group, an aryl group, an aralkyl group or an alkenyl group. $R_{36}$ and $R_{37}$ may be bonded with each other to thereby form a ring structure.

Each of $R_{01}$ and $R_{02}$ independently represents a hydrogen atom, an alkyl group, a cycloalkyl group, an aryl group, an aralkyl group or an alkenyl group.

Ar represents an aryl group.

The alkyl groups represented by $R_{36}$ to $R_{39}$ and $R_{01}$ and $R_{02}$ each preferably have 1 to 8 carbon atoms. For example, there can be mentioned a methyl group, an ethyl group, a propyl group, an n-butyl group, a sec-butyl group, a hexyl group, an octyl group and the like.

The cycloalkyl groups represented by $R_{36}$ to $R_{39}$ and $R_{01}$ and $R_{02}$ may be monocyclic or polycyclic. The monocyclic alkyl groups are preferably cycloalkyl groups having 3 to 8 carbon atoms. As such, there can be mentioned, for example, a cyclopropyl group, a cyclobutyl group, a cyclopentyl group, a cyclohexyl group, a cyclooctyl group and the like. The polycyclic alkyl groups are preferably cycloalkyl groups having 6 to 20 carbon atoms. As such, there can be mentioned, for example, an adamantyl group, a norbornyl group, an isobornyl group, a camphonyl group, a dicyclopentyl group, an α-pinel group, a tricyclodecanyl group, a tetracyclododecyl group, an androstanyl group and the like. With respect to these, the carbon atoms of each of the cycloalkyl groups may be partially substituted with a heteroatom, such as an oxygen atom.

The aryl groups represented by $R_{36}$ to $R_{39}$, $R_{01}$ and $R_{02}$ and Ar each preferably have 6 to 10 carbon atoms. For example, there can be mentioned a phenyl group, a naphthyl group, an anthryl group and the like.

The aralkyl groups represented by $R_{36}$ to $R_{39}$, $R_{01}$ and $R_{02}$ each preferably have 7 to 12 carbon atoms. For example, there can be mentioned a benzyl group, a phenethyl group, a naphthylmethyl group and the like.

The alkenyl groups represented by $R_{36}$ to $R_{39}$, $R_{01}$ and $R_{02}$ each preferably have 2 to 8 carbon atoms. For example, there can be mentioned a vinyl group, an allyl group, a butenyl group, a cyclohexenyl group and the like.

The ring formed by mutual bonding of $R_{36}$ and $R_{37}$ may be monocyclic or polycyclic. The monocyclic structure is preferably a cycloalkane structure having 3 to 8 carbon atoms. As such, there can be mentioned, for example, a cyclopropane structure, a cyclobutane structure, a cyclopentane structure, a cyclohexane structure, a cycloheptane structure, a cyclooctane structure or the like. The polycyclic structure is preferably a cycloalkane structure having 6 to 20 carbon atoms. As such, there can be mentioned, for example, an adamantane structure, a norbornane structure, a dicyclopentane structure, a tricyclodecane structure, a tetracyclododecane structure or the like. With respect to these, the carbon atoms of each of the ring structure may be partially substituted with a heteroatom, such as an oxygen atom.

Each of the groups may have a substituent. As the substituent, there can be mentioned, for example, an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, a nitro group or the like. Preferably, the number of carbon atoms of each of the substituents is up to 8.

The group (Y) that is eliminated by the action of an acid more preferably has any of the structures of general formula (B) below.

(B)

In the formula, each of $L_1$ and $L_2$ independently represents a hydrogen atom, an alkyl group, a cycloalkyl group, an aryl group or an aralkyl group.

M represents a single bond or a bivalent connecting group.

Q represents an alkyl group, a cycloalkyl group, an alicyclic group, a aromatic ring group, an amino group, an ammonium group, a mercapto group, a cyano group or an aldehyde group. The alicyclic group and the aromatic ring group may contain a heteroatom.

At least two of Q, M and $L_1$ may be bonded to each other to thereby form a 5-membered or 6-membered ring.

The alkyl groups represented by $L_1$ and $L_2$ are, for example, alkyl groups having 1 to 8 carbon atoms. As preferred examples thereof, there can be mentioned a methyl group, an ethyl group, a propyl group, an n-butyl group, a sec-butyl group, a hexyl group and an octyl group.

The cycloalkyl groups represented by $L_1$ and $L_2$ are, for example, cycloalkyl groups having 3 to 15 carbon atoms. As preferred examples thereof, there can be mentioned a cyclopentyl group, a cyclohexyl group, a norbornyl group and an adamantyl group.

The aryl groups represented by $L_1$ and $L_2$ are, for example, aryl groups having 6 to 15 carbon atoms. As preferred examples thereof, there can be mentioned a phenyl group, a tolyl group, a naphthyl group, an anthryl group and the like.

The aralkyl groups represented by $L_1$ and $L_2$ are, for example, those having 6 to 20 carbon atoms. There can be mentioned a benzyl group, a phenethyl group and the like.

The bivalent connecting group represented by M is, for example, an alkylene group (e.g., a methylene group, an ethylene group, a propylene group, a butylene group, a hexylene group, an octylene group, etc.), a cycloalkylene group (e.g., a cyclopentylene group, a cyclohexylene group, etc.), an alkenylene group (e.g., an ethylene group, a propenylene group, a butenylene group, etc.), an arylene group (e.g., a phenylene group, a tolylene group, a naphthylene group, etc.), —S—, —O—, —CO—, —SO$_2$—, —N($R_0$)— or a bivalent connecting group resulting from a combination of two or more of these groups. $R_0$ represents a hydrogen atom or an alkyl group. The alkyl group represented by $R_0$ is, for example, an alkyl group having 1 to 8 carbon atoms; in particular, there can be mentioned a methyl group, an ethyl group, a propyl group, an n-butyl group, a sec-butyl group, a hexyl group, an octyl group and the like.

The alkyl group and cycloalkyl group represented by Q are the same as those mentioned above as $L_1$ and $L_2$.

As the alicyclic group and aromatic ring group represented by Q, there can be mentioned, for example, the cycloalkyl group and aryl group mentioned above as $L_1$ and $L_2$. Preferably, each of the alicyclic group and aromatic ring group has 3 to 15 carbon atoms.

As the alicyclic group containing a heteroatom and aromatic ring group containing a heteroatom represented by Q, there can be mentioned, for example, groups having a heterocyclic structure, such as thiirane, cyclothiorane, thiophene, furan, pyrrole, benzothiophene, benzofuran, benzopyrrole, triazine, imidazole, benzimidazole, triazole, thiadiazole, triazole and pyrrolidone. However, the alicyclic groups and aromatic ring groups are not limited to these as long as the ring is formed by carbon and a heteroatom or by heteroatoms.

As the ring structure, that may be formed by mutual bonding of at least two of Q, M and $L_1$, there can be mentioned the 5-membered or 6-membered ring resulting from mutual bonding of at least two of Q, M and $L_1$ so as to form, for example, a propylene group or a butylene group and subsequent formation of a ring containing an oxygen atom.

In general formula (B), each of the groups represented by $L_1$, $L_2$, M and Q may have a substituent. As the substituent, there can be mentioned, for example, an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, a nitro group and the like. Preferably, the number of carbon atoms of each of the substituents is up to 8.

The groups of the formula -M-Q are preferably groups having 1 to 30 carbon atoms, more preferably groups having 5 to 20 carbon atoms. From the viewpoint of outgas suppression, it is especially preferred for the number of carbon atoms to be 6 or greater.

As preferred other resins, there can be mentioned the resin containing a repeating unit of general formula (X) below.

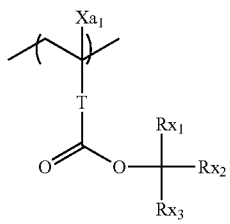
(X)

In general formula (X), $Xa_1$ represents a hydrogen atom, a methyl group, a trifluoromethyl group or a hydroxymethyl group.

T represents a single bond or a bivalent connecting group.

Each of $Rx_1$ to $Rx_3$ independently represents a linear or branched alkyl group or a monocyclic or polycyclic alkyl group. At least two of $Rx_1$ to $Rx_3$ may be bonded to each other to thereby form a monocyclic or polycyclic alkyl group.

As the bivalent connecting group represented by T, there can be mentioned, for example, an alkylene group, a group of the formula —COO-Rt-, a group of the formula —O-Rt- and the like. In the formulae, Rt represents an alkylene group or a cycloalkylene group.

T is preferably a single bond or a group of the formula —COO-Rt-. Rt is preferably an alkylene group having 1 to 5 carbon atoms, more preferably a —$CH_2$— group or —$(CH_2)_3$— group.

The alkyl group represented by each of $Rx_1$ to $Rx_3$ is preferably one having 1 to 4 carbon atoms, such as a methyl group, an ethyl group, an n-propyl group, an isopropyl group, an n-butyl group, an isobutyl group or a t-butyl group.

The cycloalkyl group represented by each of $Rx_1$ to $Rx_3$ is preferably a monocyclic alkyl group, such as a cyclopentyl group or a cyclohexyl group, or a polycyclic alkyl group, such as a norbornyl group, a tetracyclodecanyl group, a tetracyclododecanyl group or an adamantyl group.

The cycloalkyl group formed by bonding of at least two of $Rx_1$ to $Rx_3$ is preferably a monocyclic alkyl group, such as a cyclopentyl group or a cyclohexyl group, or a polycyclic alkyl group, such as a norbornyl group, a tetracyclodecanyl group, a tetracyclododecanyl group or an adamantyl group.

In a preferred mode, $Rx_1$ is a methyl group or an ethyl group, and $Rx_2$ and $Rx_3$ are bonded to each other to thereby form any of the above-mentioned cycloalkyl groups.

Specific examples of the repeating units of general formula (X) will be shown below, which however in no way limit the scope of the present invention.

In the following formulae, Rx represents H, $CH_3$, $CF_3$ or $CH_2OH$. Each of Rxa and Rxb independently represents an alkyl group having 1 to 4 carbon atoms.

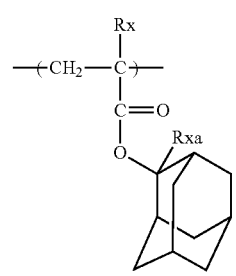

1

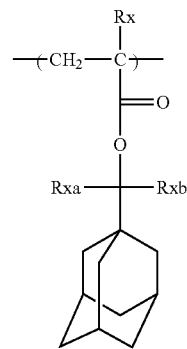

2

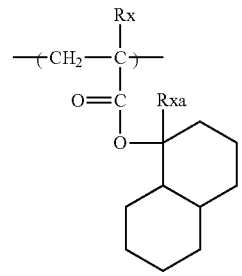

3

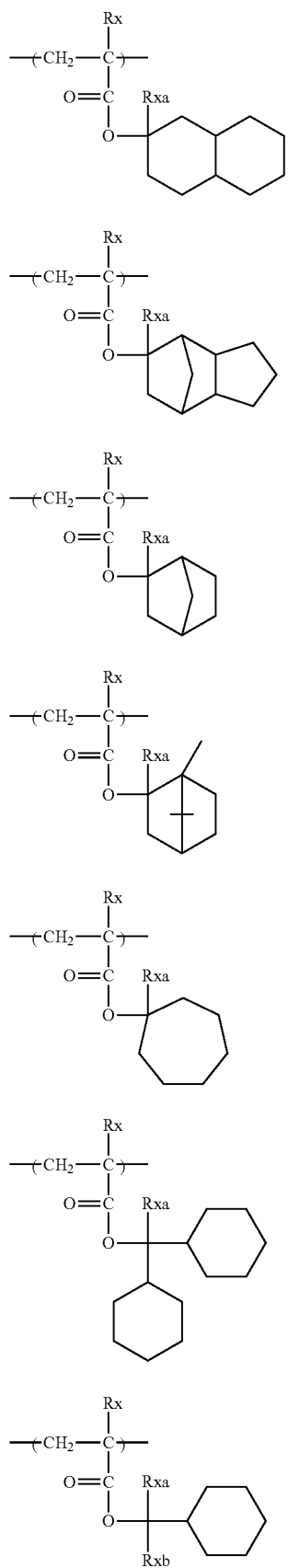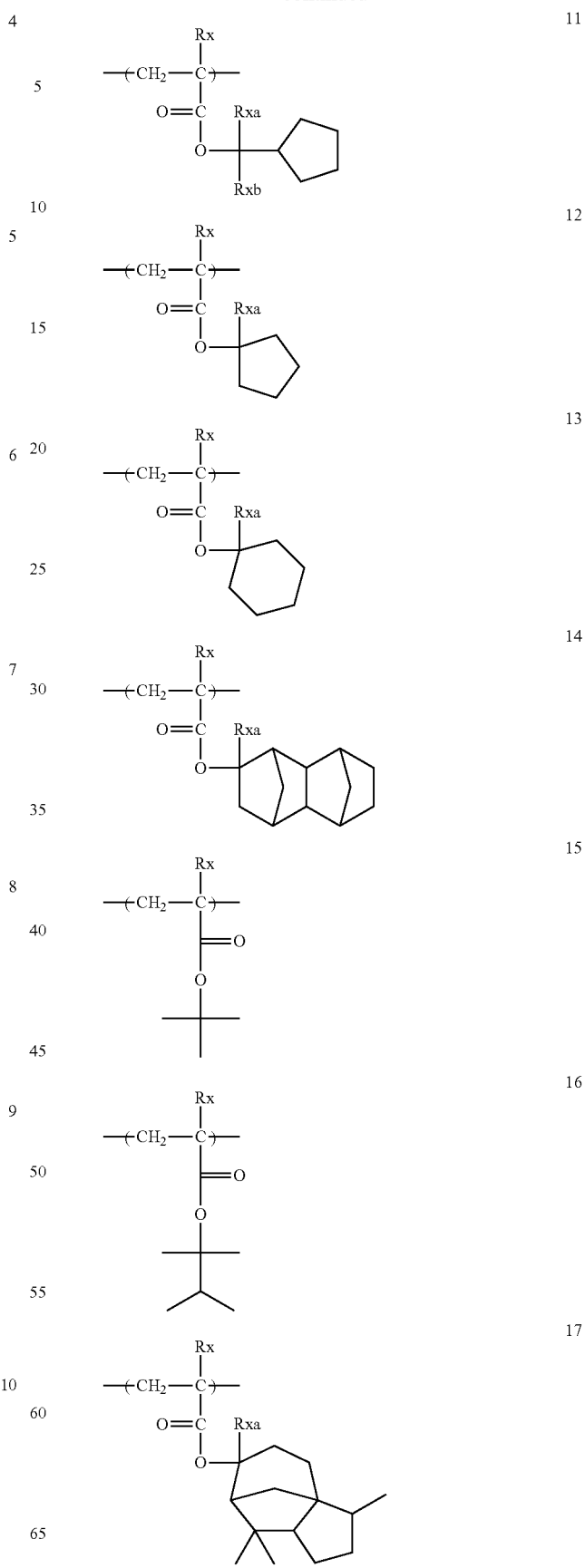

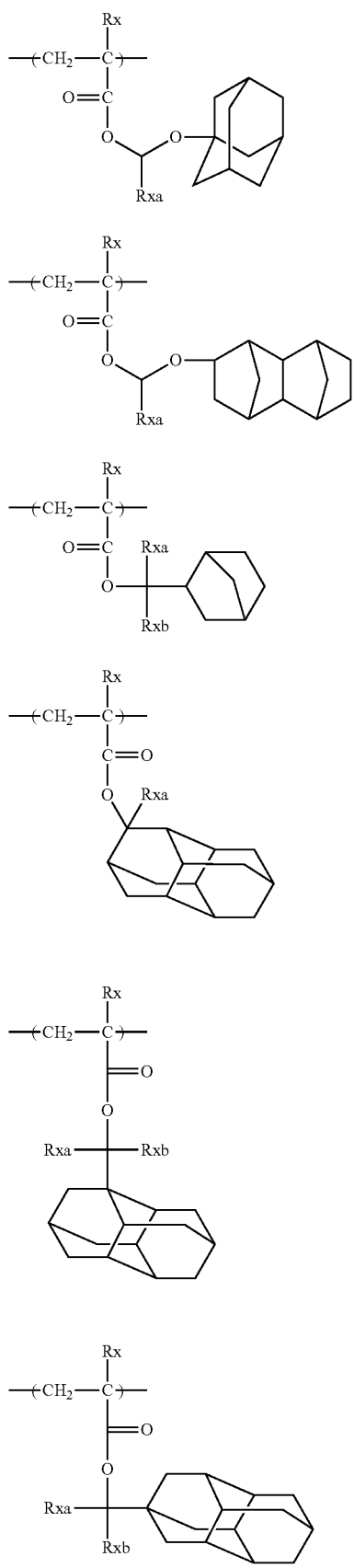

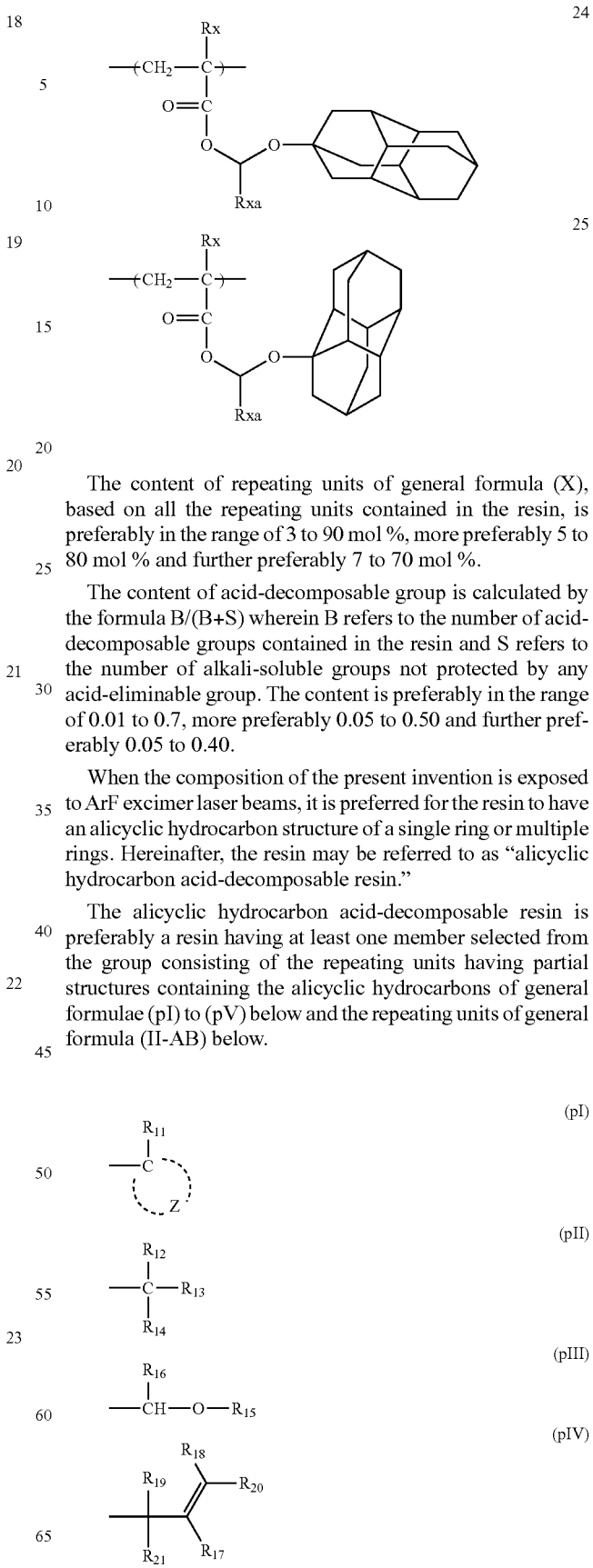

The content of repeating units of general formula (X), based on all the repeating units contained in the resin, is preferably in the range of 3 to 90 mol %, more preferably 5 to 80 mol % and further preferably 7 to 70 mol %.

The content of acid-decomposable group is calculated by the formula B/(B+S) wherein B refers to the number of acid-decomposable groups contained in the resin and S refers to the number of alkali-soluble groups not protected by any acid-eliminable group. The content is preferably in the range of 0.01 to 0.7, more preferably 0.05 to 0.50 and further preferably 0.05 to 0.40.

When the composition of the present invention is exposed to ArF excimer laser beams, it is preferred for the resin to have an alicyclic hydrocarbon structure of a single ring or multiple rings. Hereinafter, the resin may be referred to as "alicyclic hydrocarbon acid-decomposable resin."

The alicyclic hydrocarbon acid-decomposable resin is preferably a resin having at least one member selected from the group consisting of the repeating units having partial structures containing the alicyclic hydrocarbons of general formulae (pI) to (pV) below and the repeating units of general formula (II-AB) below.

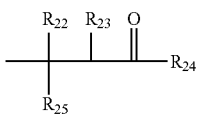 (pV)

In general formulae (pI) to (pV), $R_{11}$ represents a methyl group, an ethyl group, an n-propyl group, an isopropyl group, an n-butyl group, an isobutyl group or a sec-butyl group, and Z represents an atomic group required for formation of a cycloalkyl group in cooperation with a carbon atom.

Each of $R_{12}$ to $R_{16}$ independently represents a linear or branched alkyl group having 1 to 4 carbon atoms or a cycloalkyl group, provided that at least one of $R_{12}$ to $R_{14}$ represents a cycloalkyl group and at least either $R_{15}$ or $R_{16}$ represents a cycloalkyl group.

Each of $R_{17}$ to $R_{21}$ independently represents a hydrogen atom or a cycloalkyl group or a linear or branched alkyl group having 1 to 4 carbon atoms, provided that at least one of $R_{17}$ to $R_{21}$ represents a cycloalkyl group and at least either $R_{19}$ or $R_{21}$ represents a cycloalkyl group or a linear or branched alkyl group having 1 to 4 carbon atoms.

Each of $R_{22}$ to $R_{25}$ independently represents a hydrogen atom or a cycloalkyl group or a linear or branched alkyl group having 1 to 4 carbon atoms, provided that at least one of $R_{22}$ to $R_{25}$ represents a cycloalkyl group. $R_{23}$ and $R_{24}$ may be bonded to each other to thereby form a ring.

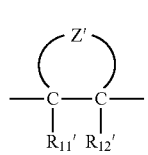 (II-AB)

In general formula (II-AB), each of $R_{11'}$ and $R_{12'}$ independently represents a hydrogen atom, a cyano group, a halogen atom or an alkyl group.

Z' represents an atomic group for formation of an alicyclic structure in cooperation with two bonded carbon atoms (C—C).

Further preferably, general formula (II-AB) is either general formula (II-AB1) or general formula (II-AB2) below.

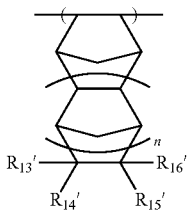 (II-AB1)

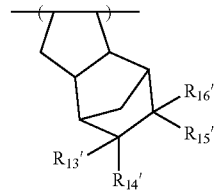 (II-AB2)

In general formulae (II-AB1) and (II-AB2), each of $R_{13'}$ to $R_{16'}$ independently represents a hydrogen atom, a halogen atom, a cyano group, a hydroxyl group, —COOH, —COOR$_5$, a group that is decomposed by the action of an acid, —C(=O)—X-A'—R$_{17'}$, an alkyl group or a cycloalkyl group. In the above formula, $R_5$ represents an alkyl group, a cycloalkyl group or a group with a lactone structure. X represents an oxygen atom, a sulfur atom, —NH—, —NHSO$_2$— or —NHSO$_2$NH—. A' represents a single bond or a bivalent connecting group. $R_{17'}$ represents —COOH, —COOR$_5$, —CN, a hydroxyl group, an alkoxy group, —CO—NH—R$_6$, —CO—NH—SO$_2$—R$_6$ or a group with a lactone structure. $R_6$ represents an alkyl group or a cycloalkyl group. At least two of $R_{13'}$ to $R_{16'}$ may be bonded to each other to thereby form a ring.

n is 0 or 1.

In general formulae (pI) to (pV), each of the alkyl groups represented by $R_{12}$ to $R_{25}$ is preferably a linear or branched alkyl group having 1 to 4 carbon atoms. As such, there can be mentioned, for example, a methyl group, an ethyl group, a propyl group, an n-butyl group, a sec-butyl group, a t-butyl group and the like.

The cycloalkyl groups represented by $R_{12}$ to $R_{25}$ and the cycloalkyl group formed by Z and a carbon atom may be monocyclic or polycyclic. In particular, there can be mentioned groups of a monocyclo, bicyclo, tricyclo or tetracyclo structure or the like having 5 or more carbon atoms. The number of carbon atoms thereof is preferably in the range of 6 to 30, especially preferably 7 to 25.

As preferred cycloalkyl groups, there can be mentioned an adamantyl group, a noradamantyl group, a decalin residue, a tricyclodecanyl group, a tetracyclododecanyl group, a norbornyl group, a cedrol group, a cyclopentyl group, a cyclohexyl group, a cycloheptyl group, a cyclooctyl group, a cyclodecanyl group and a cyclododecanyl group. As more preferred cycloalkyl groups, there can be mentioned an adamantyl group, a norbornyl group, a cyclohexyl group, a cyclopentyl group, a tetracyclododecanyl group and a tricyclodecanyl group.

These alkyl groups and cycloalkyl groups may further have substituents. As substituents, there can be mentioned an alkyl group (1 to 4 carbon atoms), a halogen atom, a hydroxyl group, an alkoxy group (1 to 4 carbon atoms), a carboxyl group and an alkoxycarbonyl group (2 to 6 carbon atoms). These substituents may further have substituents. As substituents that can be further introduced in the alkyl groups, alkoxy groups, alkoxycarbonyl groups, etc., there can be mentioned a hydroxyl group, a halogen atom and an alkoxy group.

The structures of the general formulae (pI) to (pV) can be used for the protection of the alkali-soluble groups. As the alkali-soluble groups, there can be mentioned various groups generally known in this technical field.

In particular, there can be mentioned, for example, structures resulting from replacement of a hydrogen atom of a carboxylic acid group, sulfonic acid group, phenol group or thiol group with any of the structures of the general formulae (pI) to (pV). Structures resulting from replacement of a hydrogen atom of a carboxylic acid group or sulfonic acid group with any of the structures of the general formulae (pI) to (pV) are preferred.

As preferred repeating units having any of the alkali-soluble groups protected by the structures of the general formulae (pI) to (pV), there can be mentioned those of general formula (pA) below.

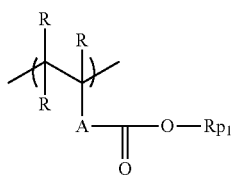
(pA)

In general formula (pA), R represents a hydrogen atom, a halogen atom or a linear or branched alkyl group having 1 to 4 carbon atoms. Two or more R's may be identical to or different from each other.

A represents any one or a combination of two or more groups selected from the group consisting of a single bond, an alkylene group, an ether group, a thioether group, a carbonyl group, an ester group, an amido group, a sulfonamido group, a urethane group and a urea group. A single bond is preferred.

Pp1 represents any of the groups of the above general formulae (pI) to (pV).

The repeating units of the general formula (pA) are most preferably those derived from a 2-alkyl-2-adamantyl(meth)acrylate and a dialkyl(1-adamantyl)methyl(meth)acrylate.

Specific examples of the repeating units of the general formula (pA) will be shown below.

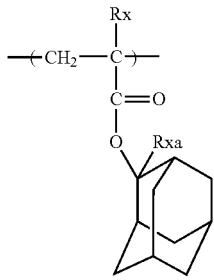
1

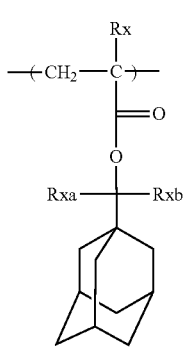
2

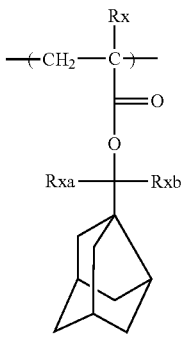
3

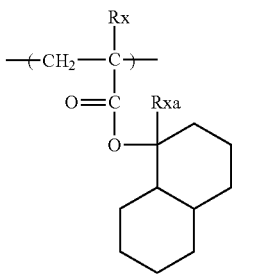
4

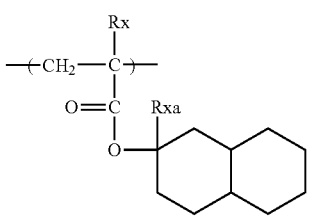
5

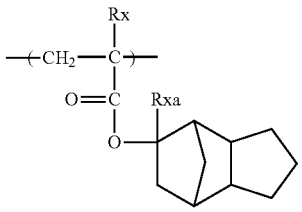
6

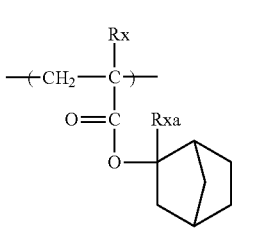
7

8

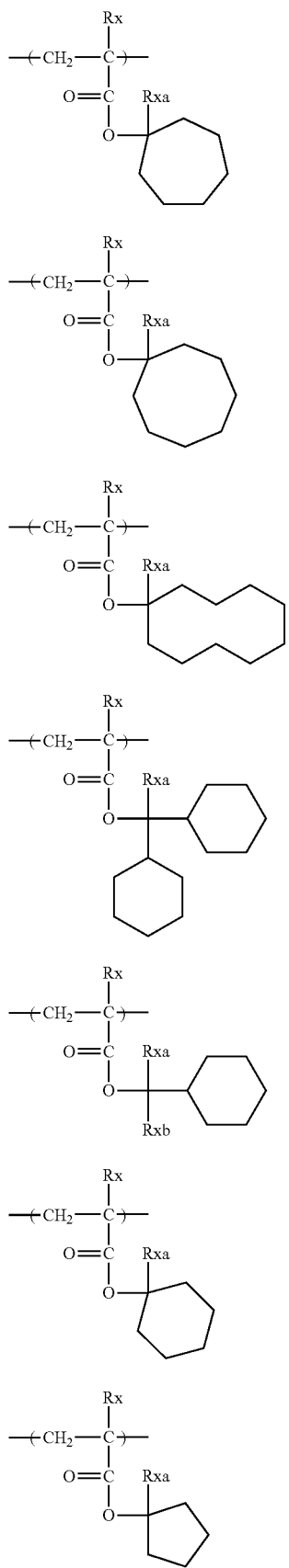

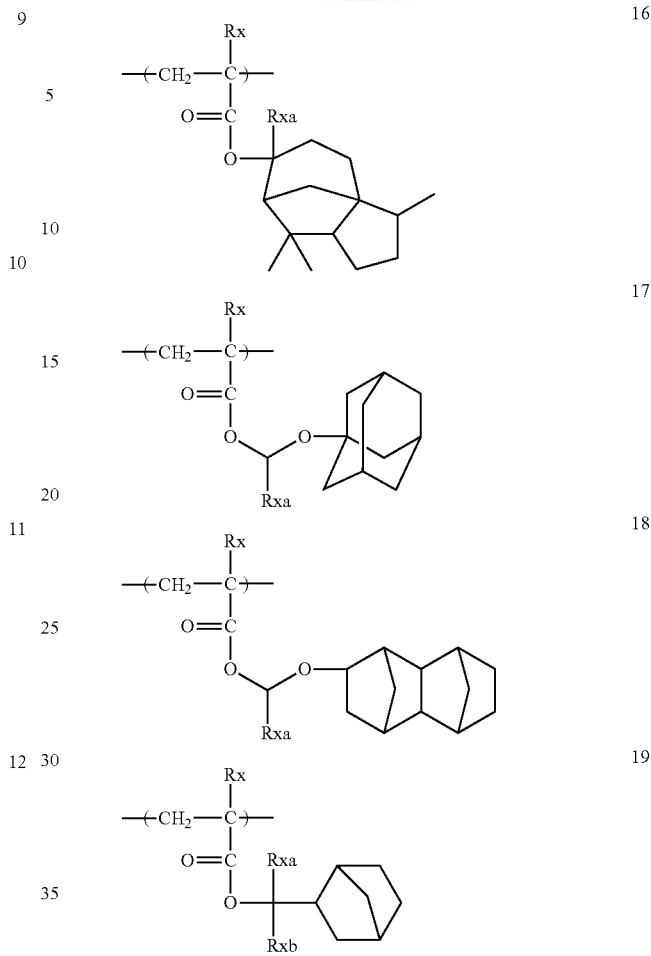

In the above structural formulae, Rx represents H, $CH_3$, $CF_3$ or $CH_2OH$. Each of Rxa and Rxb independently represents an alkyl group having 1 to 4 carbon atoms.

In the general formula (II-AB), the halogen atoms represented by $R_{11'}$ and $R_{12'}$ include a chlorine atom, a bromine atom, a fluorine atom, an iodine atom, etc.

The alkyl groups represented by $R_{11'}$ and $R_{12'}$ are preferably linear or branched alkyl groups each having 1 to 10 carbon atoms. For example, there can be mentioned a methyl group, an ethyl group, an n-propyl group, an isopropyl group, a linear or branched butyl, pentyl, hexyl or heptyl group, and the like.

The atomic group represented by Z' is one capable of providing the resin with a repeating unit of optionally substituted alicyclic hydrocarbon. The atomic group is preferably one capable of providing a bridged alicyclic structure for formation of a bridged alicyclic hydrocarbon repeating unit.

The provided alicyclic hydrocarbon skeleton can be the same as that of the cycloalkyl groups represented by $R_{12}$ to $R_{25}$ in the general formulae (pII) to (pV).

The alicyclic hydrocarbon skeleton may have a substituent. As the substituent, there can be mentioned any of the atoms or groups represented by $R_{13'}$ to $R_{16'}$ in the general formulae (II-AB1) and (II-AB2).

In the alicyclic hydrocarbon acid-decomposable resin, at least one repeating unit selected from among the repeating units having partial structures containing the alicyclic hydrocarbons of general formulae (pI) to (pV), the repeating units of general formula (II-AB) and the repeating units of copolymer components to be described below may contain the group that is decomposed by the action of an acid.

Any of the various substituents that can be introduced in $R_{13'}$ to $R_{16'}$ in general formulae (II-AB1) and (II-AB2) can be a substituent for the atomic groups Z' for formation of the alicyclic structures or the bridged alicyclic structures of general formula (II-AB).

Specific examples of the repeating units of general formulae (II-AB1) and (II-AB2) will be shown below, which however in no way limit the scope of the present invention.

[II-1]
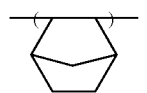

[II-2]
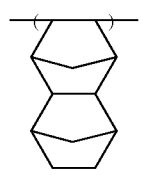

[II-3]
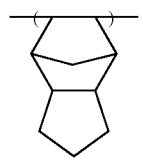

[II-4]
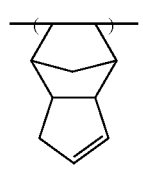

[II-5]
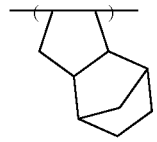

[II-6]
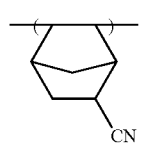

[II-7]
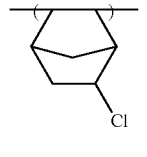

[II-8]
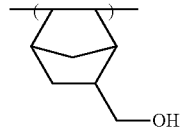

-continued

[II-9]
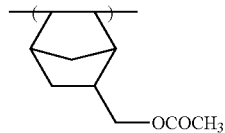

[II-10]
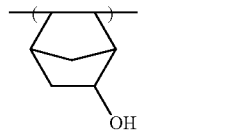

[II-11]
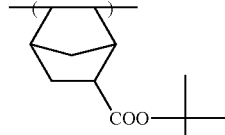

[II-12]
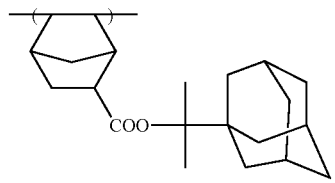

[II-13]
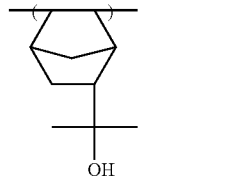

[II-14]
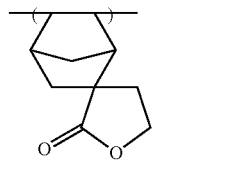

[II-15]
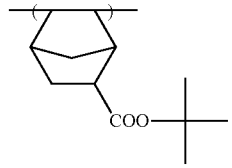

[II-16]
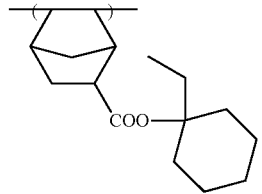

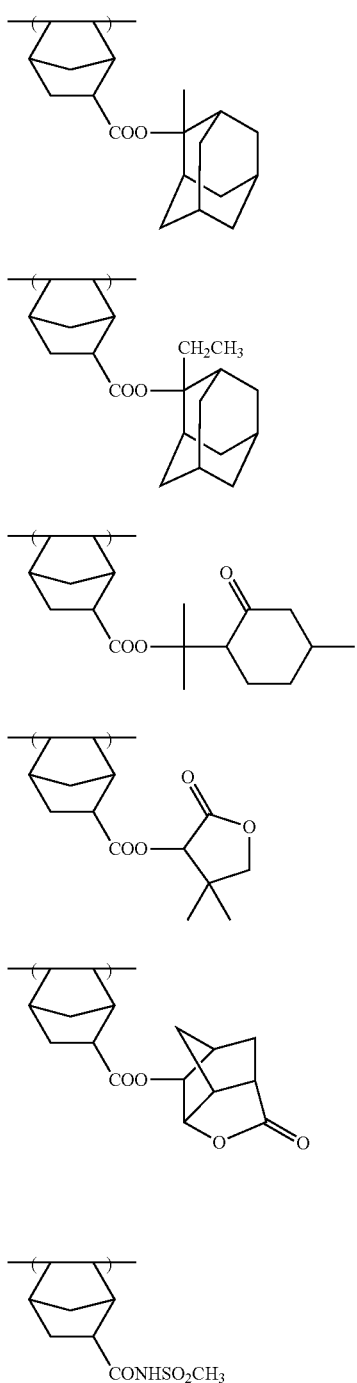
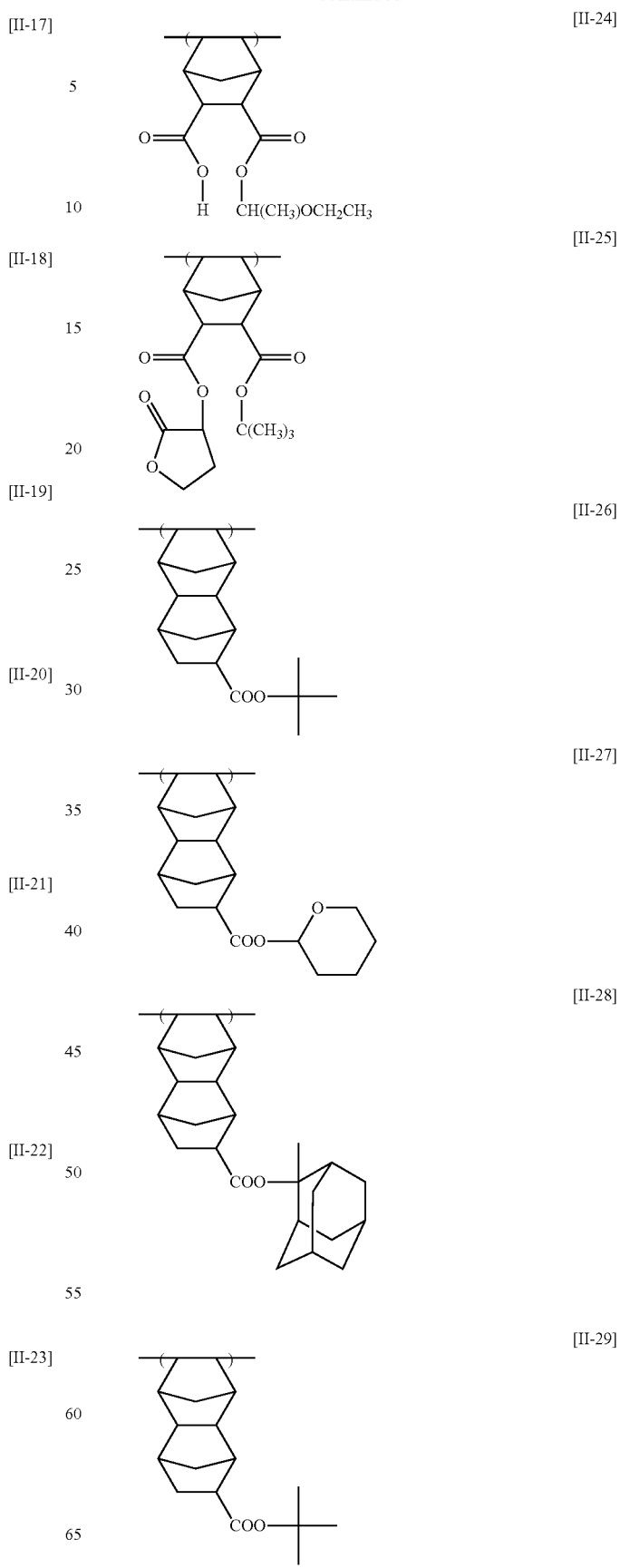

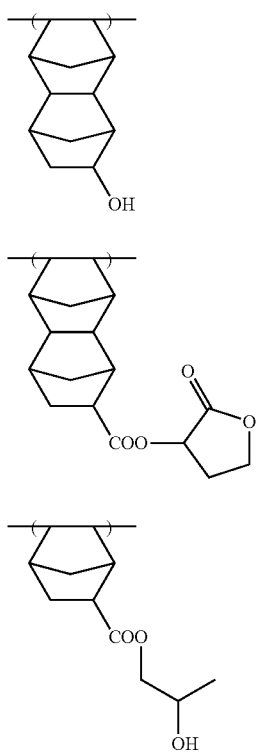

[II-30]

[II-31]

[II-32]

It is preferred for the alicyclic hydrocarbon acid-decomposable resin to contain a repeating unit containing a lactone group. The lactone group is preferably a group having a 5- to 7-membered ring lactone structure, more preferably one in which a 5- to 7-membered ring lactone structure is condensed with another cyclic structure in a fashion to form a bicyclo structure or spiro structure.

This alicyclic hydrocarbon acid-decomposable resin further more preferably contains a repeating unit containing a group with any of the lactone structures of general formulae (LC1-1) to (LC1-17) below. The groups with lactone structures may be directly bonded to the principal chain of the resin. Preferred lactone structures are those of formulae (LC1-1), (LC1-4), (LC1-5), (LC1-6), (LC1-13), (LC1-14) and (LC1-17). Using these specified lactone structures enhances the line edge roughness and development defect reduction.

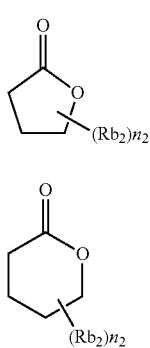

LC1-1

LC1-2

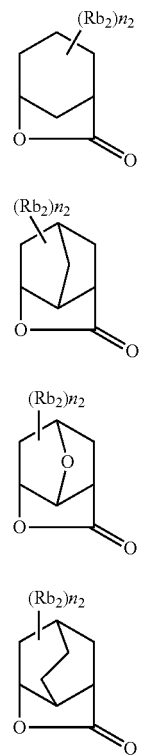

LC1-3

LC1-4

LC1-5

LC1-6

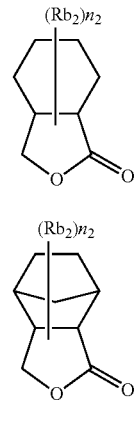

LC1-7

LC1-8

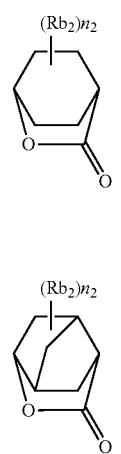

LC1-9

LC1-10

LC1-11
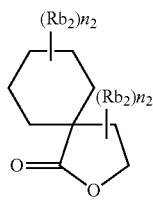

LC1-12
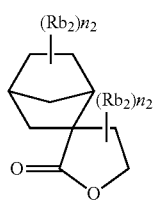

LC1-13
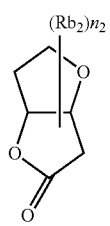

LC1-14
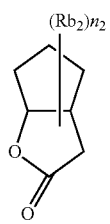

LC1-15
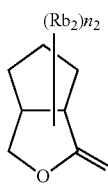

LC1-16
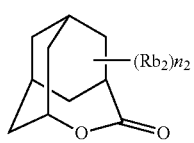

LC1-17
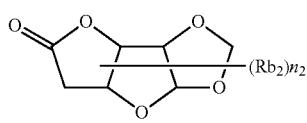

The presence of a substituent ($Rb_2$) on the portion of the lactone structure is optional. As preferred substituents ($Rb_2$), there can be mentioned, for example, an alkyl group having 1 to 8 carbon atoms, a cycloalkyl group having 3 to 7 carbon atoms, an alkoxy group having 1 to 8 carbon atoms, an alkoxycarbonyl group having 1 to 8 carbon atoms, a carboxyl group, a halogen atom, a hydroxyl group, a cyano group, an acid-decomposable group and the like.

In the formulae, $n_2$ is an integer of 0 to 4. When $n_2$ is an integer of 2 or greater, the plurality of present substituents ($Rb_2$) may be identical to or different from each other. Further, the plurality of present substituents ($Rb_2$) may be bonded to each other to thereby form a ring structure.

As the repeating units having the groups with lactone structures of any of general formulae (LC1-1) to (LC1-17), there can be mentioned the repeating units of general formulae (II-AB1) and (II-AB2) wherein at least one of R13' to R16' has any of the groups of the general formulae (LC1-1) to (LC1-17) as well as the repeating units of general formula (AI) below. As specific examples of first case, there can be mentioned the structure in which the $R_5$ of —$COOR_5$ represents any of the groups of general formulae (LC1-1) to (LC1-17)

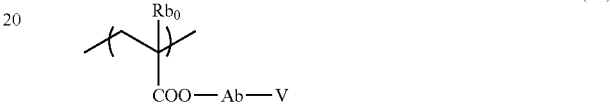

(AI)

In general formula (AI), $Rb_0$ represents a hydrogen atom, a halogen atom or an alkyl group having 1 to 4 carbon atoms.

As the alkyl group represented by $Rb_0$, there can be mentioned, for example, a methyl group, an ethyl group, a propyl group, an n-butyl group, a sec-butyl group, a t-butyl group and the like. The alkyl group represented by $Rb_0$ may have a substituent. As preferred substituents that may be introduced in the alkyl group represented by $Rb_0$, there can be mentioned, for example, a hydroxyl group and a halogen atom.

As the halogen atom represented by $Rb_0$, there can be mentioned a fluorine atom, a chlorine atom, a bromine atom or an iodine atom. The $Rb_0$ is preferably a hydrogen atom or a methyl group.

Ab represents an alkylene group, a bivalent connecting group with an alicyclic hydrocarbon structure of a single ring or multiple rings, a single bond, an ether group, an ester group, a carbonyl group, a carboxyl group or a bivalent connecting group resulting from combination of these. A single bond and a connecting group of the formula -$Ab_1$-$CO_2$— are preferred.

$Ab_1$ is a linear or branched alkylene group or a monocyclic or polycyclic alkylene group, being preferably a methylene group, an ethylene group, a cyclohexylene group, an adamantylene group or a norbornylene group.

V represents any of the groups of the general formulae (LC1-1) to (LC1-17).

The repeating unit having a lactone structure is generally present in the form of optical isomers. Any of the optical isomers may be used. It is both appropriate to use a single type of optical isomer alone and to use a plurality of optical isomers in the form of a mixture. When a single type of optical isomer is mainly used, the optical purity thereof is preferably 90% ee or higher, more preferably 95% ee or higher.

The following repeating units can be mentioned as repeating units each containing an especially preferred lactone group. Selecting the most appropriate lactone group enhances the pattern profile and iso/dense bias. In the formulae, each of Rx and R represents H, $CH_3$, $CH_2OH$ or $CF_3$.

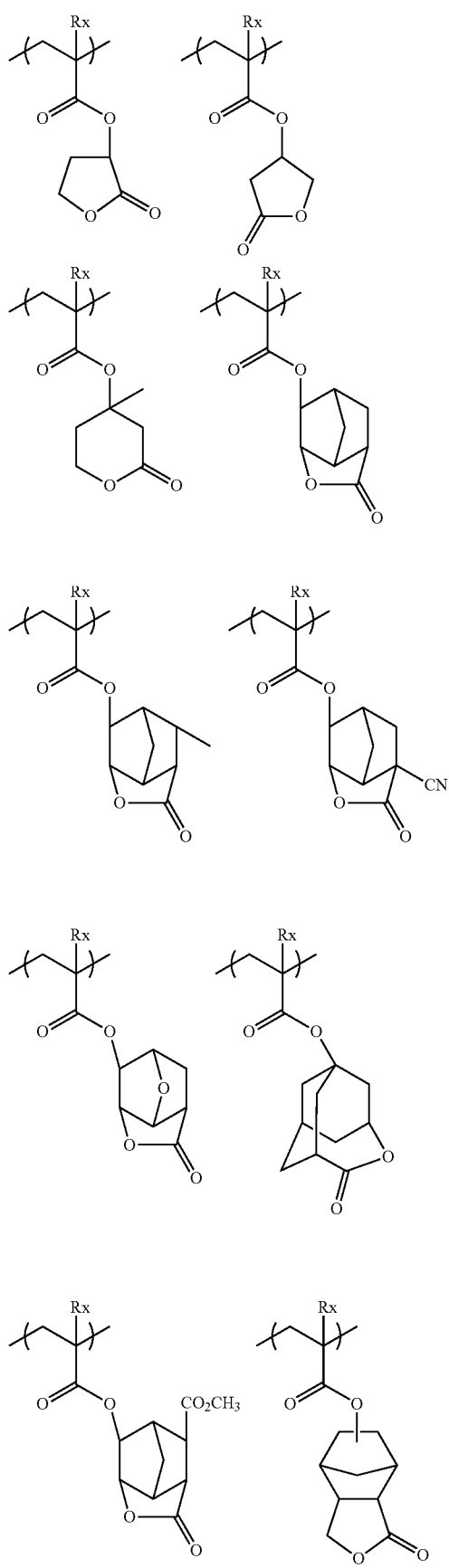
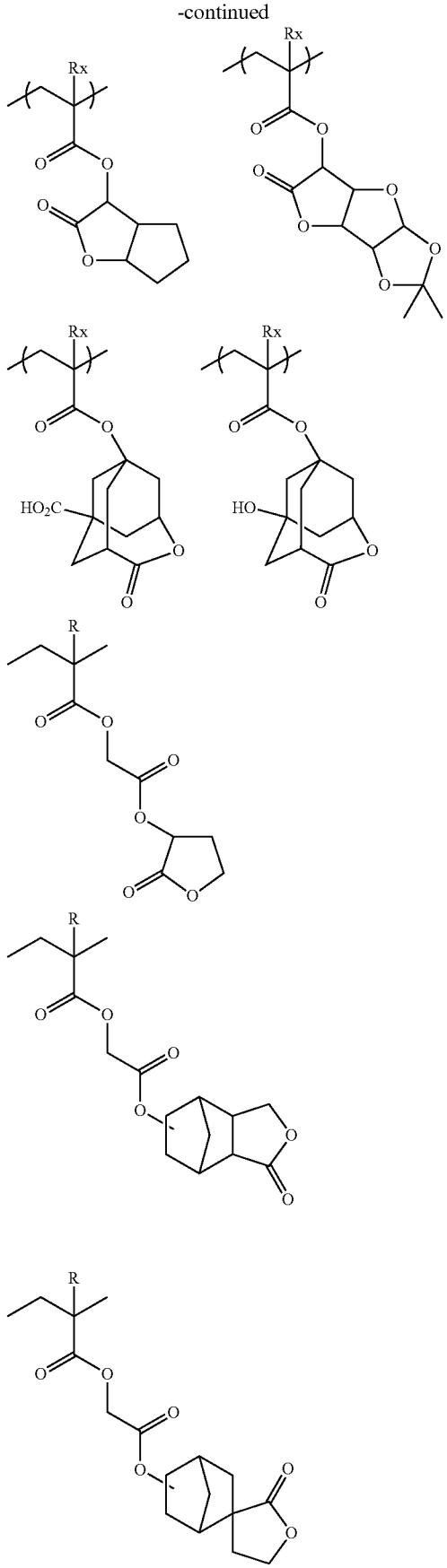

75
-continued
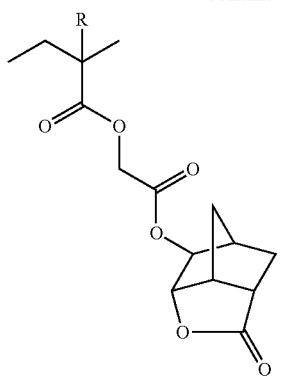
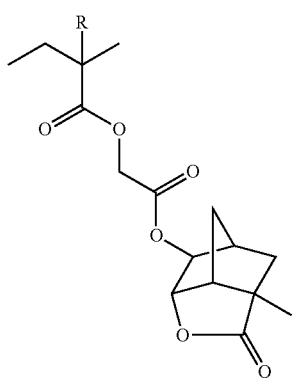
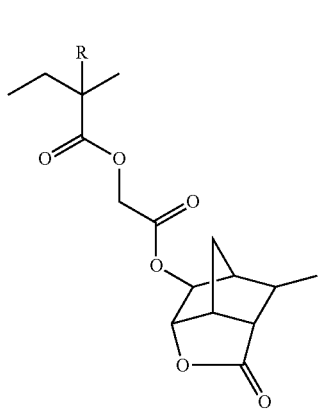
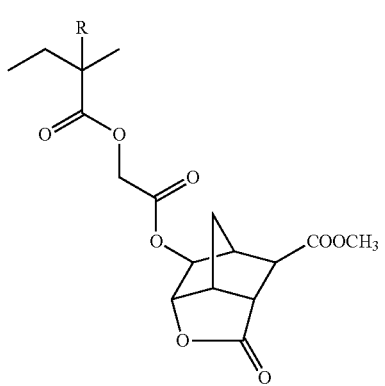
76
-continued
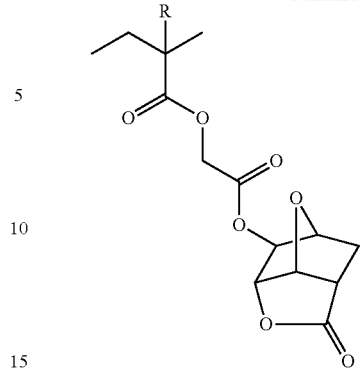
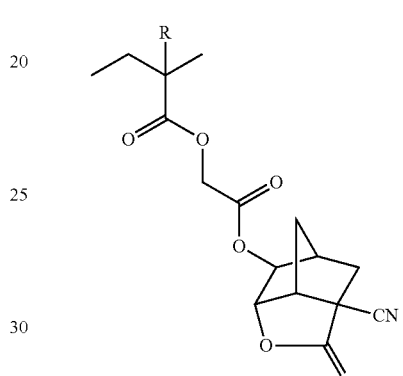
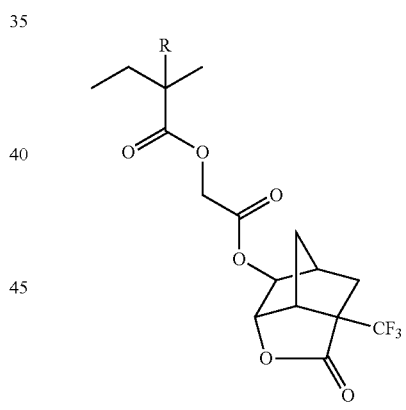
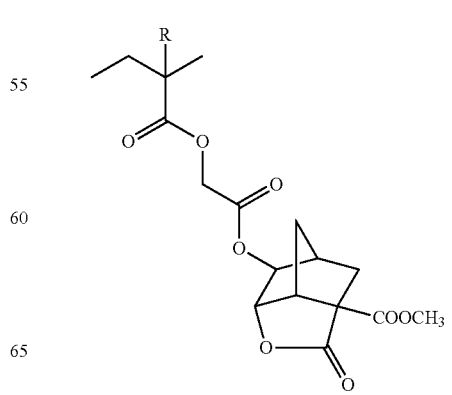

77
-continued
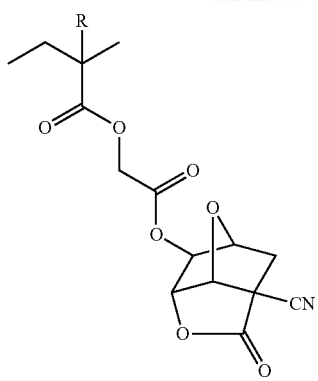
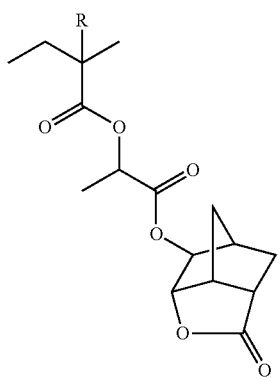
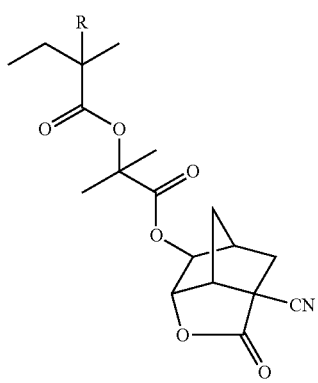
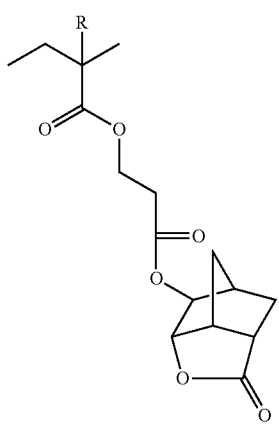
78
-continued
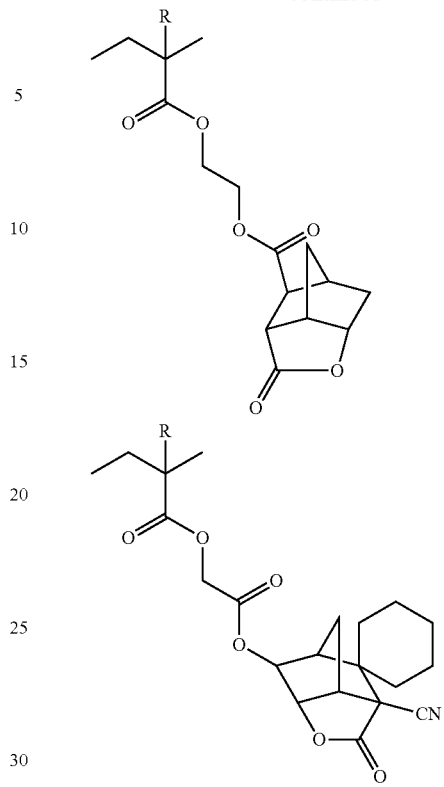
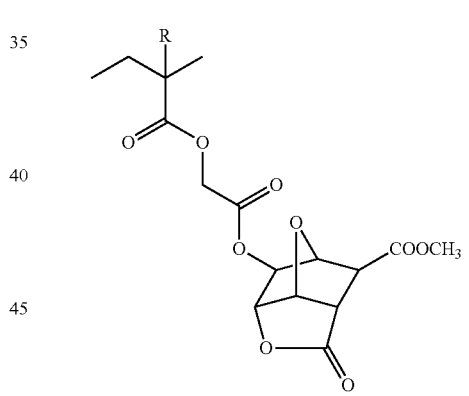
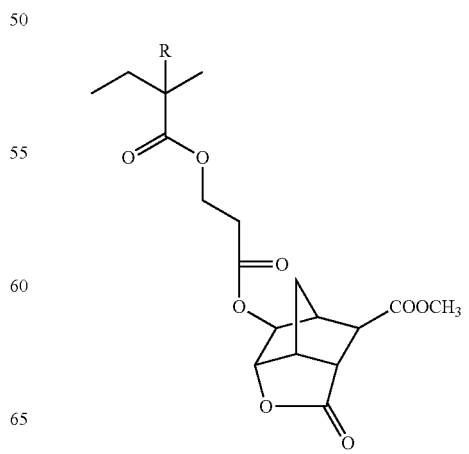

-continued

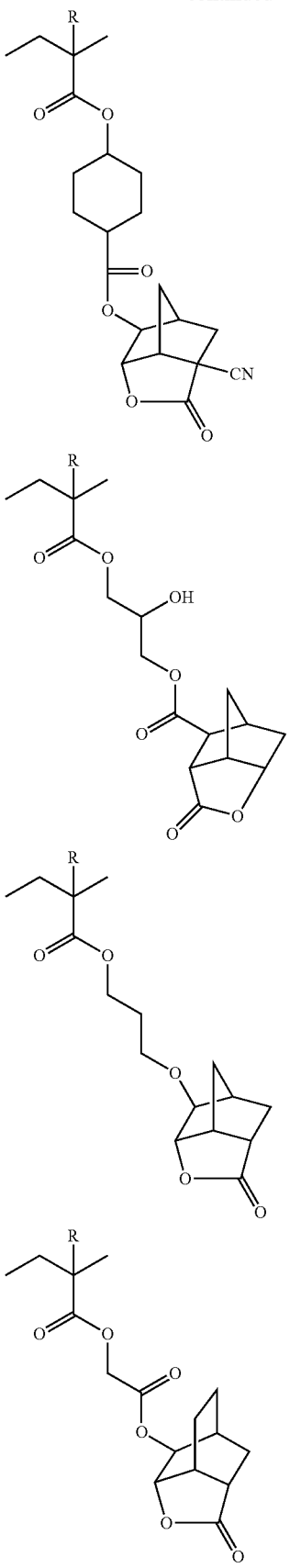

The alicyclic hydrocarbon acid-decomposable resin may contain a plurality of repeating units each containing a lactone group. In this case, it is preferred for the acid-decomposable resin to contain either (1) any one of those of general formula (AI) in which Ab is a single bond together with any one of those of general formula (AI) in which Ab is -$Ab_1$-$CO_2$—, or (2) a mixture of two of those of general formula (AI) in which Ab is -$Ab_1$-$CO_2$—.

The content of repeating unit containing a lactone group (when there are a plurality of repeating units each containing a lactone group, the sum thereof), based on all the repeating units of the resin (B), is preferably in the range of 10 to 70 mol %, more preferably 20 to 60 mol %.

It is preferred for the alicyclic hydrocarbon acid-decomposable resin according to the present invention to have a repeating unit having an alicyclic hydrocarbon structure substituted with a polar group. The containment of this repeating unit would realize enhancements of adhesion to substrate and developer affinity. The polar group is preferably a hydroxyl group or a cyano group.

The hydroxyl group as the polar group constitutes an alcoholic hydroxyl group.

As the alicyclic hydrocarbon structure substituted with a polar group, there can be mentioned, for example, any of the structures of general formulae (VIIa) and (VIIb) below.

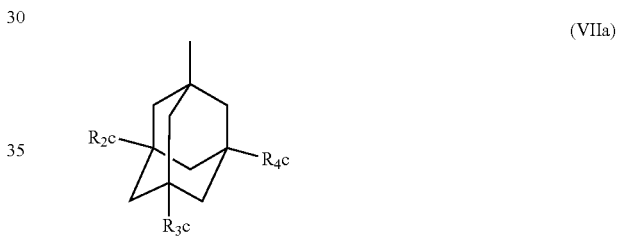

(VIIa)

(VIIb)

In general formula (VIIa), each of $R_2c$ to $R_4c$ independently represents a hydrogen atom, a hydroxyl group or a cyano group, provided that at least one of the $R_2c$ to $R_4c$ represents a hydroxyl group or a cyano group. Preferably, one or two of the $R_2c$ to $R_4c$ are hydroxyl groups and the remainder is a hydrogen atom. More preferably, two of the $R_2c$ to $R_4c$ are hydroxyl groups and the remainder is a hydrogen atom.

The groups of general formula (VIIa) preferably have a dihydroxy form or monohydroxy form, more preferably a dihydroxy form.

As the repeating units containing any of the groups of general formula (VIIa) or (VIIb), there can be mentioned the repeating units of general formulae (II-AB1) and (II-AB2) above wherein at least one of R13' to R16' has any of the groups of general formula (VIIa) or (VIIb) as well as the repeating units of general formula (AIIa) or (AIIb) below. As examples of the former repeating units, there can be mentioned the structures in which $R_5$ of the —$COOR_5$ represents any of the groups of general formula (VIIa) or (VIIb).

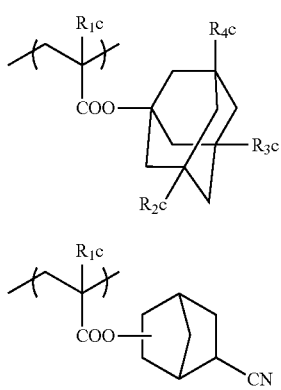

In general formulae (AIIa) and (AIIb), $R_1c$ represents a hydrogen atom, a methyl group, a trifluoromethyl group or a hydroxymethyl group.

$R_2c$ to $R_4c$ have the same meaning as those of general formula (VIIa).

Specific examples of the repeating units having an alicyclic hydrocarbon structure substituted with a polar group, expressed by general formula (AIIa) or (AIIb) will be shown below, which however in no way limit the scope of the present invention.

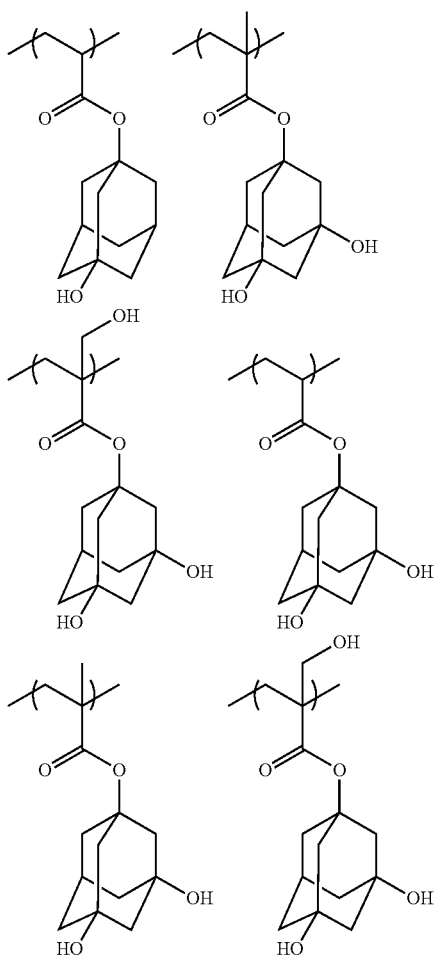

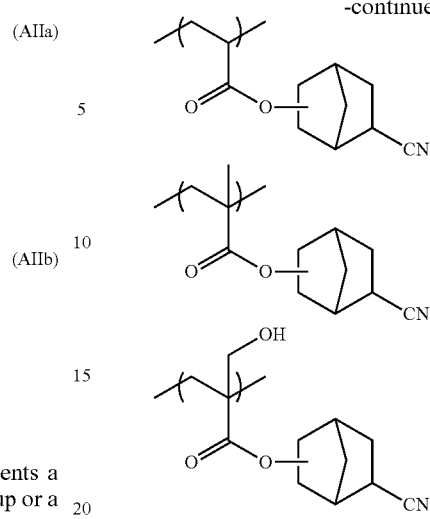

The content of repeating unit mentioned above (when there are a plurality of relevant repeating units, the sum thereof), based on all the repeating units of the resin (B), is preferably in the range of 3 to 30 mol %, more preferably 5 to 25 mol %.

The resin of the present invention may contain a repeating unit that does not contain a hydroxyl group and a cyano group, being stable against acids, other than the foregoing repeating units.

As such a repeating unit, there can be mentioned, for example, any of repeating units of general formula shown below in which a side chain of acrylic structure has a non-acid-decomposable aryl structure or cycloalkyl structure. Further containing this structure promises the attainment of contrast regulation, enhancement of etching resistance, etc.

This repeating unit may be introduced in the above-mentioned resin containing a hydroxystyrene repeating unit or alicyclic hydrocarbon acid-decomposable resin. When this repeating unit is introduced in the alicyclic hydrocarbon acid-decomposable resin, from the viewpoint of 193 nm light absorption, it is preferred to contain no aromatic ring structure.

In general formula (III), $R_5$ represents a hydrocarbon group.

Ra represents a hydrogen atom, an alkyl group (preferably a methyl group), a hydroxyalkyl group (preferably a hydroxymethyl group) or a trifluoromethyl group.

It is preferred for the hydrocarbon group represented by $R_5$ to contain a ring structure therein. As particular examples of the hydrocarbon groups containing a ring structure, there can be mentioned a mono- or polycycloalkyl group (preferably 3 to 12 carbon atoms, more preferably 3 to 7 carbon atoms), a mono- or polycycloalkenyl group (preferably 3 to 12 carbon atoms), an aryl group (preferably 6 to 20 carbon atoms, more preferably 6 to 12 carbon atoms), an aralkyl group (preferably 7 to 20 carbon atoms, more preferably 7 to 12 carbon atoms) and the like.

The above cycloalkyl groups include ring-assembly hydrocarbon groups and crosslinked-ring hydrocarbon groups. As crosslinked-ring hydrocarbon rings, there can be mentioned, for example, bicyclic hydrocarbon rings, tricyclic hydrocarbon rings and tetracyclic hydrocarbon rings. Further, the crosslinked-ring hydrocarbon rings include condensed rings, for example, those resulting from the condensation of a plurality of 5- to 8-membered cycloalkane rings.

As preferred crosslinked-ring hydrocarbon rings, there can be mentioned, for example, a norbornyl group, an adamantyl group, a bicyclooctanyl group and a tricyclo[5,2,1,0$^{2,6}$]decanyl group. As more preferred crosslinked-ring hydrocarbon rings, there can be mentioned a norbornyl group and an adamantyl group.

As preferred examples of the aryl groups, there can be mentioned a phenyl group, a naphthyl group, a biphenyl group and the like. As preferred examples of the aralkyl groups, there can be mentioned a phenylmethyl group, a phenylethyl group, a naphthylmethyl group and the like.

Substituents may be introduced in these hydrocarbon groups. As preferred substituents, there can be mentioned, for example, a halogen atom, an alkyl group, a hydroxyl group protected by a protective group and an amino group protected by a protective group. The halogen atom is preferably a bromine, chlorine or fluorine atom, and the alkyl group is preferably a methyl, ethyl, butyl or t-butyl group. A substituent may further be introduced in this alkyl group. As an optionally further introduced substituent, there can be mentioned a halogen atom, an alkyl group, a hydroxyl group protected by a protective group or an amino group protected by a protective group.

As the protective group, there can be mentioned, for example, an alkyl group, a cycloalkyl group, an aralkyl group, a substituted methyl group, a substituted ethyl group, an alkoxycarbonyl group or an aralkyloxycarbonyl group. The alkyl group is preferably an alkyl group having 1 to 4 carbon atoms. The substituted methyl group is preferably a methoxymethyl, methoxythiomethyl, benzyloxymethyl, t-butoxymethyl or 2-methoxyethoxymethyl group. The substituted ethyl group is preferably a 1-ethoxyethyl or 1-methyl-1-methoxyethyl group. The acyl group is preferably an aliphatic acyl group having 1 to 6 carbon atoms, such as a formyl, acetyl, propionyl, butyryl, isobutyryl, valeryl or pivaloyl group. The alkoxycarbonyl group is, for example, an alkoxycarbonyl group having 1 to 4 carbon atoms.

The content of any of repeating units of general formula (III) based on all the repeating units of the resin (B) is preferably in the range of 0 to 40 mol %, more preferably 0 to 20 mol %.

Specific examples of the repeating units of general formula (III) will be shown below, which in no way limit the scope of the present invention. In the formulae, Ra represents H, CH$_3$, CH$_2$OH or CF$_3$.

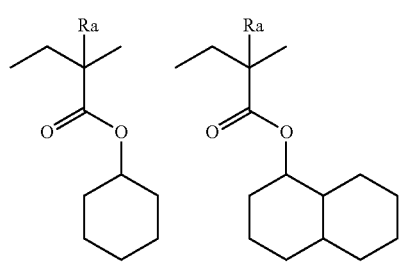

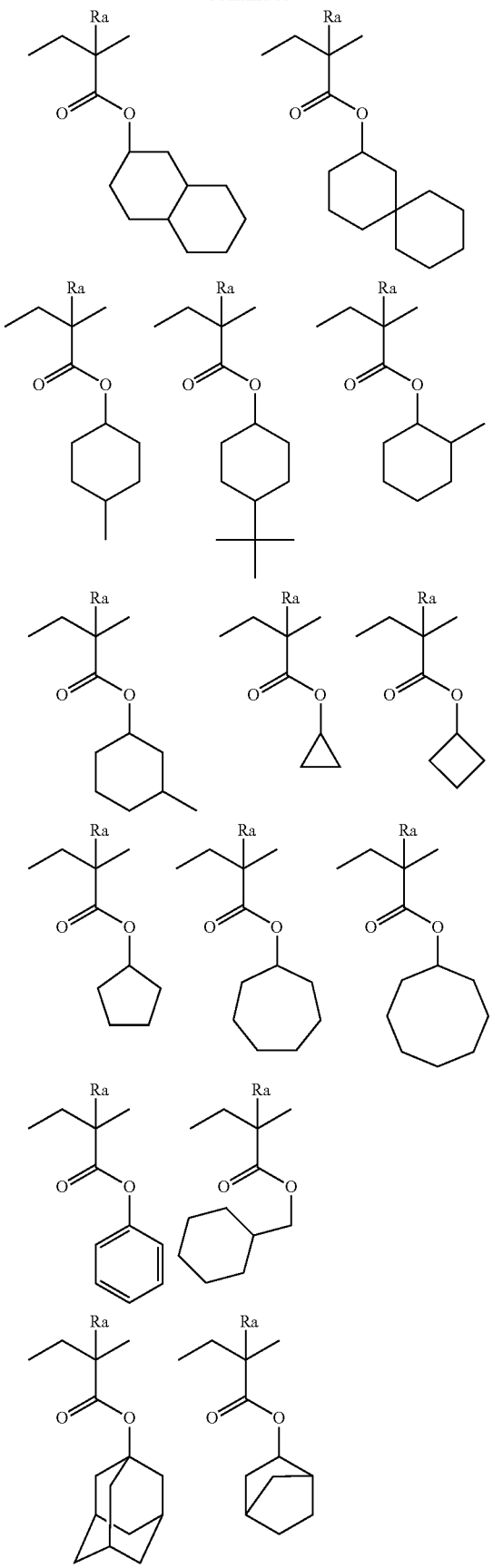

-continued

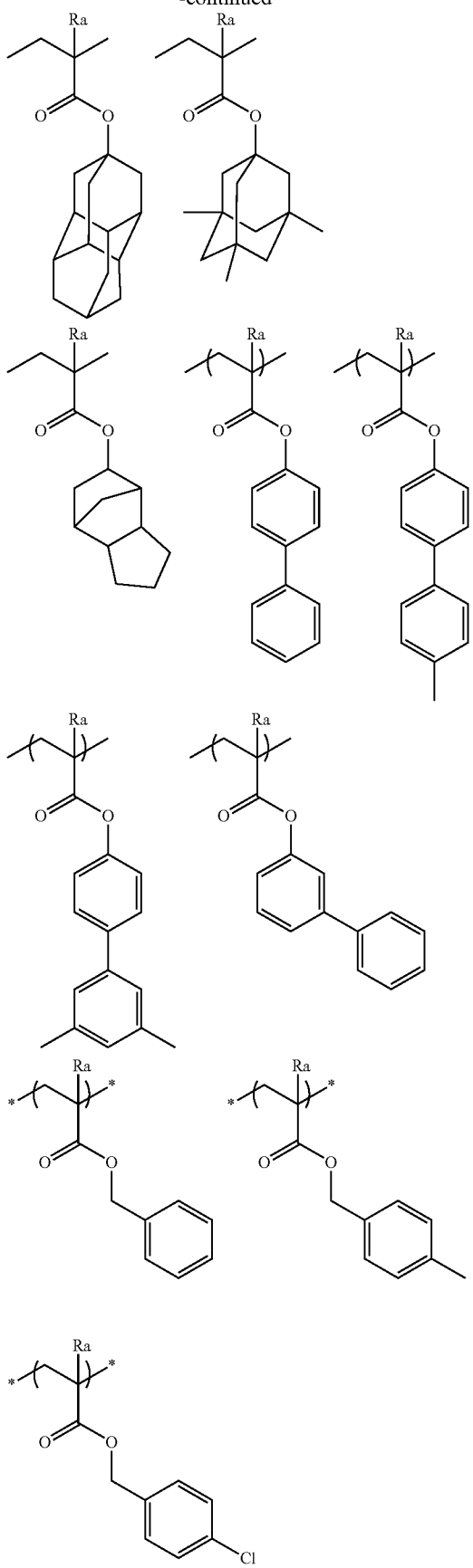

-continued

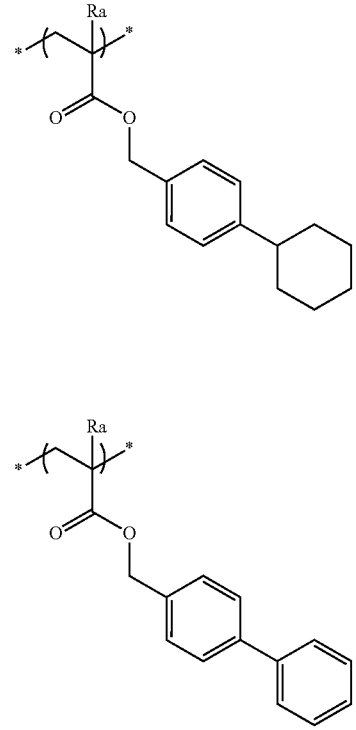

The content of any of these repeating units (when there are a plurality of relevant repeating units, the sum thereof), based on all the repeating units of the resin, is preferably in the range of 0 to 30 mol %, more preferably 1 to 20 mol %.

The alicyclic hydrocarbon acid-decomposable resin may have any of the repeating units of general formula (VIII) below.

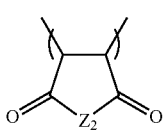
(VIII)

In general formula (VIII), $Z_2$ represents —O— or —N($R_{41}$)—. $R_{41}$ represents a hydrogen atom, a hydroxyl group, an alkyl group or —OSO$_2$—$R_{42}$. $R_{42}$ represents an alkyl group, a cycloalkyl group or a camphor residue. The alkyl groups represented by $R_{41}$ and $R_{42}$ may be substituted with, for example, a halogen atom. The halogen atom is preferably a fluorine atom.

Specific examples of the repeating units of general formula (VIII) will be shown below, which however in no way limit the scope of the present invention.

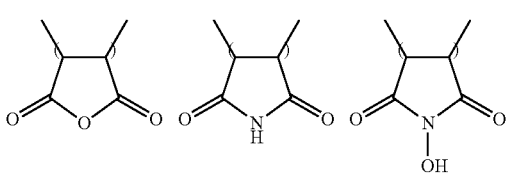

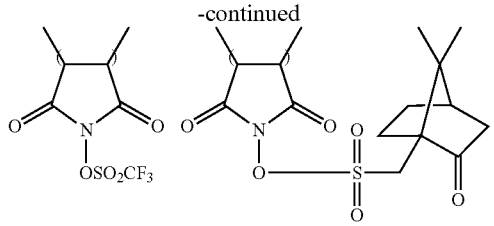

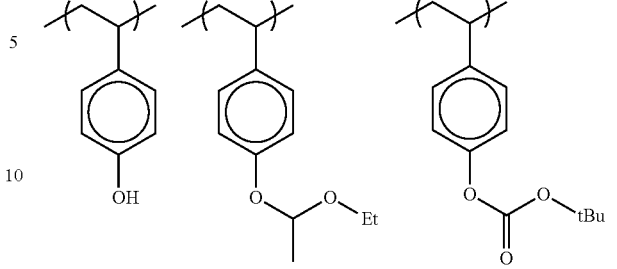

It is preferred for the alicyclic hydrocarbon acid-decomposable resin to contain a repeating unit containing an alkali-soluble group, especially a repeating unit containing a carboxyl group. The resolution in contact hole usage can be enhanced by containing this repeating unit.

Both a repeating unit wherein a carboxyl group is directly bonded to the principal chain of a resin and a repeating unit wherein a carboxyl group is bonded via a connecting group to the principal chain of a resin can be mentioned as preferred repeating units containing a carboxyl group.

As an example of the former repeating unit, there can be mentioned a repeating unit from acrylic acid or methacrylic acid. The connecting group of the latter repeating unit may have a mono- or polycycloalkyl structure.

The repeating units from acrylic acid and methacrylic acid are most preferred as the repeating unit containing a carboxyl group.

The weight average molecular weight of the resin that when acted on by an acid, is decomposed to thereby increase its solubility in an alkali developer in terms of polystyrene molecular weight measured by GPC is preferably in the range of 2000 to 200,000. Causing the weight average molecular weight to be 2000 or greater would realize enhancements of thermal stability and dry etching performance. On the other hand, causing the weight average molecular weight to be 200,000 or less would realize an enhancement of developability and would also, due to a viscosity lowering, enhance film forming properties.

The weight average molecular weight is more preferably from 2500 to 50,000 and further preferably from 3000 to 20,000. In the micropattern formation using electron beams, X-rays or high-energy rays of 50 nm or less wavelength (EUV, etc.), the weight average molecular weight is most preferably from 3000 to 10,000. The thermal stability, resolving power, development defect, etc. of the composition can be simultaneously satisfied by regulating the molecular weight.

The dispersity (Mw/Mn) of the resin as the component (B) is preferably in the range of 1.0 to 3.0, more preferably 1.2 to 2.5 and further preferably 1.2 to 1.6. The line edge roughness performance can be enhanced by regulating the dispersity so as to fall within an appropriate range.

Particular examples of the above resins will be shown below, which however in no way limit the scope of the present invention.

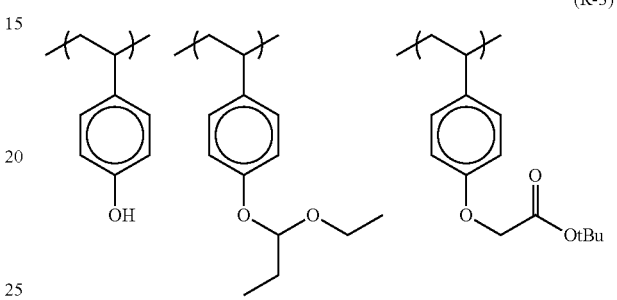

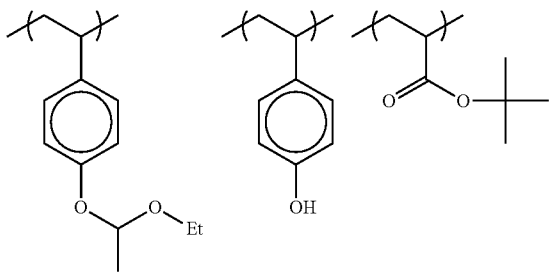

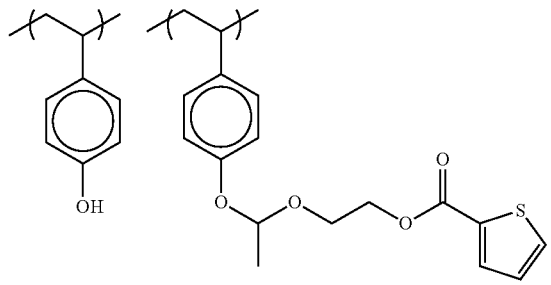

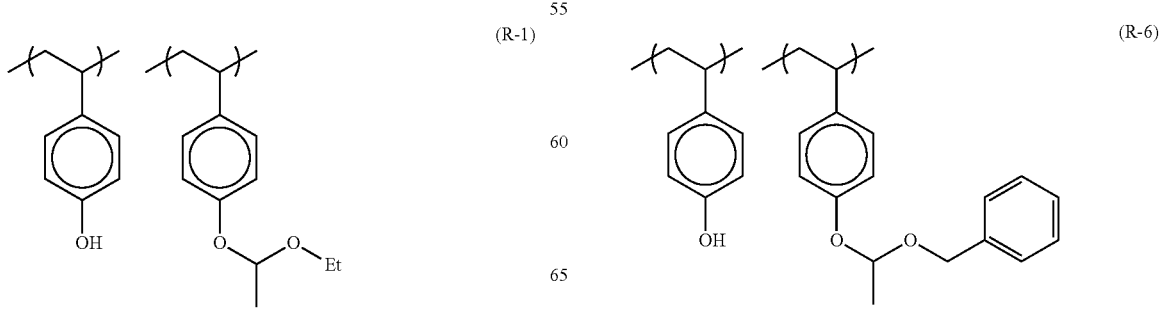

-continued
(R-7)
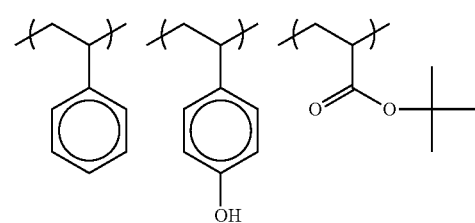
(R-8)
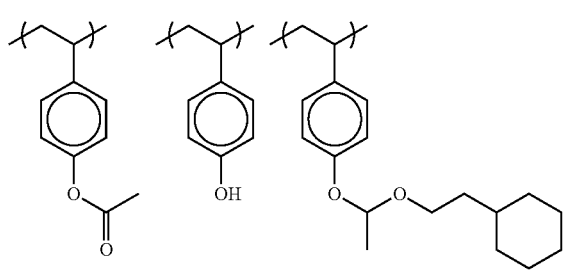
(R-9)
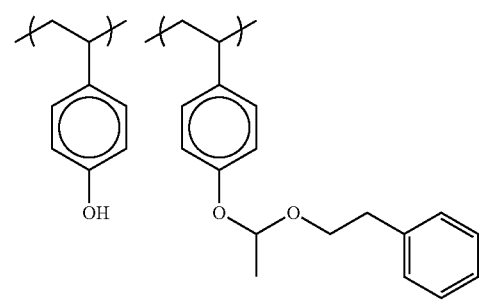
(R-10)
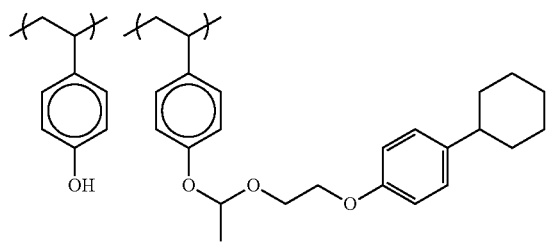
(R-11)
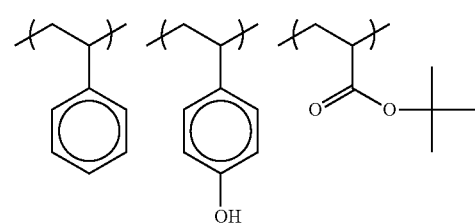
-continued
(R-12)
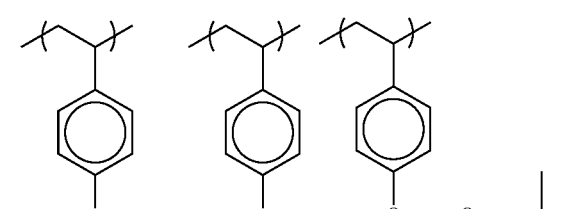
(R-13)
(R-14)
(R-15)

(R-16)
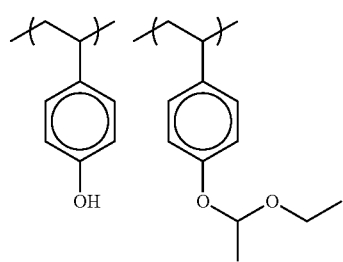
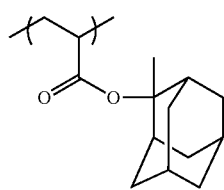
R-21
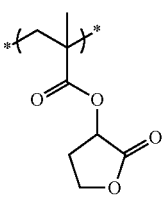
(R-17)
R-22
R-18
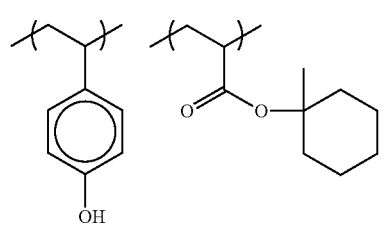
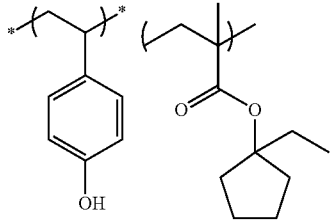
R-23
R-19
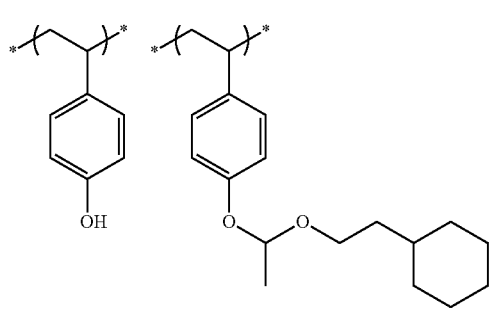
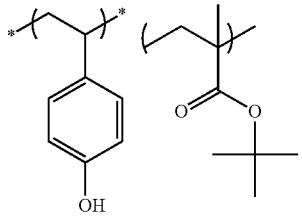
R-24
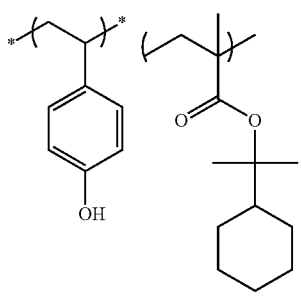
R-20
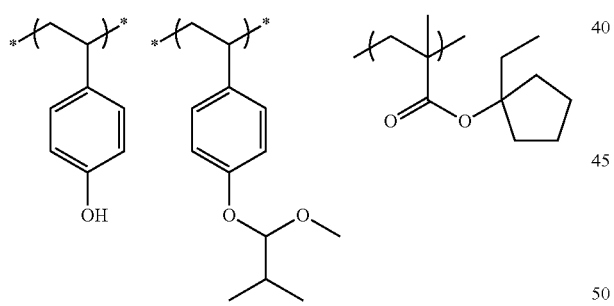
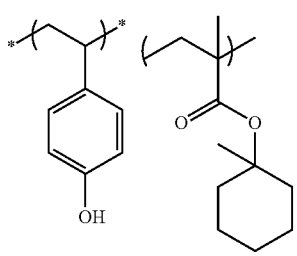
R-25
R-26
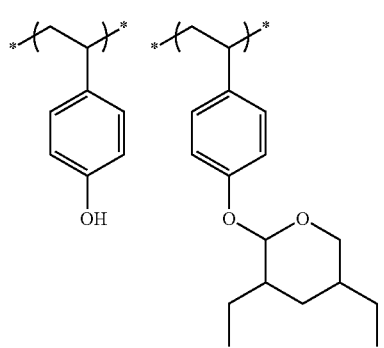
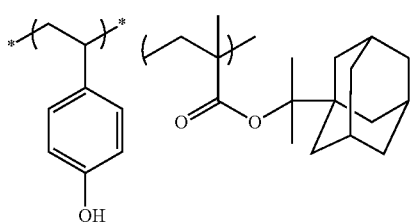

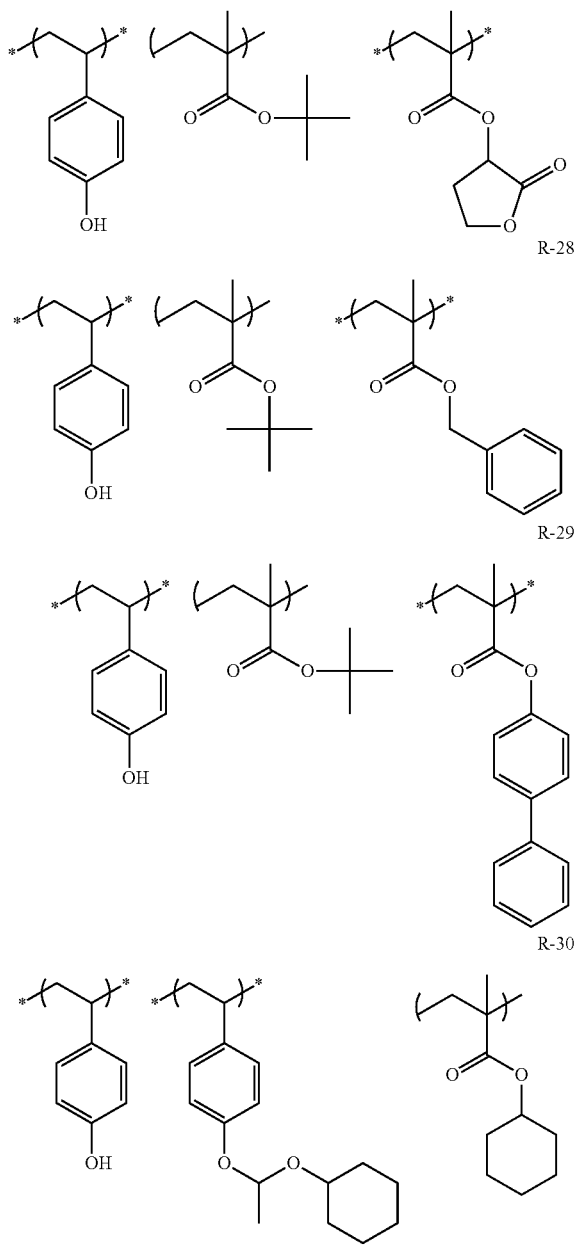

In the above specific examples, tBu represents a t-butyl group.

The content of resin (B) in the composition of the present invention based on the total solids thereof is preferably in the range of 5 to 99.9 mass %, more preferably 50 to 95 mass % and most preferably 60 to 93 mass %.

[3] Resin Soluble in an Alkali Developer

Hereinafter, this resin may also be referred to as "alkali-soluble resin."

The negative actinic-ray- or radiation-sensitive resin composition of the present invention may contain an alkali-soluble resin (C) and further according to necessity a crosslinking agent (D). The alkali dissolution rate of the alkali-soluble resin (C) as measured in a 0.261 N tetramethylammonium hydroxide (TMAH) (23° C.) is preferably 2 nm/sec or higher, especially preferably 20 nm/sec or higher.

As the alkali-soluble resin for use in the present invention, there can be mentioned, for example, a novolak resin, a hydrogenated novolak resin, an acetone-pyrogallol resin, an o-polyhydroxystyrene, a m-polyhydroxystyrene, a p-polyhydroxystyrene, a hydrogenated polyhydroxystyrene, a halogenated or alkylated polyhydroxystyrene, a hydroxystyrene-N-substituted maleimide copolymer, an o/p- and m/p-hydroxystyrene copolymer, a partial O-alkylation product of hydroxyl of polyhydroxystyrene (for example, a 5 to 30 mol % O-methylation product, O-(1-methoxy)ethylation product, O-(1-ethoxy)ethylation product, O-2-tetrahydropyranylation product, O-(t-butoxycarbonyl)methylation product, etc.), an O-acylation product thereof (for example, a 5 to 30 mol % O-acetylation product, O-(t-butoxy)carbonylation product, etc.), a styrene-maleic anhydride copolymer, a styrene-hydroxystyrene copolymer, an α-methylstyrene-hydroxystyrene copolymer, a carboxylated methacrylic resin or its derivative, or a polyvinyl alcohol derivative. However, the alkali-soluble resins are not limited to these.

Preferred alkali-soluble resins are a novolak resin, an o-polyhydroxystyrene, a m-polyhydroxystyrene, a p-polyhydroxystyrene, a copolymer of these polyhydroxystyrenes, an alkylated polyhydroxystyrene, a partial O-alkylation product or O-acylation product of polyhydroxystyrene, a styrene-hydroxystyrene copolymer and an α-methylstyrene-hydroxystyrene copolymer.

Especially in the present invention, resins having a hydroxystyrene structure are preferred. Among various hydroxystyrene structures, a m-hydroxystyrene structure is most preferred.

The above novolak resin can be obtained by addition condensation of a given monomer as a main component with an aldehyde conducted in the presence of an acid catalyst.

The weight average molecular weight of the alkali-soluble resin is 2000 or greater, preferably from 5000 to 200,000 and more preferably 5000 to 100,000. Herein, the weight average molecular weight is in terms of polystyrene molecular weight measured by gel permeation chromatography (GPC).

In the present invention, two or more types of alkali-soluble resins (C) may be used in combination.

The content of alkali-soluble resin (C), based on the total solids of the composition, is generally in the range of 40 to 97 mass %, preferably 60 to 90 mass %.

[4] Acid Crosslinking Agent Capable of Crosslinking with the Alkali-Soluble Resin by the Action of an Acid The negative actinic-ray- or radiation-sensitive resin composition of the present invention may further contain a crosslinking agent (D).

Any crosslinking agent can be used as long as it is a compound capable of crosslinking with the resin soluble in an alkali developer by the action of an acid. However, compounds (1) to (3) below are preferred.

(1) A hydroxymethylated form, alkoxymethylated or acyloxymethylated form of phenol derivative.

(2) A compound having an N-hydroxymethyl group, an N-alkoxymethyl group or an N-acyloxymethyl group.

(3) A compound having an epoxy group.

The alkoxymethyl group preferably has 6 or less carbon atoms, and the acyloxymethyl group preferably has 6 or less carbon atoms.

Those especially preferred among these crosslinking agents will be shown below.

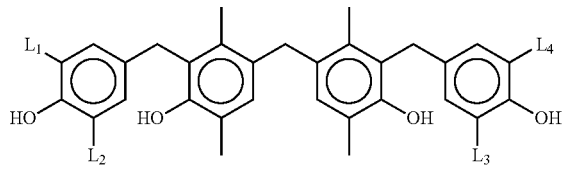

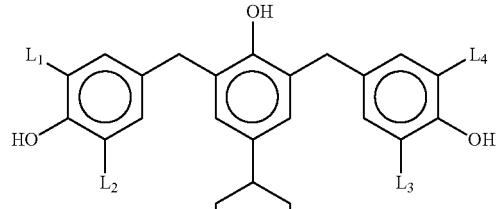

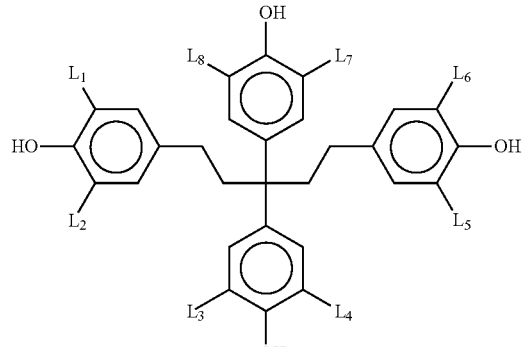

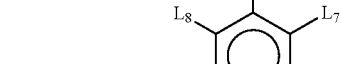

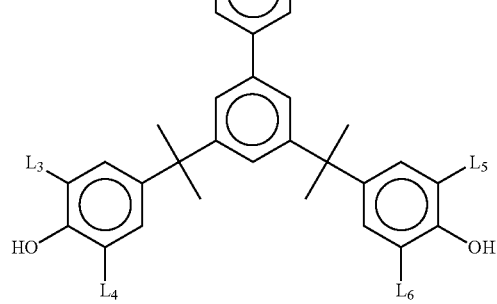

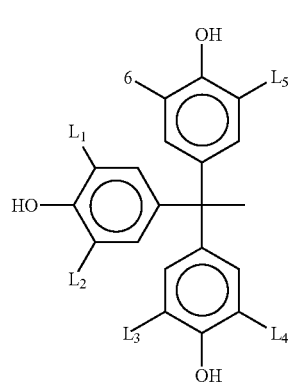

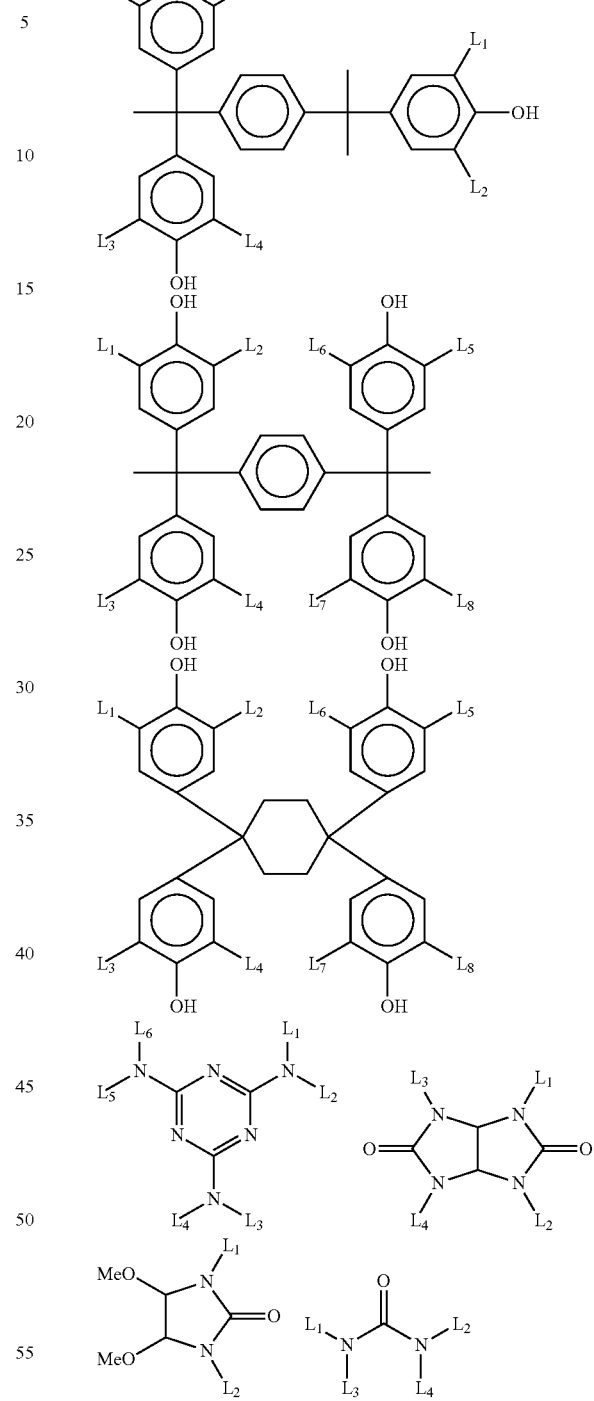

In the formulae, $L_1$ to $L_8$ may be identical to or different from each other, and each thereof represents a hydrogen atom, a hydroxymethyl group, an alkoxymethyl group, such as a methoxymethyl group or an ethoxymethyl group, or an alkyl group having 1 to 6 carbon atoms.

The crosslinking agent is generally added in an amount of 3 to 70 mass %, preferably 5 to 50 mass %, based on the total solids of the composition.

[5] Dissolution Inhibiting Compound of 3000 or Less Molecular Weight that is Decomposed by the Action of an Acid to Thereby Increase the Solubility in an Alkali Developer The positive actinic-ray- or radiation-sensitive resin composition of the present invention may further contain a dissolution inhibiting compound of 3000 or less molecular weight that is decomposed by the action of an acid to thereby increase the solubility in an alkali developer. Hereinafter, this compound is also referred to as "dissolution inhibiting compound." From the viewpoint of preventing any lowering of 220 nm or shorter transmission, the dissolution inhibiting compound is preferably an alicyclic or aliphatic compound containing an acid-decomposable group, such as any of cholic acid derivatives having an acid-decomposable group described in Proceeding of SPIE, 2724, 355 (1996). Particular examples of the acid-decomposable groups are the same as set forth above with respect to the acid-decomposable unit.

When the composition of the present invention is exposed to a KrF excimer laser or irradiated with an electron beam, preferred use is made of a compound containing a structure resulting from substitution of the phenolic hydroxyl group of a phenol compound with an acid-decomposable group. The phenol compound preferably contains 1 to 9 phenol skeletons, more preferably 2 to 6 phenol skeletons.

The content of dissolution inhibiting compound is preferably in the range of 3 to 50 mass %, more preferably 5 to 40 mass % based on the total solids of the composition.

Specific examples of the dissolution inhibiting compounds will be shown below, which however in no way limit the scope of the present invention.

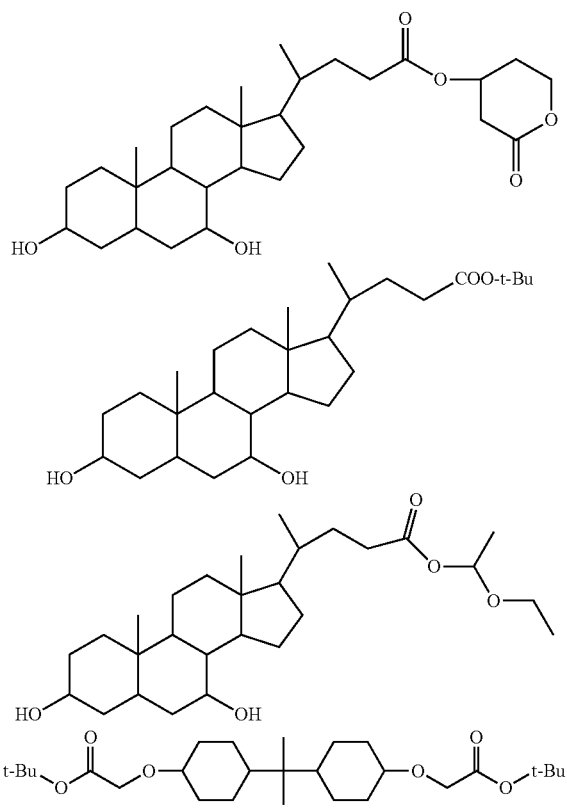

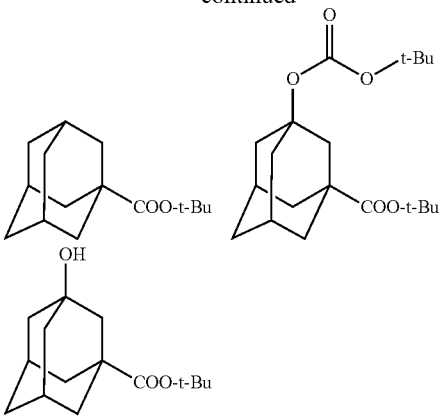

[6] Other Component

The positive or negative actinic-ray- or radiation-sensitive resin composition of the present invention may further contain a basic compound, an organic solvent, a surfactant, a dye, a plasticizer, a photosensitizer, a compound capable of accelerating the dissolution in a developer, a compound containing a functional group as a proton acceptor, etc.

<Basic Compound>

The composition of the present invention may further contain a basic compound. Any change over time of performance during the period between exposure and baking (postbake) can be reduced by further containing a basic compound. Moreover, the in-film diffusion of an acid generated upon exposure can be controlled by further containing a basic compound.

The basic compound is preferably a nitrogen-containing organic compound. Useful basic compounds are not particularly limited. However, for example, the compounds of categories (1) to (4) below are preferably used.

(1) Compounds of General Formula (BS-1) Below

(BS-1)

In general formula (BS-1), each of Rs independently represents a hydrogen atom or an organic group, provided that at least one of the three Rs represents an organic group. The organic group is a linear or branched alkyl group, a monocyclic or polycyclic alkyl group, an aryl group or an aralkyl group.

The number of carbon atoms of the alkyl group represented by R is not particularly limited. However, it is generally in the range of 1 to 20, preferably 1 to 12.

The number of carbon atoms of the cycloalkyl group represented by R is not particularly limited. However, it is generally in the range of 3 to 20, preferably 5 to 15.

The number of carbon atoms of the aryl group represented by R is not particularly limited. However, it is generally in the range of 6 to 20, preferably 6 to 10. In particular, an aryl group, such as a phenyl group, a naphthyl group and the like, can be mentioned.

The number of carbon atoms of the aralkyl group represented by R is not particularly limited. However, it is generally in the range of 7 to 20, preferably 7 to 11. In particular, an aralkyl group, such as a benzyl group and the like, can be mentioned.

In the alkyl group, cycloalkyl group, aryl group and aralkyl group represented by R, a hydrogen atom thereof may be replaced by a substituent. As the substituent, there can be mentioned, for example, an alkyl group, a cycloalkyl group, an aryl group, an aralkyl group, an alkoxy group, an aryloxy group, an alkylcarbonyloxy group, an alkyloxycarbonyl group and the like.

In the compounds of general formula (BS-1), it is preferred that at least two of the three Rs be organic groups.

Specific examples of the compounds of General Formula (BS-1) include tri-n-butylamine, tri-n-pentylamine, tri-n-octylamine, tri-n-decylamine, triisodecylamine, dicyclohexylmethylamine, tetradecylamine, pentadecylamine, hexadecylamine, octadecylamine, didecylamine, methyloctadecylamine, dimethylundecylamine, N,N-dimethyldodecylamine, methyldioctadecylamine, N,N-dibutylaniline, N,N-dihexylaniline, 2,6-diisopropylaniline, 2,4,6-tri (t-butyl)aniline and the like.

Any of the compounds of general formula (BS-1) in which at least one of the Rs is a hydroxylated alkyl group can be mentioned as a preferred form of compound. Specific examples of the compounds include triethanolamine, N,N-dihydroxyethylaniline and the like.

With respect to the alkyl group represented by R, an oxygen atom may be present in the alkyl chain to thereby form an oxyalkylene chain. The oxyalkylene chain preferably consists of —$CH_2CH_2O$—. As particular examples thereof, there can be mentioned tris(methoxyethoxyethyl)amine, compounds shown in column 3 line 60 et seq. of U.S. Pat. No. 6,040,112 and the like.

(2) Compounds with Nitrogen-Containing Heterocyclic Structure

The nitrogen-containing heterocyclic structure optionally may have aromaticity. It may have a plurality of nitrogen atoms, and also may have a heteroatom other than nitrogen. For example, there can be mentioned compounds with an imidazole structure (2-phenylbenzoimidazole, 2,4,5-triphenylimidazole and the like), compounds with a piperidine structure (N-hydroxyethylpiperidine, bis(1,2,2,6,6-pentamethyl-4-piperidyl) sebacate and the like), compounds with a pyridine structure (4-dimethylaminopyridine and the like) and compounds with an antipyrine structure (antipyrine, hydroxyantipyrine and the like).

Further, compounds with two or more ring structures can be appropriately used. For example, there can be mentioned 1,5-diazabicyclo[4.3.0]non-5-ene, 1,8-diazabicyclo[5.4.0]-undec-7-ene and the like.

(3) Amine Compounds with Phenoxy Group

The amine compounds with a phenoxy group are those having a phenoxy group at the end of the alkyl group of each amine compound opposite to the nitrogen atom. The phenoxy group may have a substituent, such as an alkyl group, an alkoxy group, a halogen atom, a cyano group, a nitro group, a carboxyl group, a carboxylic ester group, a sulfonic ester group, an aryl group, an aralkyl group, an acyloxy group, an aryloxy group and the like.

Compounds having at least one oxyalkylene chain between the phenoxy group and the nitrogen atom are preferred. The number of oxyalkylene chains in each molecule is preferably in the range of 3 to 9, more preferably 4 to 6. Among the oxyalkylene chains, —$CH_2CH_2O$— is preferred.

Particular examples thereof include 2-[2-{2-(2,2-dimethoxy-phenoxyethoxy)ethyl}-bis-(2-methoxyethyl)]-amine, compounds (C1-1) to (C3-3) shown in section [0066] of US 2007/0224539 A1 and the like.

(4) Ammonium Salts

Ammonium salts can also be appropriately used. Hydroxides and carboxylates are preferred. Preferred particular examples thereof are tetraalkylammonium hydroxides, such as tetrabutylammonium hydroxide.

As other compounds usable in the composition of the present invention, there can be mentioned the compounds synthesized in Examples of JP-A-2002-363146, the compounds described in Paragraph 0108 of JP-A-2007-298569, and the like.

Further, photosensitive basic compounds may be used as the basic compound. As photosensitive basic compounds, use can be made of, for example, the compounds described in Jpn. PCT National Publication No. 2003-524799, J. Photopolym. Sci&Tech. Vol. 8, p. 543-553 (1995), etc.

The molecular weight of each of these basic compounds is preferably in the range of 250 to 2000, more preferably 400 to 1000.

These basic compounds are used individually or in combination.

The content of basic compound based on the total solids of the composition is preferably in the range of 0.01 to 8.0 mass %, more preferably 0.1 to 5.0 mass % and most preferably 0.2 to 4.0 mass %.

<Surfactant>

The composition of the present invention may further contain a surfactant. When the composition contains a surfactant, the surfactant is preferably a fluorinated and/or siliconized surfactant.

As such a surfactant, there can be mentioned, for example, Megafac F176 or Megafac R08 produced by Dainippon Ink & Chemicals, Inc., PF656 or PF6320 produced by OMNOVA SOLUTIONS, INC., Troy Sol S-366 produced by Troy Chemical Co., Ltd., Florad FC430 produced by Sumitomo 3M Ltd., polysiloxane polymer KP-341 produced by Shin-Etsu Chemical Co., Ltd., and the like.

Surfactants other than these fluorinated and/or siliconized surfactants can also be used. In particular, the other surfactants include polyoxyethylene alkyl ethers, polyoxyethylene alkyl aryl ethers and the like.

Moreover, generally known surfactants can also be appropriately used. As useful surfactants, there can be mentioned, for example, those described in section [0273] et seq of US 2008/0248425 A1.

These surfactants may be used alone or in combination.

The amount of surfactant added is preferably in the range of 0 to 2 mass %, more preferably 0.0001 to 2 mass %, further more preferably 0.001 to 1 mass %, based on the total solids of the composition.

(Solvent)

The solvent that is usable in the preparation of the composition is not particularly limited as long as it can dissolve the components of the composition. For example, preferred use is made of a solvent containing either one or two or more members selected from among an alkylene glycol monoalkyl ether carboxylate (propylene glycol monomethyl ether acetate and the like), an alkylene glycol monoalkyl ether (propylene glycol monomethyl ether and the like), an alkyl lactate (ethyl lactate, methyl lactate and the like), a cyclolactone (γ-butyrolactone and the like, preferably having 4 to 10 carbon atoms), a linear or cyclic ketone (2-heptanone, cyclohexanone and the like, preferably having 4 to 10 carbon atoms), an alkylene carbonate (ethylene carbonate, propylene carbonate and the like), an alkyl carboxylate (preferably an alkyl acetate such as butyl acetate), an alkyl alkoxyacetate (preferably ethyl ethoxypropionate) and the like. As other useful solvents, there can be mentioned, for example, those described in section [0244] et seq. of US 2008/0248425 A1 and the like.

Among the above solvents, an alkylene glycol monoalkyl ether carboxylate, an alkylene glycol monoalkyl ether and ethyl lactate are especially preferred.

These solvents may be used alone or in combination. When a plurality of solvents are mixed together, it is preferred to mix a hydroxylated solvent with a non-hydroxylated solvent. The mass ratio of hydroxylated solvent to non-hydroxylated solvent is in the range of 1/99 to 99/1, preferably 10/90 to 90/10 and more preferably 20/80 to 60/40.

The hydroxylated solvent is preferably an alkylene glycol monoalkyl ether and an alkyl lactate. The non-hydroxylated solvent is preferably an alkylene glycol monoalkyl ether carboxylate.

The amount of solvent used is not particularly limited. However, the amount is generally so regulated that the total solid concentration of the composition falls in the range of preferably 0.5 to 30 mass %, more preferably 1.0 to 10 mass %. In particular when an electron beam or EUV lithography is carried out using the composition of the present invention, the amount is so regulated that the concentration falls in the range of preferably 2.0 to 6.0 mass %, more preferably 2.0 to 4.5 mass %.

(Other Additive)

The positive or negative actinic-ray- or radiation-sensitive resin composition of the present invention may further according to necessity contain a dye, a plasticizer, a photosensitizer, a light absorber, a compound capable of accelerating the dissolution in a developer (for example, a phenolic compound of 1000 or less molecular weight, or a carboxylated alicyclic or aliphatic compound), etc. Still further, appropriate use can be made of compounds having a functional group as a proton acceptor described in, for example, JP-A's 2006-208781 and 2007-286574.

[7] Method of Forming Pattern

The positive or negative actinic-ray- or radiation-sensitive resin composition of the present invention is typically used in the following manner. Namely, the composition of the present invention is typically applied onto a support, such as a substrate, thereby forming a film. The thickness of the film is preferably in the range of 0.02 to 0.1 µm. The method of application onto a substrate is preferably a spin coating. The spin coating is performed at a rotating speed of preferably 1000 to 3000 rpm.

For example, the composition is applied onto, for example, any of substrates (e.g., silicon/silicon dioxide coating, silicon nitride and chromium-vapor-deposited quartz substrate, etc.) for use in the production of precision integrated circuit devices, etc. by appropriate application means, such as a spinner or a coater. The thus applied composition is dried, thereby obtaining an actinic-ray- or radiation-sensitive film (hereinafter also referred to as a photosensitive film). The application of the composition to the substrate can be preceded by the application of a heretofore known antireflection film.

The resultant photosensitive film is exposed to actinic rays or radiation, preferably baked (heated), and developed. Thus, a favorable pattern can be obtained. From the viewpoint of sensitivity and stability, it is preferred for the baking temperature to be in the range of 80 to 150° C., especially 90 to 130° C.

As the actinic rays or radiation, there can be mentioned, for example, infrared light, visible light, ultraviolet light, far-ultraviolet light, extreme ultraviolet light, X-rays or an electron beam. It is preferred for the actinic rays or radiation to have, for example, a wavelength of 250 nm or shorter, especially 220 nm or shorter. As such actinic rays or radiation, there can be mentioned, for example, a KrF excimer laser (248 nm), an ArF excimer laser (193 nm), an $F_2$ excimer laser (157 nm), X-rays or an electron beam. As especially preferred actinic rays or radiation, there can be mentioned an ArF excimer laser, an $F_2$ excimer laser (157 nm), EUV (13 nm) or an electron beam.

The exposure performed in the condition that the interstice between the photosensitive film and a lens is filled with a liquid (for example, pure water) whose refractive index is higher than that of air, namely, liquid-immersion exposure may be carried out in the stage of the exposure to actinic rays or radiation. This liquid-immersion exposure can enhance the resolution. At the liquid-immersion exposure, for the prevention of any contact of the resist film with the immersion liquid, a film that is highly insoluble in the immersion liquid (also referred to as a "top coat") may be disposed on the film and between the film and the immersion liquid. As another means for the prevention of any contact of the film with the immersion liquid, a hydrophobic resin (HR) may be added to the composition in advance.

The hydrophobic resin (HR) will be described below.

In the case of exposure of the film of the composition of the present invention via the liquid immersion medium, a hydrophobic resin (HR) may be further added according to necessity. This would bring about uneven localization of the hydrophobic resin (HR) on the surface layer of the film. When the liquid immersion medium is water, there would be attained an improvement of receding contact angle on the surface of the film with reference to water upon formation of the film. The receding contact angle of the surface of the film can be increased by the addition of the hydrophobic resin (HR). The receding contact angle of the film is preferably in the range of 60° to 90°, more preferably 70° or higher. Although the hydrophobic resin (HR) is unevenly localized on the interface as aforementioned, differing from the surfactant, the hydrophobic resin does not necessarily have to have a hydrophilic group in its molecule and does not need to contribute toward uniform mixing of polar/nonpolar substances.

The receding contact angle refers to a contact angle determined when the contact line at a droplet-substrate interface draws back. It is generally known that the receding contact angle is useful in the simulation of droplet mobility in a dynamic condition. In a simple definition, the receding contact angle can be defined as the contact angle exhibited at the recession of the droplet interface at the time of, after application of a droplet discharged from a needle tip onto a substrate, re-indrawing the droplet into the needle. Generally, the receding contact angle can be measured according to a method of contact angle measurement known as the dilation/contraction method.

In the operation of liquid immersion exposure, it is needed for the liquid for liquid immersion to move on a wafer while tracking the movement of an exposure head involving high-speed scanning on the wafer and thus forming an exposure pattern. Therefore, the contact angle of the liquid for liquid immersion with respect to the resist film in dynamic condition is important, and it is required for the resist to be capable of tracking the high-speed scanning of the exposure head without leaving any droplets.

As the hydrophobic resin (HR) is localized in a surface portion of the film, it is preferred for the same to contain a fluorine atom or a silicon atom. The fluorine atom or silicon atom may be contained in the principal chain of the hydrophobic resin (HR) or may be introduced in a side chain(s) thereof as a substituent.

The hydrophobic resin (HR) is preferably a resin having an alkyl group containing a fluorine atom, a cycloalkyl group containing a fluorine atom or an aryl group containing a fluorine atom as a partial structure containing a fluorine atom.

The alkyl group containing a fluorine atom (preferably having 1 to 10 carbon atoms, more preferably 1 to 4 carbon atoms) is a linear or branched alkyl group having at least one hydrogen atom thereof substituted with a fluorine atom. Further, other substituents may be possessed.

The cycloalkyl group containing a fluorine atom is a cycloalkyl group of a single ring or multiple rings having at least one hydrogen atom thereof substituted with a fluorine atom. Further, other substituents may be contained.

As the aryl group containing a fluorine atom, there can be mentioned one having at least one hydrogen atom of an aryl group, such as a phenyl or naphthyl group, substituted with a fluorine atom. Further, other substituents may be contained.

As preferred alkyl groups containing a fluorine atom, cycloalkyl groups containing a fluorine atom and aryl groups containing a fluorine atom, there can be mentioned groups of the following general formulae (F2) to (F4), which however in no way limit the scope of the present invention.

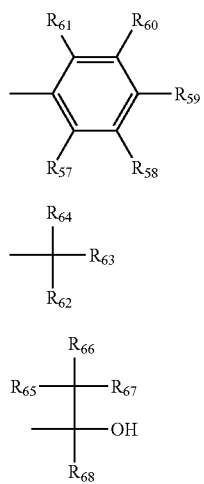

(F2)

(F3)

(F4)

In the general formulae (F2) to (F4), each of $R_{57}$ to $R_{68}$ independently represents a hydrogen atom, a fluorine atom or an alkyl group, provided that at least one of each of $R_{57}$-$R_{61}$, $R_{62}$-$R_{64}$ and $R_{65}$-$R_{68}$ represents a fluorine atom or an alkyl group (preferably having 1 to 4 carbon atoms) having at least one hydrogen atom thereof substituted with a fluorine atom. It is preferred that all of $R_{57}$-$R_{61}$ and $R_{65}$-$R_{67}$ represent fluorine atoms. Each of $R_{62}$, $R_{63}$ and $R_{68}$ preferably represents an alkyl group (especially having 1 to 4 carbon atoms) having at least one hydrogen atom thereof substituted with a fluorine atom, more preferably a perfluoroalkyl group having 1 to 4 carbon atoms. $R_{62}$ and $R_{63}$ may be bonded with each other to thereby form a ring.

Specific examples of the groups of the general formula (F2) include a p-fluorophenyl group, a pentafluorophenyl group, a 3,5-di(trifluoromethyl)phenyl group and the like.

Specific examples of the groups of the general formula (F3) include a trifluoromethyl group, a pentafluoropropyl group, a pentafluoroethyl group, a heptafluorobutyl group, a hexafluoroisopropyl group, a heptafluoroisopropyl group, a hexafluoro(2-methyl)isopropyl group, a nonafluorobutyl group, an octafluoroisobutyl group, a nonafluorohexyl group, a nonafluoro-t-butyl group, a perfluoroisopentyl group, a perfluorooctyl group, a perfluoro(trimethyl)hexyl group, a 2,2,3,3-tetrafluorocyclobutyl group, a perfluorocyclohexyl group and the like. Of these, a hexafluoroisopropyl group, a heptafluoroisopropyl group, a hexafluoro(2-methyl)isopropyl group, an octafluoroisobutyl group, a nonafluoro-t-butyl group and a perfluoroisopentyl group are preferred. A hexafluoroisopropyl group and a heptafluoroisopropyl group are more preferred.

Specific examples of the groups of the general formula (F4) include —C(CF$_3$)$_2$OH, —C(C$_2$F$_5$)$_2$OH, —C(CF$_3$)(CF$_3$)OH, —CH(CF$_3$)OH and the like. —C(CF$_3$)$_2$OH is preferred.

Specific examples of the repeating units having a fluorine atom will be shown below, which however in no way limit the scope of the present invention.

In the specific examples, $X_1$ represents a hydrogen atom, —CH$_3$, —F or —CF$_3$. $X_2$ represents —F or —CF$_3$.

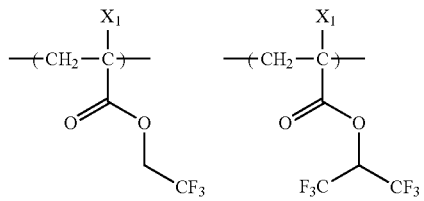

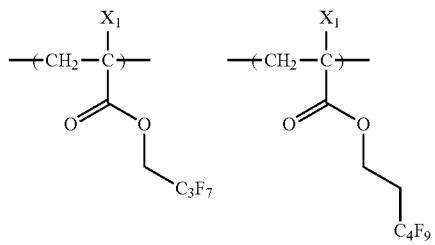

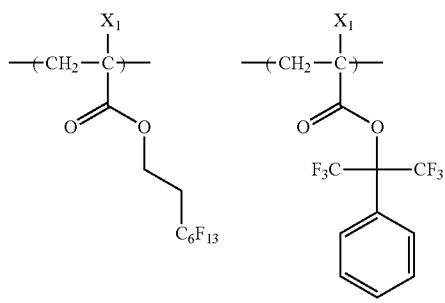

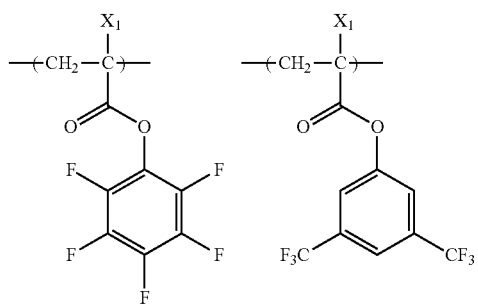

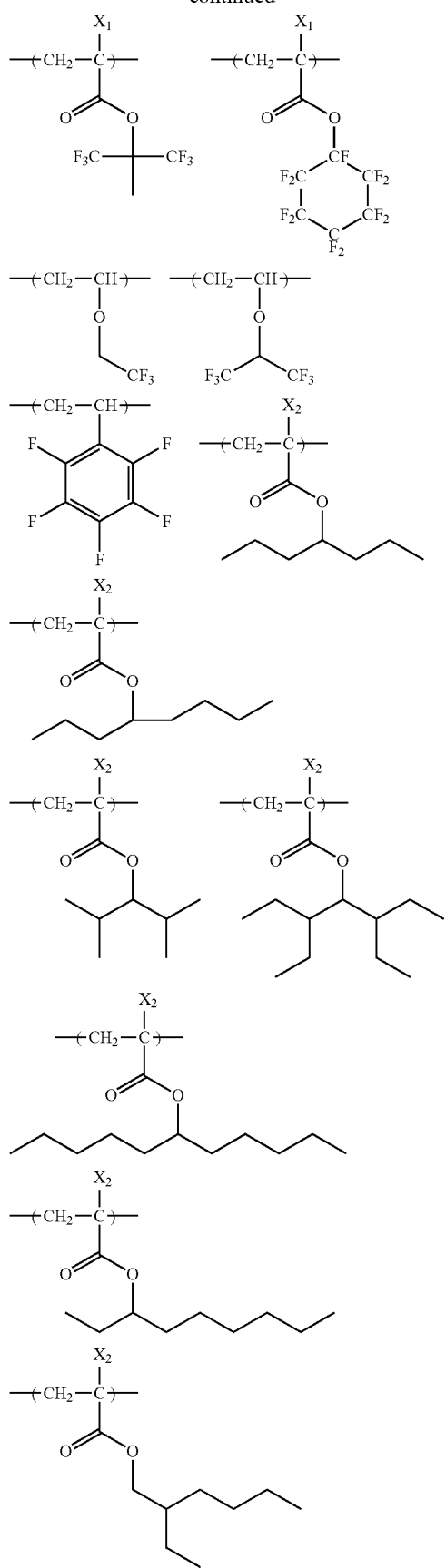

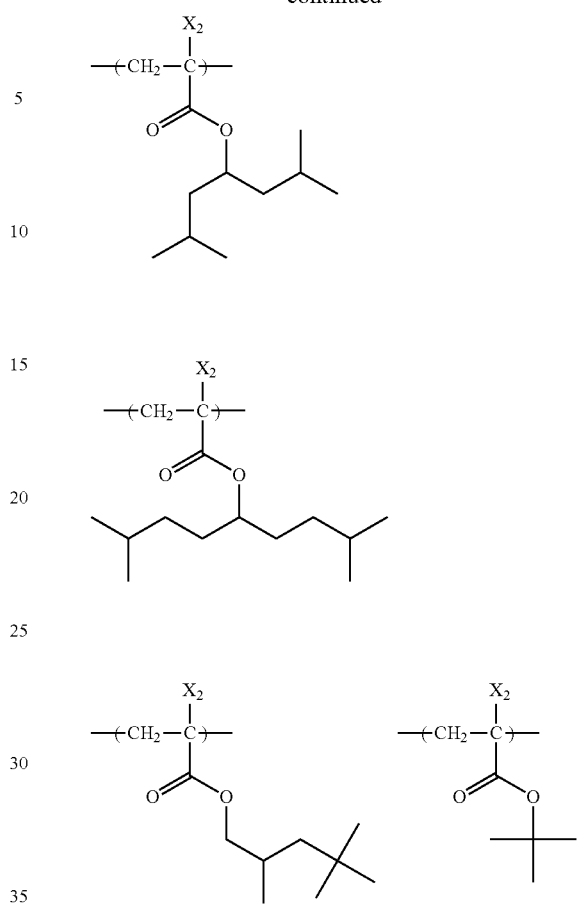

When the hydrophobic resin (HR) has a silicon atom, the hydrophobic resin (HR) is preferably a resin having an alkylsilyl structure (preferably a trialkylsilyl group) or a cyclosiloxane structure as a partial structure having a silicon atom.

As the alkylsilyl structure or cyclosiloxane structure, there can be mentioned, for example, any of the groups of the following general formulae (CS-1) to (CS-3) or the like.

(CS-1)

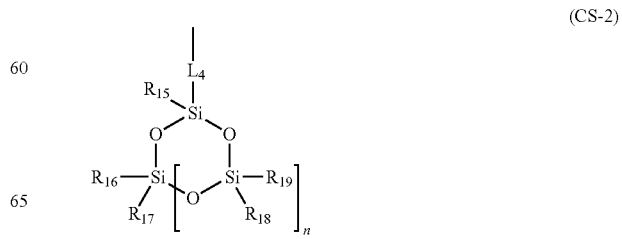
(CS-2)

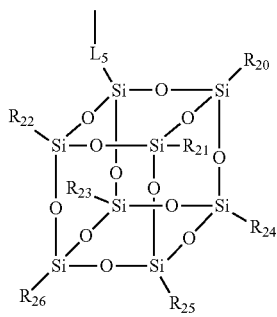

(CS-3)

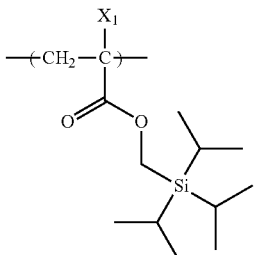

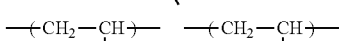

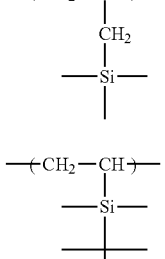

In the general formulae (CS-1) to (CS-3), each of $R_{12}$ to $R_{26}$ independently represents a linear or branched alkyl group (preferably having 1 to 20 carbon atoms) or a cycloalkyl group (preferably having 3 to 20 carbon atoms).

Each of $L_3$ to $L_5$ represents a single bond or a bivalent connecting group. As the bivalent connecting group, there can be mentioned any one or a combination of two or more groups selected from the group consisting of an alkylene group, a phenylene group, an ether group, a thioether group, a carbonyl group, an ester group, an amido group, a urethane group and a urea group.

In the formulae, n is an integer of 1 to 5, preferably an integer of 2 to 4.

Specific examples of the repeating units having the groups of the general formulae (CS-1) to (CS-3) will be shown below, which however in no way limit the scope of the present invention. In the specific examples, $X_1$ represents a hydrogen atom, —$CH_3$, —F or —$CF_3$.

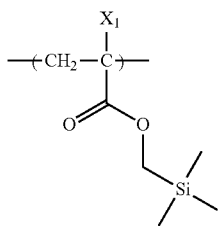 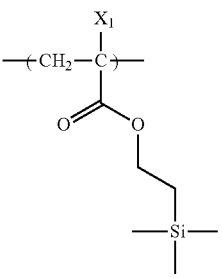

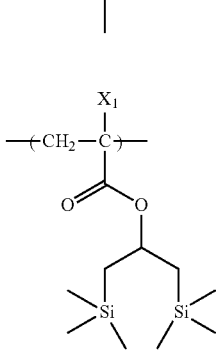

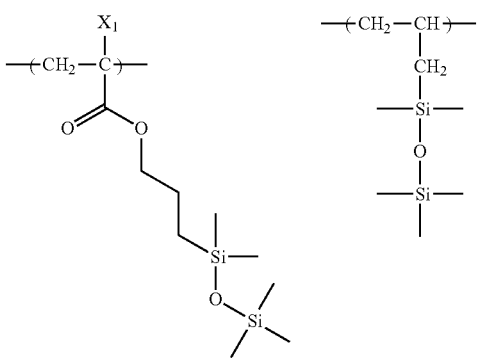

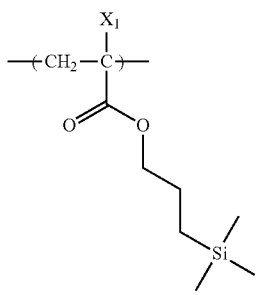 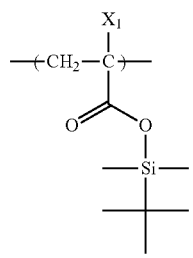

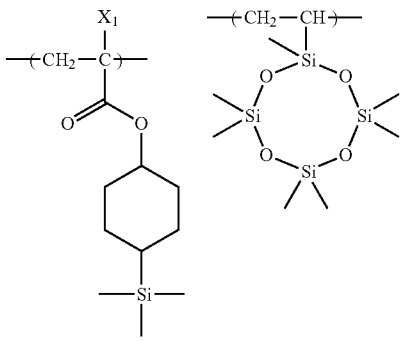

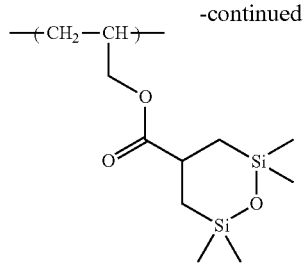
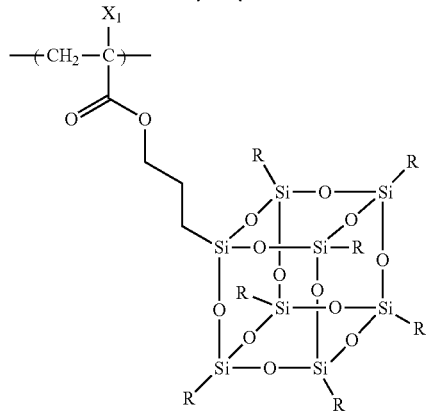

R = CH₃, C₂H₅, C₃H₇, C₄H₉

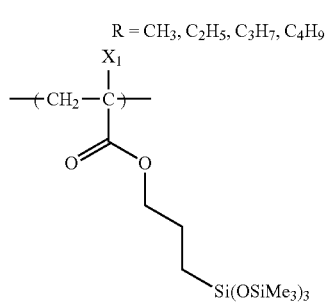

Moreover, the hydrophobic resin (HR) may have at least one group selected from among the following groups (x) to (z):

(x) an alkali soluble group,
(y) a group that is decomposed by the action of an alkali developer, resulting in an increase of solubility in the alkali developer, and
(z) a group that is decomposed by the action of an acid.

As the alkali soluble group (x), there can be mentioned a phenolic hydroxyl group, a carboxylate group, a fluoroalcohol group, a sulfonate group, a sulfonamido group, a sulfonylimido group, an (alkylsulfonyl)(alkylcarbonyl)methylene group, an (alkylsulfonyl)(alkylcarbonyl)imido group, a bis (alkylcarbonyl)methylene group, a bis(alkylcarbonyl)imido group, a bis(alkylsulfonyl)methylene group, a bis(alkylsulfonyl)imido group, a tris(alkylcarbonyl)methylene group, a tris (alkylsulfonyl)methylene group and the like.

As preferred alkali soluble groups, there can be mentioned a fluoroalcohol group (preferably hexafluoroisopropanol), a sulfonimido group and a bis(carbonyl)methylene group.

As the repeating unit having an alkali soluble group (x), preferred use is made of any of a repeating unit resulting from direct bonding of an alkali soluble group to the principal chain of a resin like a repeating unit of acrylic acid or methacrylic acid, a repeating unit resulting from bonding, via a connecting group, of an alkali soluble group to the principal chain of a resin and a repeating unit resulting from polymerization with the use of a chain transfer agent or polymerization initiator having an alkali soluble group to thereby introduce the same in a polymer chain terminal.

The content of repeating units having an alkali soluble group (x) is preferably in the range of 1 to 50 mol %, more preferably 3 to 35 mol % and still more preferably 5 to 20 mol % based on all the repeating units of the polymer.

Specific examples of the repeating units having an alkali soluble group (x) will be shown below, which however in no way limit the scope of the present invention.

In the formulae, Rx represents H, CH₃, CF₃ or CH₂OH.

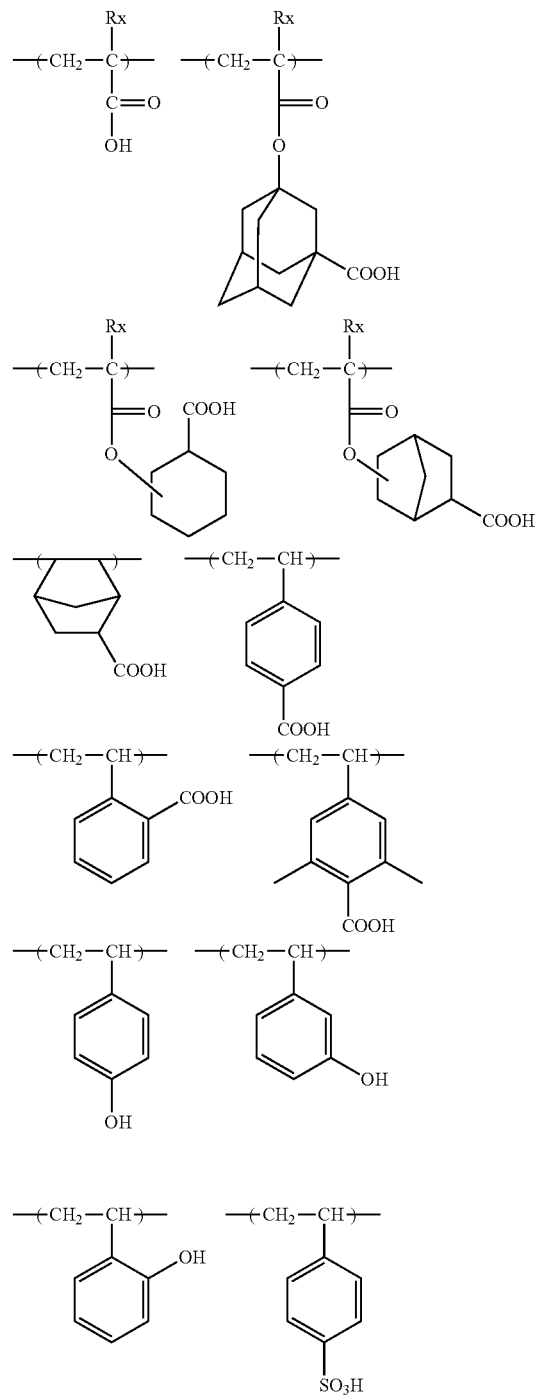

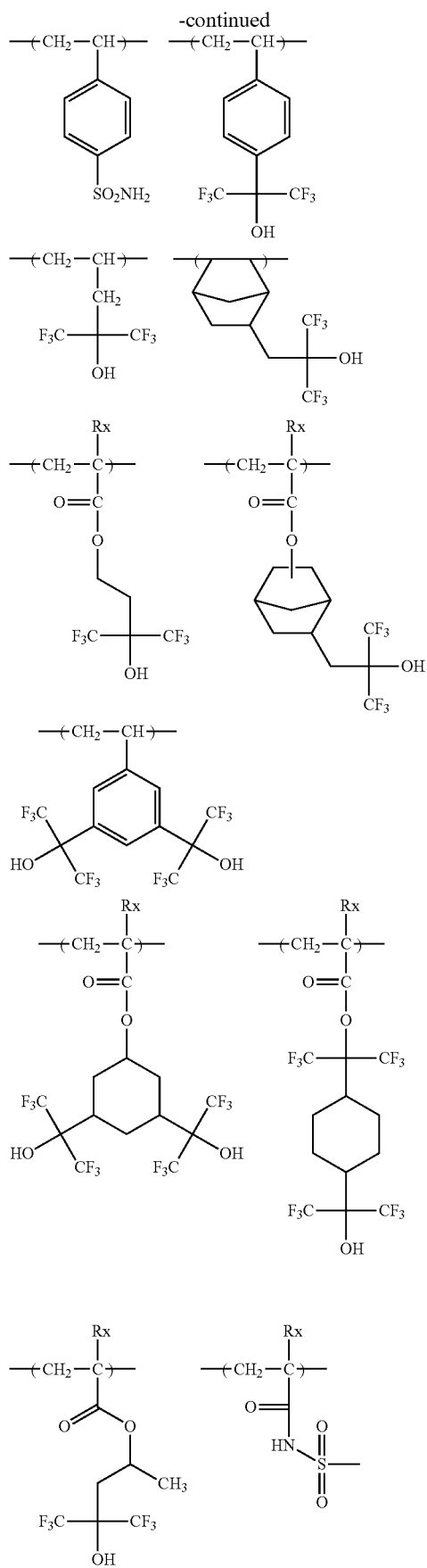
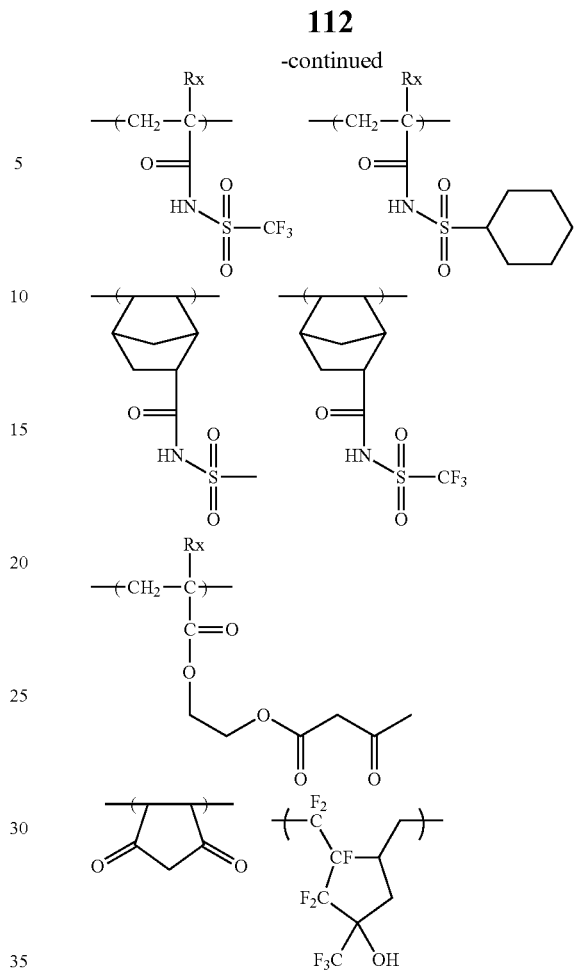

As the group (y) that is decomposed by the action of an alkali developer, resulting in an increase of solubility in the alkali developer, there can be mentioned, for example, a group having a lactone structure, an acid anhydride group, an acid imide group or the like. A group having a lactone structure is preferred.

As the repeating unit having a group (y) that is decomposed by the action of an alkali developer, resulting in an increase of solubility in the alkali developer, preferred use is made of both of a repeating unit resulting from bonding of a group (y) that is decomposed by the action of an alkali developer, resulting in an increase of solubility in the alkali developer, to the principal chain of a resin such as a repeating unit of acrylic ester or methacrylic ester, and a repeating unit resulting from polymerization with the use of a chain transfer agent or polymerization initiator having a group (y) resulting in an increase of solubility in an alkali developer to thereby introduce the same in a polymer chain terminal.

The content of repeating units having a group (y) resulting in an increase of solubility in an alkali developer is preferably in the range of 1 to 40 mol %, more preferably 3 to 30 mol % and still more preferably 5 to 15 mol % based on all the repeating units of the polymer.

As specific examples of the repeating units having a group (y) resulting in an increase of solubility in an alkali developer, there can be mentioned those similar to the repeating units having a lactone structure set forth with respect to the resins as the component (B).

As the repeating unit having a group (z) that is decomposed by the action of an acid in the hydrophobic resin (HR), there can be mentioned those similar to the repeating units having an acid decomposable group set forth with respect to the resin (B). The content of repeating units having a group (z) that is decomposed by the action of an acid in the hydrophobic resin (HR) is preferably in the range of 1 to 80 mol %, more preferably 10 to 80 mol % and still more preferably 20 to 60 mol % based on all the repeating units of the polymer.

The hydrophobic resin (HR) may further have any of the repeating units of general formula (III) below.

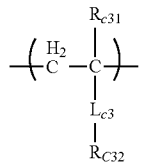
(III)

In general formula (III), $R_{c31}$ represents a hydrogen atom, an alkyl group, an alkyl group substituted with a fluorine atom, a cyano group or —$CH_2$—O-$Rac_2$ group, wherein $Rac_2$ represents a hydrogen atom, an alkyl group or an acyl group. $R_{c31}$ is preferably a hydrogen atom, a methyl group, a hydroxymethyl group or a trifluoromethyl group, especially preferably a hydrogen atom or a methyl group.

$R_{c32}$ represents a group having any of an alkyl group, a cycloalkyl group, an alkenyl group, a cycloalkenyl group and an aryl group. These groups may optionally be substituted with a fluorine atom or a silicon atom.

$L_{c3}$ represents a single bond or a bivalent connecting group.

In general formula (III), the alkyl group represented by $R_{c32}$ is preferably a linear or branched alkyl group having 3 to 20 carbon atoms.

The cycloalkyl group is preferably a cycloalkyl group having 3 to 20 carbon atoms.

The alkenyl group is preferably an alkenyl group having 3 to 20 carbon atoms.

The cycloalkenyl group is preferably a cycloalkenyl group having 3 to 20 carbon atoms.

The aryl group is preferably a phenyl group or a naphthyl group having 6 to 20 carbon atoms. These groups may have a substituent.

Preferably, $R_{c32}$ represents an unsubstituted alkyl group or an alkyl group substituted with a fluorine atom.

The bivalent connecting group represented by $L_{c3}$ is preferably an alkylene group (preferably having 1 to 5 carbon atoms), an oxy group, a phenylene group or an ester bond (group of the formula —COO—).

Further, the hydrophobic resin (HR) may preferably have any of the repeating units of general formula (CII-AB) below.

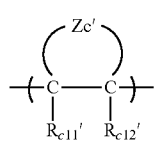
(CII-AB)

In the general formula (CII-AB), each of $R_{c11'}$ and $R_{c12'}$ independently represents a hydrogen atom, a cyano group, a halogen atom or an alkyl group.

Zc' represents an atomic group for forming an alicyclic structure which contains two bonded carbon atoms (C—C).

Specific examples of the repeating units of the general formula (III) and general formula (CII-AB) will be shown below, which however in no way limit the scope of the present invention. In the formulae, Ra represents H, $CH_3$, $CH_2OH$, $CF_3$ or CN.

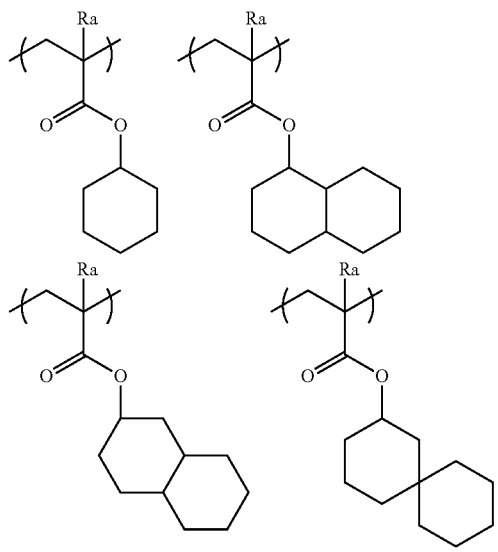

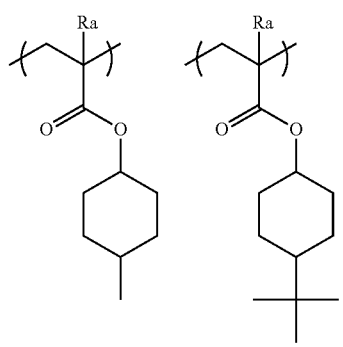

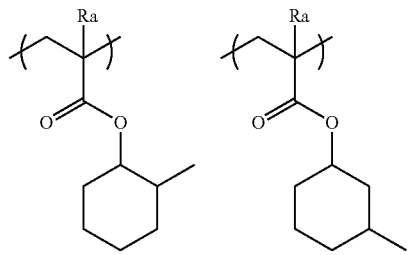

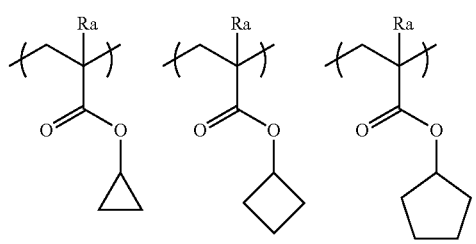

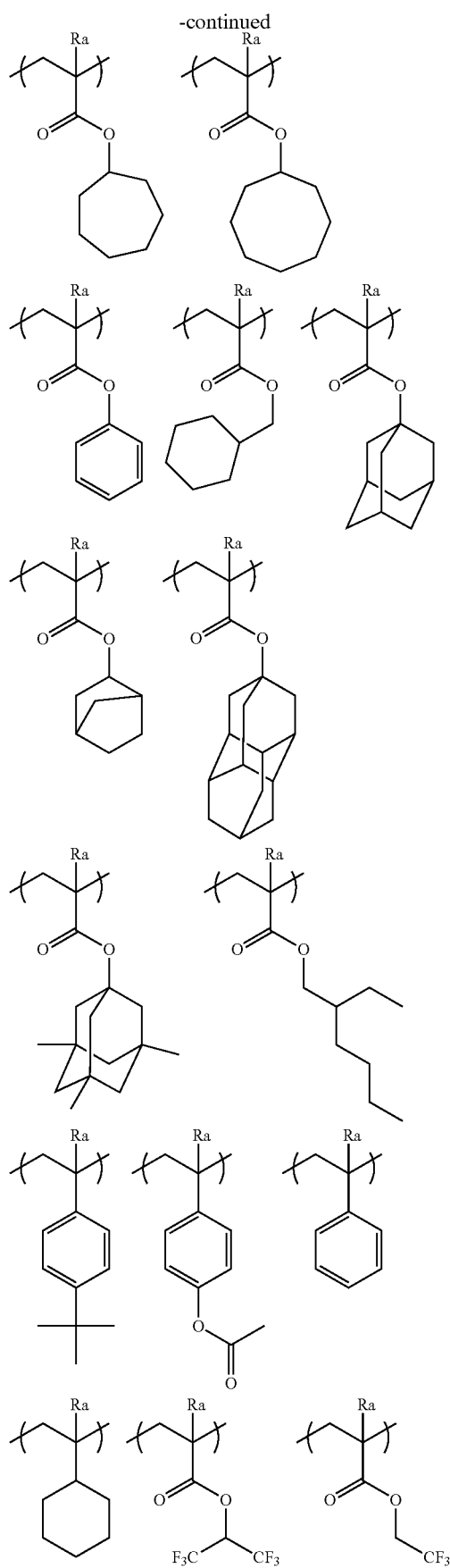
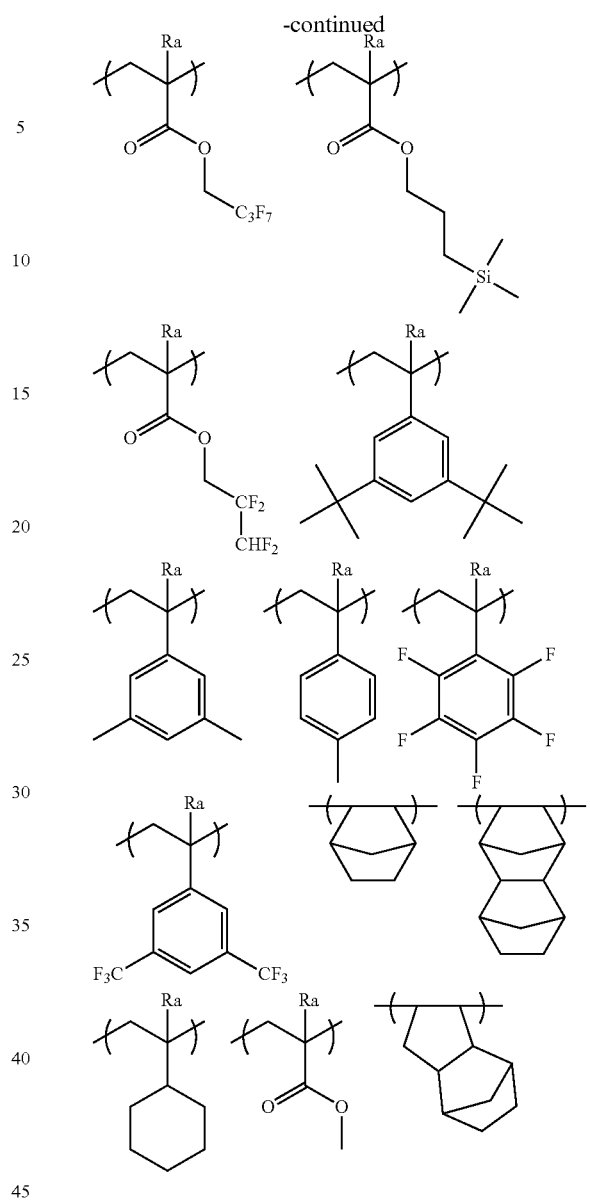

When the hydrophobic resin (HR) has a fluorine atom, the content of fluorine atom(s) is preferably in the range of 5 to 80 mass %, more preferably 10 to 80 mass %, based on the molecular weight of the hydrophobic resin (HR). The repeating unit containing a fluorine atom preferably exists in the hydrophobic resin (HR) in an amount of 10 to 100 mass %, more preferably 30 to 100 mass %.

When the hydrophobic resin (HR) has a silicon atom, the content of silicon atom(s) is preferably in the range of 2 to 50 mass %, more preferably 2 to 30 mass %, based on the molecular weight of the hydrophobic resin (HR). The repeating unit containing a silicon atom preferably exists in the hydrophobic resin (HR) in an amount of 10 to 100 mass %, more preferably 20 to 100 mass %.

The weight average molecular weight of the hydrophobic resin (HR) in terms of standard polystyrene molecular weight is preferably in the range of 1000 to 100,000, more preferably 1000 to 50,000 and still more preferably 2000 to 15,000.

The content of the hydrophobic resin (HR) in the composition is in the range or 0.01 to 10 mass %, more preferably 0.05 to 8 mass % and still more preferably 0.1 to 5 mass % based on the total solid of the composition of the present invention.

Impurities, such as metals, should naturally be of low quantity in the hydrophobic resin (HR), as for the resin (B). The content of residual monomers and oligomer components is preferably 0 to 10 mass %, more preferably 0 to 5 mass % and still more preferably 0 to 1 mass %. Accordingly, there can be obtained a resist being free from a change of in-liquid foreign matter, sensitivity, etc. over time. From the viewpoint of resolving power, resist profile, side wall of resist pattern, roughness, etc., the molecular weight distribution (Mw/Mn, also referred to as the degree of dispersal) thereof is preferably in the range of 1 to 5, more preferably 1 to 3 and still more preferably 1 to 2.

A variety of commercially available products can be used as the hydrophobic resin (HR), and also the resin can be synthesized in accordance with conventional methods (for example, radical polymerization). As general synthesizing methods, there can be mentioned, for example, a batch polymerization method in which a monomer species and an initiator are dissolved in a solvent and heated to thereby carry out polymerization, a dropping polymerization method in which a solution of monomer species and initiator is dropped into a hot solvent over a period of 1 to 10 hours, and the like. The dropping polymerization method is preferred. As a reaction solvent, there can be mentioned, for example, an ether such as tetrahydrofuran, 1,4-dioxane or diisopropyl ether, a ketone such as methyl ethyl ketone or methyl isobutyl ketone, an ester solvent such as ethyl acetate, an amide solvent such as dimethylformamide or dimethylacetamide, or the aforementioned solvent capable of dissolving the composition of the present invention, such as propylene glycol monomethyl ether acetate, propylene glycol monomethyl ether or cyclohexanone. Preferably, the polymerization is carried out with the use of the same solvent as that used in the composition of the present invention. This would inhibit any particle generation during storage.

The polymerization reaction is preferably carried out in an atmosphere consisting of an inert gas, such as nitrogen or argon. In the initiation of polymerization, a commercially available radical initiator (azo initiator, peroxide, etc.) is used as the polymerization initiator. Among the radical initiators, an azo initiator is preferred, and azo initiators having an ester group, a cyano group and a carboxyl group are more preferred. As specific preferred initiators, there can be mentioned azobisisobutyronitrile, azobisdimethylvaleronitrile, dimethyl 2,2'-azobis(2-methylpropionate) and the like. The reaction concentration is in the range of 5 to 50 mass %, preferably 30 to 50 mass %. The reaction temperature is generally in the range of 10° to 150° C., preferably 30° to 120° C. and more preferably 60° to 100° C.

After the completion of the reaction, the mixture is allowed to stand still to cool to room temperature and purified. In the purification, use is made of routine methods, such as a liquid-liquid extraction method in which residual monomers and oligomer components are removed by water washing or by the use of a combination of appropriate solvents, a method of purification in solution form such as ultrafiltration capable of extraction removal of only components of a given molecular weight or below, a re-precipitation method in which a resin solution is dropped into a poor solvent to thereby coagulate the resin in the poor solvent and thus remove residual monomers, etc. and a method of purification in solid form such as washing of a resin slurry obtained by filtration with the use of a poor solvent. For example, the reaction solution is brought into contact with a solvent wherein the resin is poorly soluble or insoluble (poor solvent) amounting to 10 or less, preferably 10 to 5 times the volume of the reaction solution to thereby precipitate the resin as a solid.

The solvent for use in the operation of precipitation or re-precipitation from a polymer solution (precipitation or re-precipitation solvent) is not limited as long as the solvent is a poor solvent for the polymer. According to the type of polymer, use can be made of any one appropriately selected from among a hydrocarbon, a halogenated hydrocarbon, a nitro compound, an ether, a ketone, an ester, a carbonate, an alcohol, a carboxylic acid, water, a mixed solvent containing these solvents and the like. Of these, it is preferred to employ a solvent containing at least an alcohol (especially methanol and the like) or water as the precipitation or re-precipitation solvent.

The amount of precipitation or re-precipitation solvent used is generally in the range of 100 to 10,000 parts by mass, preferably 200 to 2000 parts by mass and more preferably 300 to 1000 parts by mass per 100 parts by mass of the polymer solution, according to intended efficiency, yield, etc.

The temperature at which the precipitation or re-precipitation is carried out is generally in the range of about 0° to 50° C., preferably about room temperature (for example, about 20° to 35° C.), according to efficiency and operation easiness. The operation of precipitation or re-precipitation can be carried out by a publicly known method, such as a batch or continuous method, with the use of a common mixing vessel, such as an agitation vessel.

The polymer obtained by the precipitation or re-precipitation is generally subjected to common solid/liquid separation, such as filtration or centrifugal separation, and dried before use. The filtration is carried out with the use of a filter medium ensuring solvent resistance, preferably under pressure. The drying is performed at about 30° to 100° C., preferably about 30° to 50° C. at ordinary pressure or reduced pressure (preferably reduced pressure).

Alternatively, after the resin precipitation and separation, the obtained resin may be once more dissolved in a solvent and brought into contact with a solvent wherein the resin is poorly soluble or insoluble. Specifically, the method may include the steps of, after the completion of the radical polymerization reaction, bringing the polymer into contact with a solvent wherein the polymer is poorly soluble or insoluble to thereby precipitate a resin (step a), separating the resin from the solution (step b), re-dissolving the resin in a solvent to thereby obtain a resin solution (A) (step c), thereafter bringing the resin solution (A) into contact with a solvent wherein the resin is poorly soluble or insoluble amounting to less than 10 times (preferably 5 times or less) the volume of the resin solution (A) to thereby precipitate a resin solid (step d) and separating the precipitated resin (step e).

Specific examples of the hydrophobic resins (HR) will be shown below. The following Table 3 shows the molar ratio of individual repeating units (corresponding to individual repeating units in order from the left), weight average molecular weight and degree of dispersal with respect to each of the resins.

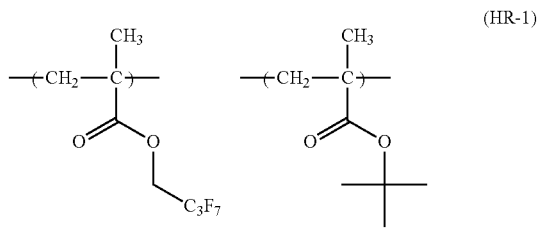

(HR-1)

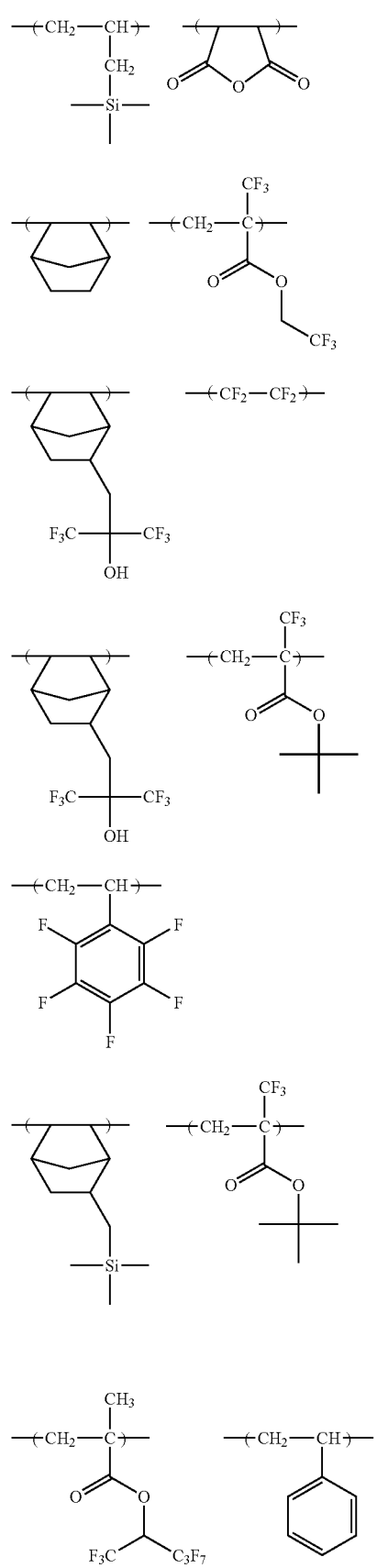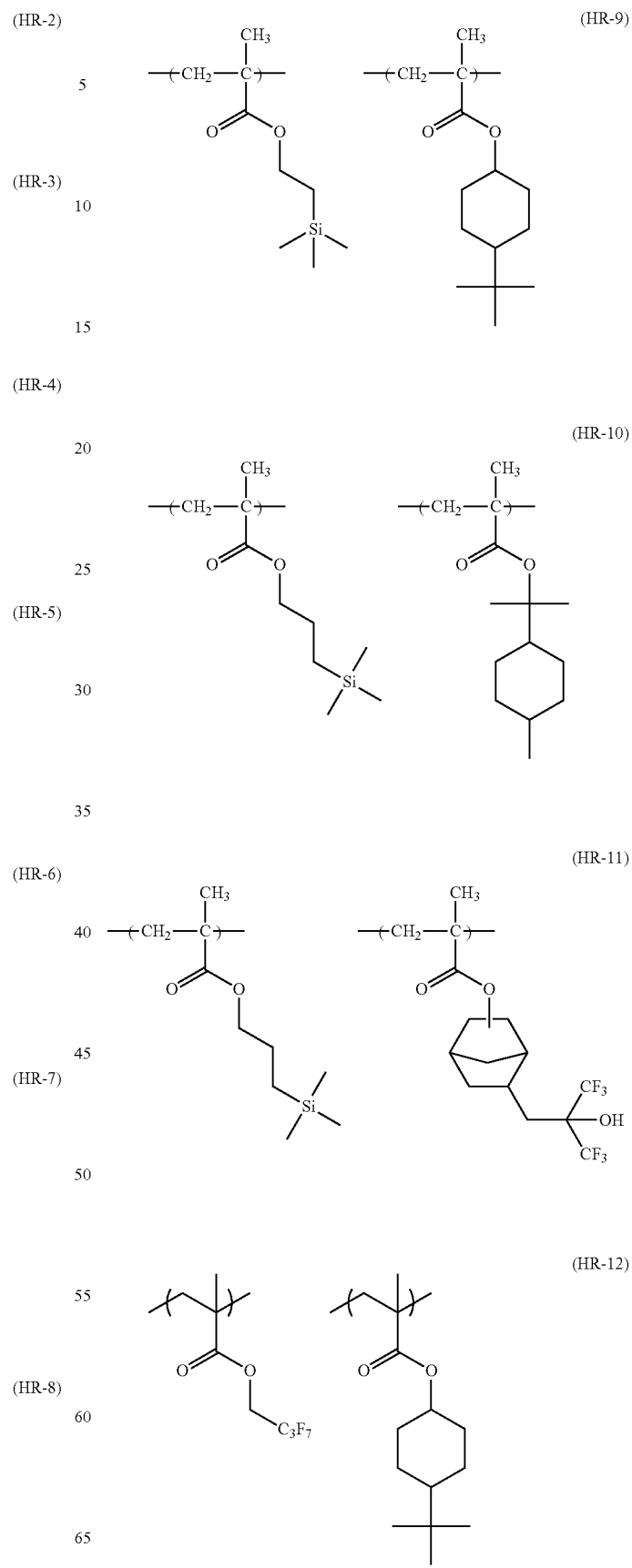

(HR-13) 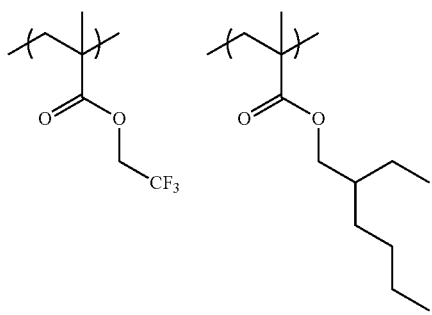
(HR-14) 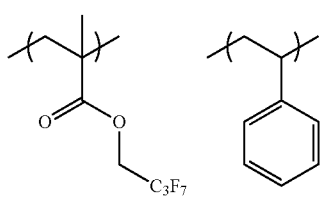
(HR-15) 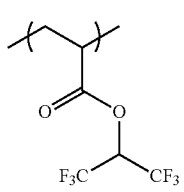
(HR-16) 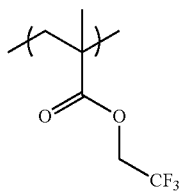
(HR-17) 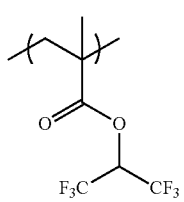
(HR-18) 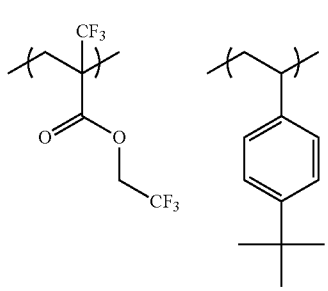
(HR-19) 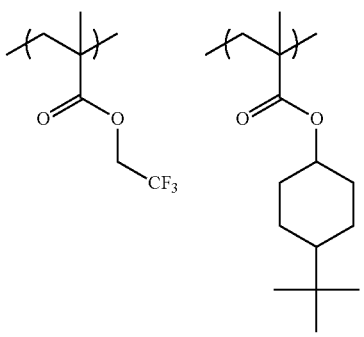
(HR-20) 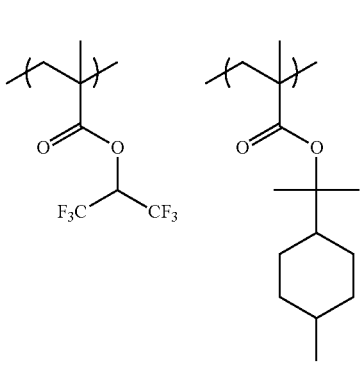
(HR-21) 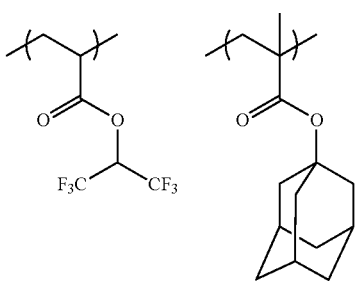
(HR-22) 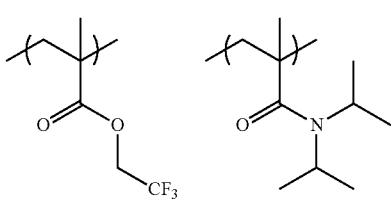
(HR-23) 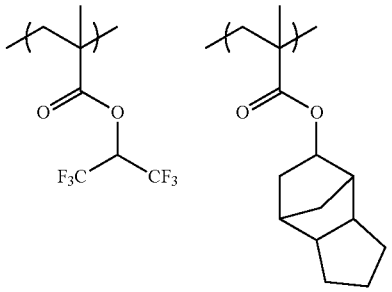

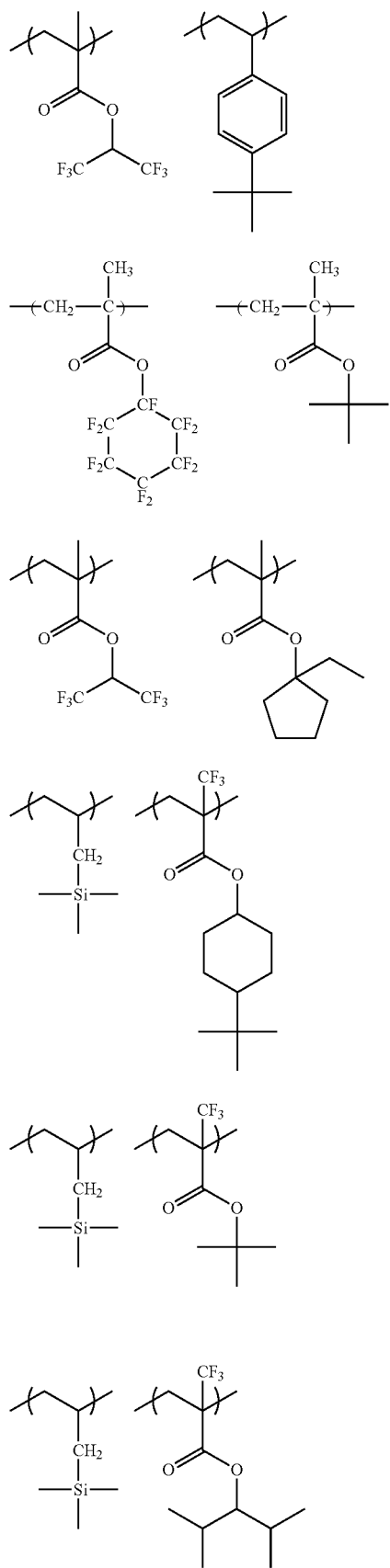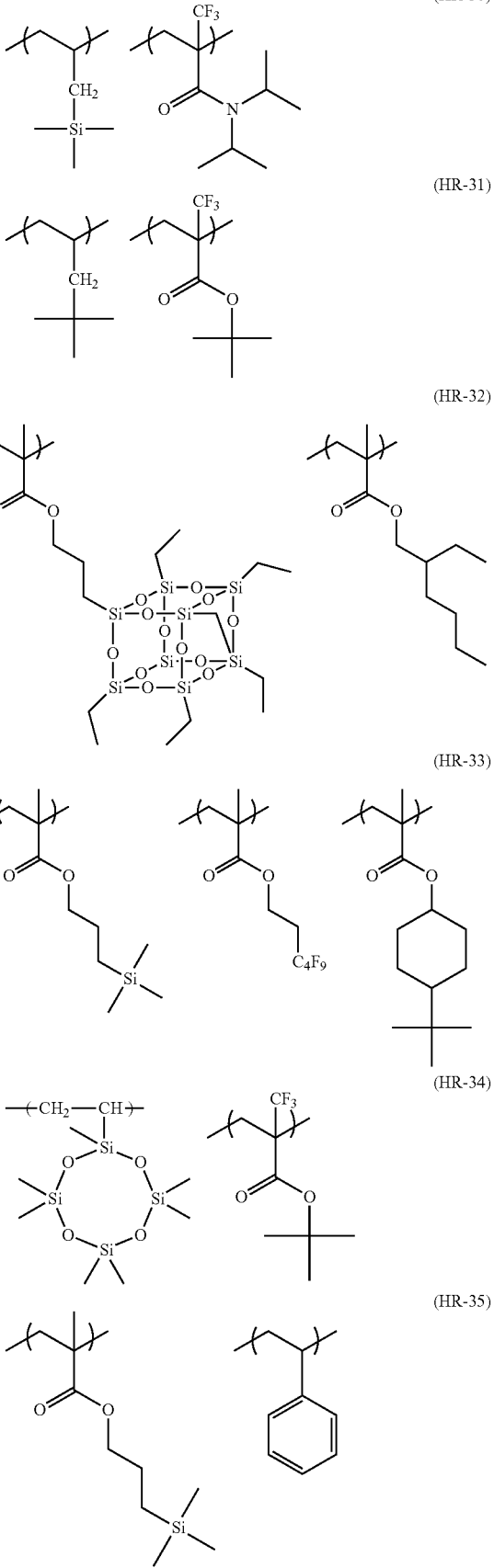

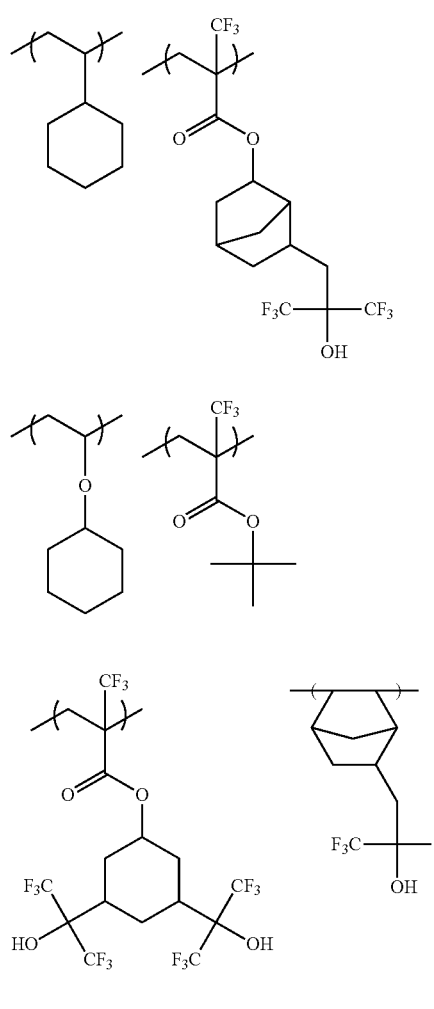
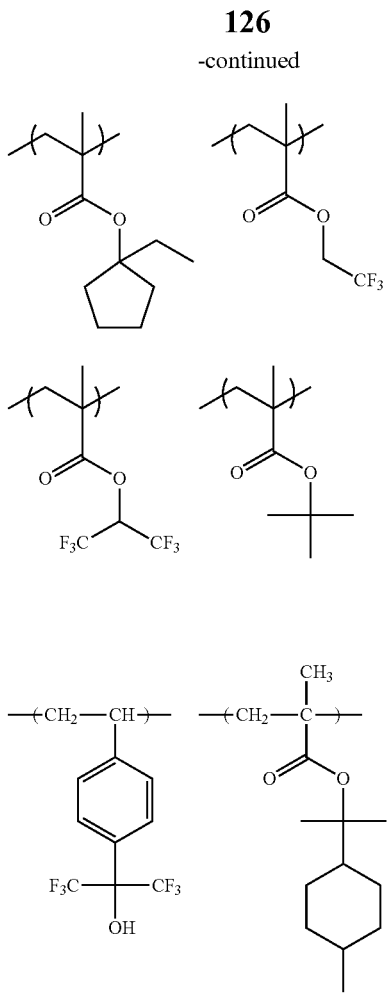
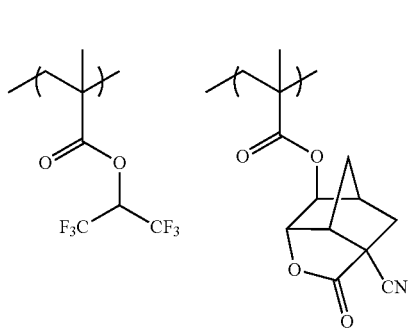
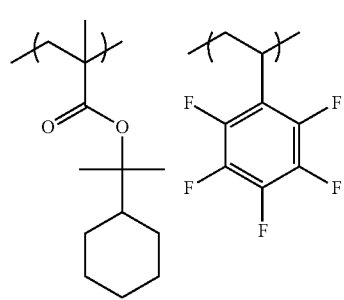

(HR-46)
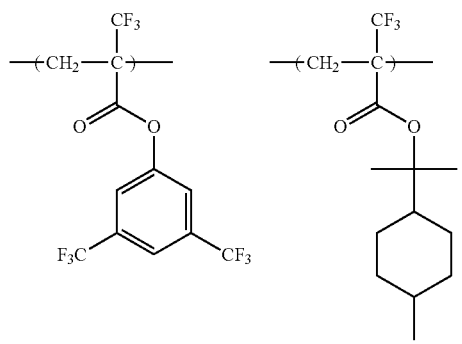
(HR-47)
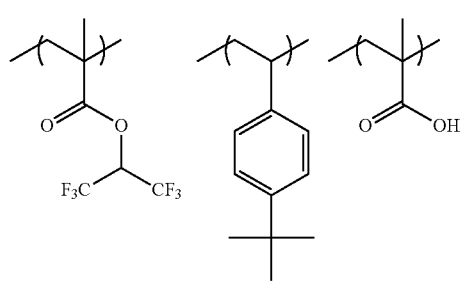
(HR-48)
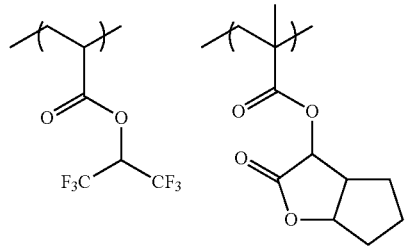
(HR-49)
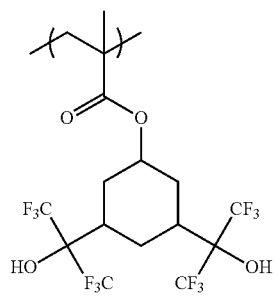
(HR-50)
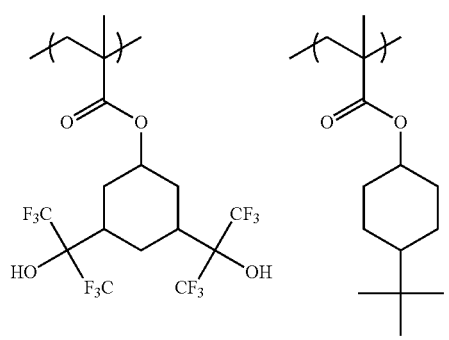
(HR-51)
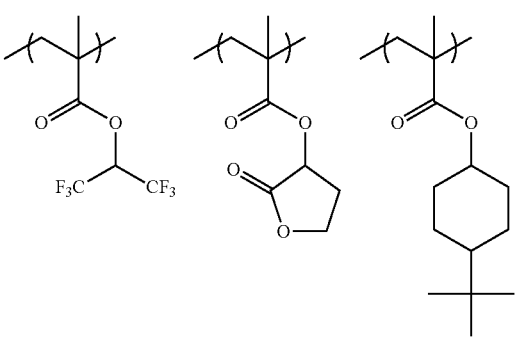
(HR-52)
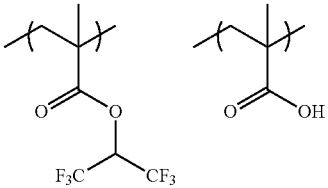
(HR-53)
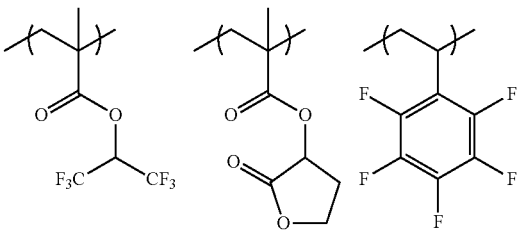
(HR-54)
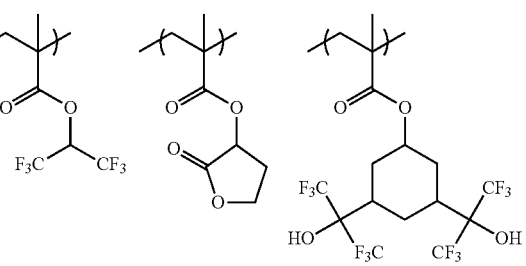
(HR-55)
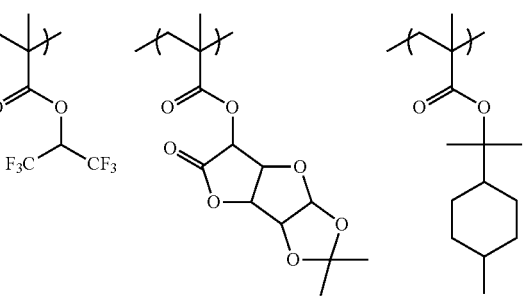

(HR-56)
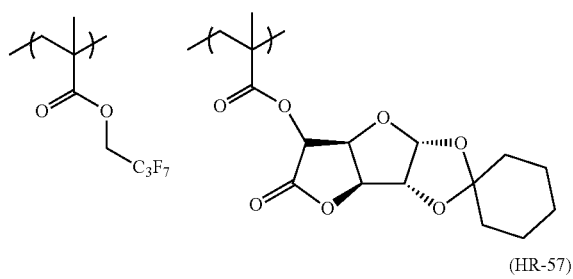
(HR-57)
(HR-58)
(HR-59)
(HR-60)
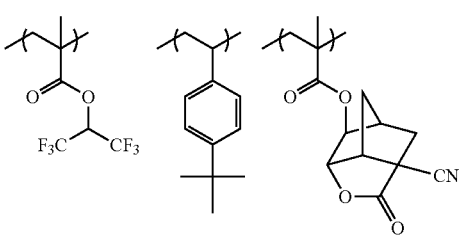
(HR-61)
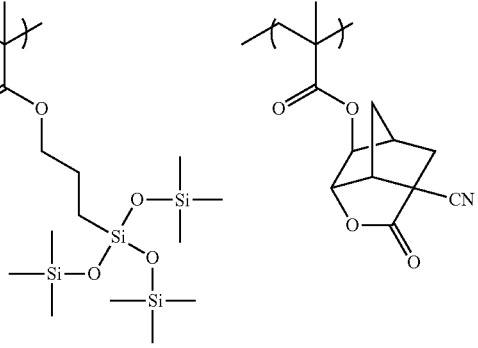
(HR-62)
(HR-63)
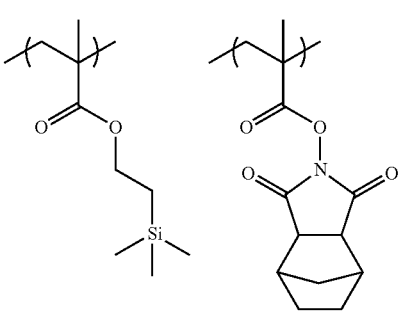
(HR-64)
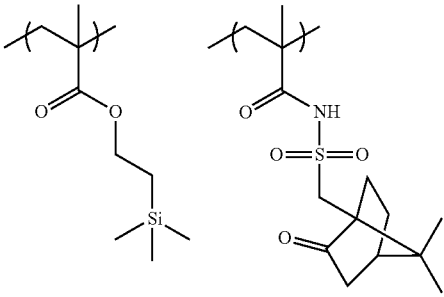
(HR-65)
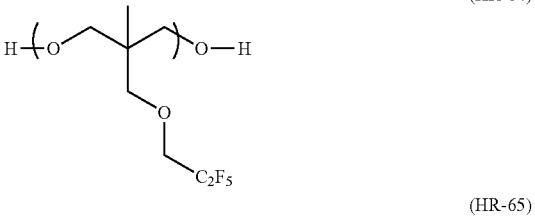
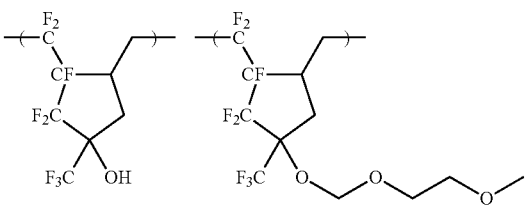
TABLE 3
| Resin | Comp. | Mw | Mw/Mn |
|---|---|---|---|
| HR-1 | 50/50 | 4900 | 1.4 |
| HR-2 | 50/50 | 5100 | 1.6 |
| HR-3 | 50/50 | 4800 | 1.5 |
| HR-4 | 50/50 | 5300 | 1.6 |

TABLE 3-continued

| Resin | Comp. | Mw | Mw/Mn |
|---|---|---|---|
| HR-5 | 50/50 | 4500 | 1.4 |
| HR-6 | 100 | 5500 | 1.6 |
| HR-7 | 50/50 | 5800 | 1.9 |
| HR-8 | 50/50 | 4200 | 1.3 |
| HR-9 | 50/50 | 5500 | 1.8 |
| HR-10 | 40/60 | 7500 | 1.6 |
| HR-11 | 70/30 | 6600 | 1.8 |
| HR-12 | 40/60 | 3900 | 1.3 |
| HR-13 | 50/50 | 9500 | 1.8 |
| HR-14 | 50/50 | 5300 | 1.6 |
| HR-15 | 100 | 6200 | 1.2 |
| HR-16 | 100 | 5600 | 1.6 |
| HR-17 | 100 | 4400 | 1.3 |
| HR-18 | 50/50 | 4300 | 1.3 |
| HR-19 | 50/50 | 6500 | 1.6 |
| HR-20 | 30/70 | 6500 | 1.5 |
| HR-21 | 50/50 | 6000 | 1.6 |
| HR-22 | 50/50 | 3000 | 1.2 |
| HR-23 | 50/50 | 5000 | 1.5 |
| HR-24 | 50/50 | 4500 | 1.4 |
| HR-25 | 30/70 | 5000 | 1.4 |
| HR-26 | 50/50 | 5500 | 1.6 |
| HR-27 | 50/50 | 3500 | 1.3 |
| HR-28 | 50/50 | 6200 | 1.4 |
| HR-29 | 50/50 | 6500 | 1.6 |
| HR-30 | 50/50 | 6500 | 1.6 |
| HR-31 | 50/50 | 4500 | 1.4 |
| HR-32 | 30/70 | 5000 | 1.6 |
| HR-33 | 30/30/40 | 6500 | 1.8 |
| HR-34 | 50/50 | 4000 | 1.3 |
| HR-35 | 50/50 | 6500 | 1.7 |
| HR-36 | 50/50 | 6000 | 1.5 |
| HR-37 | 50/50 | 5000 | 1.6 |
| HR-38 | 50/50 | 4000 | 1.4 |
| HR-39 | 20/80 | 6000 | 1.4 |
| HR-40 | 50/50 | 7000 | 1.4 |
| HR-41 | 50/50 | 6500 | 1.6 |
| HR-42 | 50/50 | 5200 | 1.6 |
| HR-43 | 50/50 | 6000 | 1.4 |
| HR-44 | 70/30 | 5500 | 1.6 |
| HR-45 | 50/20/30 | 4200 | 1.4 |
| HR-46 | 30/70 | 7500 | 1.6 |
| HR-47 | 40/58/2 | 4300 | 1.4 |
| HR-48 | 50/50 | 6800 | 1.6 |
| HR-49 | 100 | 6500 | 1.5 |
| HR-50 | 50/50 | 6600 | 1.6 |
| HR-51 | 30/20/50 | 6800 | 1.7 |
| HR-52 | 95/5 | 5900 | 1.6 |
| HR-53 | 40/30/30 | 4500 | 1.3 |
| HR-54 | 50/30/20 | 6500 | 1.8 |
| HR-55 | 30/40/30 | 7000 | 1.5 |
| HR-56 | 60/40 | 5500 | 1.7 |
| HR-57 | 40/40/20 | 4000 | 1.3 |
| HR-58 | 60/40 | 3800 | 1.4 |
| HR-59 | 80/20 | 7400 | 1.6 |
| HR-60 | 40/40/15/5 | 4800 | 1.5 |
| HR-61 | 60/40 | 5600 | 1.5 |
| HR-62 | 50/50 | 5900 | 2.1 |
| HR-63 | 80/20 | 7000 | 1.7 |
| HR-64 | 100 | 5500 | 1.8 |
| HR-65 | 50/50 | 9500 | 1.9 |

The liquid for liquid immersion for use in the liquid immersion exposure will now be described.

The liquid for liquid immersion preferably consists of a liquid being transparent in exposure wavelength whose temperature coefficient of refractive index is as low as possible so as to ensure minimization of any distortion of optical image projected on the resist film. Especially in the use of an ArF excimer laser (wavelength: 193 nm) as an exposure light source, however, it is more preferred to use water from not only the above viewpoints but also the viewpoints of easy procurement and easy handling.

Further, from the viewpoint of refractive index increase, use can be made of a medium of 1.5 or higher refractive index. Such a medium may be an aqueous solution or an organic solvent.

In the use of water as a liquid for liquid immersion, a slight proportion of additive (liquid) that would not dissolve the resist film on a wafer and would be negligible with respect to its influence on an optical coat for an under surface of lens element may be added in order to not only decrease the surface tension of water but also increase a surface activating power. The additive is preferably an aliphatic alcohol with a refractive index approximately equal to that of water, for example, methyl alcohol, ethyl alcohol, isopropyl alcohol or the like. The addition of an alcohol with a refractive index approximately equal to that of water is advantageous in that even when the alcohol component is evaporated from water to thereby cause a change of content concentration, the change of refractive index of the liquid as a whole can be minimized. On the other hand, when a substance being opaque in 193 nm rays or an impurity whose refractive index is greatly different from that of water is mixed therein, the mixing would invite a distortion of optical image projected on the resist film. Accordingly, it is preferred to use distilled water as the liquid immersion water. Furthermore, use may be made of pure water having been filtered through an ion exchange filter or the like.

Desirably, the electrical resistance of the water is 18.3 MΩcm or higher, and the TOC (organic matter concentration) thereof is 20 ppb or below. Prior deaeration of the water is desired.

Raising the refractive index of the liquid for liquid immersion would enable an enhancement of lithography performance. From this viewpoint, an additive suitable for refractive index increase may be added to the water, or heavy water ($D_2O$) may be used in place of water.

For the prevention of direct contact of a film with a liquid for liquid immersion, a film that is highly insoluble in the liquid for liquid immersion (hereinafter also referred to as a "top coat") may be provided between the film from the photosensitive composition of the present invention and the liquid for liquid immersion. The functions to be fulfilled by the top coat are applicability to an upper layer portion of the resist, transparency in radiation of especially 193 nm and being highly insoluble in the liquid for liquid immersion. Preferably, the top coat does not mix with the resist and is uniformly applicable to an upper layer of the resist.

From the viewpoint of 193 nm transparency, the top coat preferably consists of a polymer not abundantly containing an aromatic moiety. As such, there can be mentioned, for example, a hydrocarbon polymer, an acrylic ester polymer, polymethacrylic acid, polyacrylic acid, polyvinyl ether, a siliconized polymer, a fluoropolymer or the like. The aforementioned hydrophobic resins (HR) also find appropriate application in the top coat. From the viewpoint of contamination of an optical lens by leaching of impurities from the top coat into the liquid for liquid immersion, it is preferred to reduce the amount of residual monomer components of the polymer contained in the top coat.

At the detachment of the top coat, use may be made of a developer, or a separate peeling agent may be used. The peeling agent preferably consists of a solvent having a lower permeation into the film. Detachability by an alkali developer is preferred from the viewpoint of simultaneous attainment of the detachment step with the development processing step for the film. The top coat is preferred to be acidic from the viewpoint of detachment with the use of an alkali developer.

However, from the viewpoint of non-intermixability with the film, the top coat may be neutral or alkaline.

The less the difference in refractive index between the top coat and the liquid for liquid immersion, the higher the resolving power. In an ArF excimer laser (wavelength: 193 nm), when water is used as the liquid for liquid immersion, the top coat for ArF liquid immersion exposure preferably has a refractive index close to that of the liquid for liquid immersion. From the viewpoint of approximation of the refractive index to that of the liquid for liquid immersion, it is preferred for the top coat to contain a fluorine atom. From the viewpoint of transparency and refractive index, it is preferred to reduce the thickness of the film.

Preferably, the top coat does not mix with the resist film and also does not mix with the liquid for liquid immersion. From this viewpoint, when the liquid for liquid immersion is water, it is preferred for the solvent used in the top coat to be highly insoluble in the solvent used in the positive resist composition and be a non-water-soluble medium. When the liquid for liquid immersion is an organic solvent, the top coat may be soluble or insoluble in water.

The development step will be described below.

In the development step, an alkali developer is generally used.

As the alkali developer, use can be made of any of alkaline aqueous solutions of an inorganic alkali such as sodium hydroxide, potassium hydroxide, sodium carbonate, sodium silicate, sodium metasilicate or aqueous ammonia, a primary amine such as ethylamine or n-propylamine, a secondary amine such as diethylamine or di-n-butylamine, a tertiary amine such as triethylamine or methyldiethylamine, an alcoholamine such as dimethylethanolamine or triethanolamine, a quaternary ammonium salt such as tetramethylammonium hydroxide or tetraethylammonium hydroxide, a cycloamine such as pyrrole or piperidine, or the like.

Before the use of the above alkali developer, appropriate amounts of an alcohol and/or a surfactant may be added thereto.

The alkali concentration of the alkali developer is generally in the range of 0.1 to 20 mass %. The pH value of the alkali developer is generally in the range of 10.0 to 15.0.

With respect to the particulars of the process for fabricating an imprint mold using the composition of the present invention, reference can be made to, for example, Japanese Patent No. 4109085, JP-A-2008-162101, and "Fundamentals of nanoimprint and its technology development/application deployment—technology of nanoimprint substrate and its latest technology deployment" edited by Yoshihiko Hirai, published by Frontier Publishing.

The present invention will be described in greater detail below by way of its examples. However, the gist of the present invention is in no way limited to these examples.

<Synthesis of Acid Generator A1>

(1) Synthesis of Compound A1-1

A Grignard reagent was prepared through routine procedure from 100.7 g of 3-methoxybromobenzene and 13.7 g of magnesium using 400 ml of THF as a solvent. Subsequently, 12.8 g of thionyl chloride was dropped into the Grignard reagent at 0° C. and agitated for an hour. Thereafter, 29.2 g of trimethylsilyl chloride was dropped into the mixture at 0° C. and agitated for two hours. The thus obtained reaction solution was poured into 200 ml of 12% aqueous HBr solution, thereby terminating the reaction. Then, 100 ml of toluene was poured into the obtained reaction solution, and extracted with 100 ml of 12% aqueous HBr solution twice. The whole water phase was washed with 50 ml of toluene twice and extracted with 100 ml of chloroform three times. The whole chloroform phase was dried over anhydrous magnesium sulfate, and the solvent was distilled off. The resultant liquid was dissolved in 100 ml of methanol, and 40.0 g of sodium 2,4,6-tricyclohexylbenzenesulfonate was added to the solution and agitated for two hours. The solvent was distilled off, and ethyl acetate was added to the residue. The thus obtained organic phase was sequentially washed with a saturated aqueous sodium hydrogen carbonate solution and water. The solvent was distilled off, thereby obtaining 60.5 g of desired white solid compound (A1-1).

$^1$H-NMR (300 MHz, CDCl$_3$) δ=7.71 (t, J=2.1 Hz, 3H), 7.47 (t, J=8.1 Hz, 3H), 7.20-7.12 (m, 6H), 6.97 (s, 2H), 4.37-4.22 (m, 2H), 3.83 (s, 9H), 2.43-2.37 (m, 1H), 1.98-1.15 (m, 30H).

(2) Synthesis of Compound A1-2

Compound A1-2 amounting to 38.9 g was obtained in the same manner as in the synthesis of compound A1-1 except that 100.7 g of 3-methoxybromobenzene was changed to 61.2 g of 4-methoxybromobenzene.

$^1$H-NMR (300 MHz, CDCl$_3$) δ=7.73 (d, J=6.9 Hz, 6H), 7.12 (d, J=6.9 Hz, 6H), 6.98 (s, 2H), 4.31-4.25 (m, 2H), 3.84 (s, 9H), 2.43-2.38 (m, 1H), 1.99-1.18 (m, 30H).

(3) Synthesis of Compound A1-12

A Grignard reagent was prepared through routine procedure from 12.5 g of 2,4,6-methoxybromobenzene and 1.4 g of magnesium using 50 ml of THF as a solvent. Subsequently, 11.4 g of diphenyl sulfoxide was dropped into the Grignard reagent at 0° C. and agitated for an hour. Thereafter, 5.0 g of trimethylsilyl chloride was dropped into the mixture at 0° C. and agitated for two hours. The thus obtained reaction solution was poured into 50 ml of 12% aqueous HBr solution, thereby terminating the reaction. Then, 50 ml of toluene was poured into the obtained reaction solution, and extracted with 10 ml of 12% aqueous HBr solution twice. The whole water phase was washed with 10 ml of toluene twice and extracted with 20 ml of chloroform three times. The whole chloroform phase was dried over anhydrous magnesium sulfate, and the solvent was distilled off. The resultant liquid was dissolved in 100 ml of methanol, and 15.0 g of sodium 2,4,6-tricyclohexylbenzenesulfonate was added to the solution and agitated for two hours. The solvent was distilled off, and ethyl acetate was added to the residue. The thus obtained organic phase was sequentially washed with a saturated aqueous sodium hydrogen carbonate solution and water. The solvent was distilled off, thereby obtaining 20.5 g of desired white solid compound (A1-12).

$^1$H-NMR (300 MHz, CDCl$_3$) δ=7.70-7.54 (m, 10H), 6.95 (s, 2H), 6.49 (s, 2H), 4.35-4.20 (m, 2H), 4.00 (s, 3H), 3.86 (s, 6H), 2.48-2.35 (m, 1H), 2.00-1.20 (m, 30H).

(4) Synthesis of Compound A1-13

Compound A1-13 amounting to 4.9 g was obtained in the same manner as in the synthesis of compound A1-1 except that 100.7 g of 3-methoxybromobenzene was changed to 11.5 g of 4-ethoxybromobenzene.

$^1$H-NMR (300 MHz, CDCl$_3$) δ=7.73 (d, J=6.9 Hz, 6H), 7.08 (d, J=6.9 Hz, 6H), 6.98 (s, 2H), 4.38-4.24 (m, 2H), 4.06 (q, J=12.9 Hz, 6H), 2.44-2.37 (m, 1H), 2.05-1.18 (m, 30H) 1.41 (t, J=12.9 Hz, 9H).

(5) Synthesis of compound A1-15

Compound A1-15 amounting to 5.9 g was obtained in the same manner as in the synthesis of compound A1-1 except that 100.7 g of 3-methoxybromobenzene was changed to 15.2 g of 3-cyclohexyloxybromobenzene.

(6) Synthesis of Compound A1-16

Compound A1-16 amounting to 20.8 g was obtained in the same manner as in the synthesis of compound A1-12 except that 11.4 g of diphenyl sulfoxide was changed to 10.0 g of dibenzothiopheneoxide.

(7) Synthesis of Compound A1-19

Compound A1-19 amounting to 19.5 g was obtained in the same manner as in the synthesis of compound A1-12 except that 11.4 g of diphenyl sulfoxide was changed to 10.0 g of phenoxathiinoxide.

(8) Synthesis of Compound A1-24

Compound A1-24 amounting to 7.5 g was obtained in the same manner as in the synthesis of compound A1-1 except that 40.0 g of sodium 2,4,6-tricyclohexylbenzenesulfonate was changed to 5.0 g of sodium 2,4,6-triisopropylbenzenesulfonate.

(9) Synthesis of Compound A1-31

Compound A1-31 amounting to 7.5 g was obtained in the same manner as in the synthesis of compound A1-1 except that 40.0 g of sodium 2,4,6-tricyclohexylbenzenesulfonate was changed to 5.0 g of sodium 2,4,6-tritert-butylbenzenesulfonate.

(10) Synthesis of Compound A1-35

First, 20.0 g of 2,4,6-tricyclohexylbromobenzene was dissolved in 800 ml of diethyl ether. In a nitrogen atmosphere, 6.0 g of tetramethylethylenediamine and 31.9 ml of n-butyllithium (1.63M hexane solution) were added to the solution at 0° C., and agitated at 0° C. for an hour. The resultant reaction solution was dropped into a solution obtained by dissolving 15.7 g of 1,1,2,2,3,3-hexafluoropropane-1,3-disulfonyl difluoride in 200 ml of diethyl ether at 0° C. over a period of 30 minutes. After the completion of dropping, the mixture was further agitated for 30 minutes, and 200 ml of distilled water was added thereto. The thus obtained organic phase was washed with saturated saline twice. The solvent was removed, and 100 ml of methanol and 100 ml of 1N aqueous sodium hydroxide solution were added to the residue and agitated for an hour. Methanol was distilled off, and ethyl acetate was added to the residue. The thus obtained organic phase was washed with saturated saline twice. The solvent was distilled off, and the thus obtained solid was washed with hexane. The resultant solid was dissolved in 100 ml of methanol, and 10.0 g of below-shown sulfonium salt A was added to the solution and agitated for two hours. The solvent was distilled off, and ethyl acetate was added to the residue. The thus obtained organic phase was sequentially washed with a saturated aqueous sodium hydrogen carbonate solution and water. The solvent was distilled off, thereby obtaining 23.5 g of desired white solid compound (A1-35).

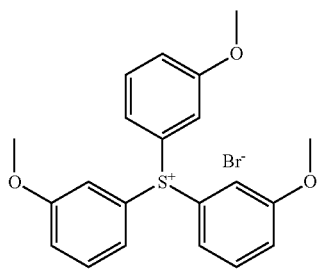

(A)

(11) Synthesis of Compound A1-38

Compound A1-38 amounting to 19.4 g was obtained in the same manner as in the synthesis of compound A1-35 except that 10.0 g of sulfonium salt A was changed to 10.0 g of below-shown sulfonium salt B.

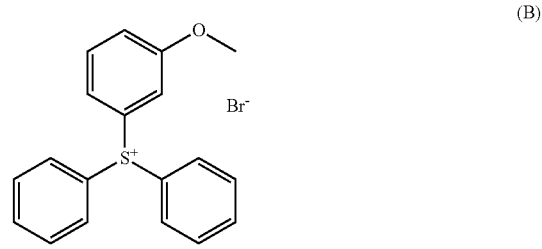 [SMILES: COc1cccc([S+](c2ccccc2)c2ccccc2)c1 ; [Br-]]

(B)

(12) Synthesis of Compound A1-50

Compound A1-50 amounting to 14.8 g was obtained in the same manner as in the synthesis of compound A1-35 except that 20.0 g of 2,4,6-tricyclohexylbromobenzene was changed to 20.0 g of 2,4,6-triisopropylbromobenzene.

(13) Synthesis of Compound A1-54

First, 20.0 g of 2,4,6-tricyclohexylbromobenzene was dissolved in 800 ml of diethyl ether. In a nitrogen atmosphere, 6.0 g of tetramethylethylenediamine and 31.9 ml of n-butyllithium (1.63M hexane solution) were added to the solution at 0° C., and agitated at 0° C. for an hour. The resultant reaction solution was dropped into a solution obtained by dissolving 15.7 g of 1,1,2,2,3,3-hexafluoropropane-1,3-disulfonyl difluoride in 200 ml of diethyl ether at 0° C. over a period of 30 minutes. After the completion of dropping, the mixture was further agitated for 30 minutes, and 10 ml of triethylamine and 4.50 g of trifluorosulfonamide were added thereto. The mixture was agitated at 0° C. for an hour, and 200 ml of distilled water was added thereto. The thus obtained organic phase was washed with saturated saline twice. The solvent was removed, and 100 ml of methanol and 100 ml of 1N aqueous sodium hydroxide solution were added to the residue and agitated for an hour. Methanol was distilled off, and ethyl acetate was added to the residue. The thus obtained organic phase was washed with saturated saline twice. The solvent was distilled off, and the thus obtained solid was washed with hexane. The resultant solid was dissolved in 100 ml of methanol, and 10.0 g of sodium 2,4,6-tricyclohexylbenzenesulfonate was added to the solution and agitated for two hours. The solvent was distilled off, and ethyl acetate was added to the residue. The thus obtained organic phase was sequentially washed with a saturated aqueous sodium hydrogen carbonate solution and water. The solvent was distilled off, thereby obtaining 21.2 g of desired white solid compound (A1-54).

(14) Synthesis of compound A1-64

Compound A1-64 amounting to 12.8 g was obtained in the same manner as in the synthesis of compound A1-35 except that 20.0 g of 2,4,6-tricyclohexylbromobenzene was changed to 10.0 g of piperidine and that 10.0 g of sulfonium salt A was changed to 10.0 g of below-shown sulfonium salt C.

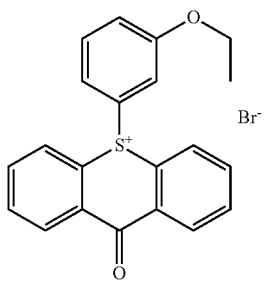

(C)

(15) Synthesis of Compound A1-69

First, 10.0 g of 2,4,6-tricyclohexylphenol was dissolved in 400 ml of THF. In a nitrogen atmosphere, 18.7 ml of n-butyllithium (1.65M hexane solution) was added to the solution at 0° C., and agitated at 0° C. for an hour. The resultant reaction solution was dropped into a solution obtained by dissolving 9.28 g of 1,1,2,2,3,3-hexafluoropropane-1,3-disulfonyl difluoride in 100 ml of THF at 0° C. over a period of 30 minutes. After the completion of dropping, the mixture was further agitated for 30 minutes, and 100 ml of distilled water and 200 ml of ethyl acetate were added thereto. The thus obtained organic phase was washed with saturated saline twice. The solvent was distilled off, and 100 ml of methanol and 200 ml of 1N aqueous sodium hydroxide solution were added to the residue and agitated for an hour. Methanol was distilled off, and 200 ml of ethyl acetate was added to the residue. The thus obtained organic phase was washed with saturated saline twice. The solvent was distilled off, and the thus obtained solid was dissolved in 100 ml of methanol. Then, 10.0 g of sulfonium salt A mentioned above was added to the solution and agitated for an hour. The solvent was distilled off, and ethyl acetate was added to the residue. The thus obtained organic phase was sequentially washed with a saturated aqueous sodium hydrogen carbonate solution and water. The solvent was distilled off, thereby obtaining 17.5 g of desired compound (A1-69).

$^1$H-NMR (300 MHz, CDCl$_3$) δ=7.57 (t, J=7.8 Hz, 3H), 7.42 (t, J=2.1 Hz, 3H), 7.24 (m, 3H), 7.10 (m, 3H), 6.97 (m, 3H), 3.87 (s, 9H), 2.98 (m, 2H), 2.44 (m, 1H), 1.93-1.19 (m, 30H).

$^{19}$F-NMR (300 MHz, CDCl$_3$) δ=−138.3 (t, 2F), −144.4 (t, 2F), −148.5 (s, 2F).

(16) Synthesis of Compound A1-70

Compound A1-70 amounting to 7.8 g was obtained in the same manner as in the synthesis of compound A1-69 except that 10.0 g of sulfonium salt A was changed to 5.0 g of below-shown sulfonium salt D.

(D)

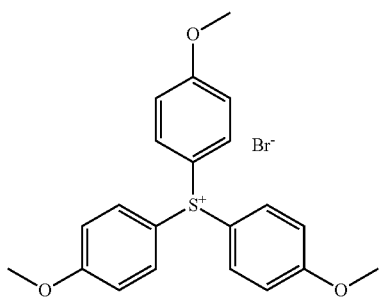

(17) Synthesis of Compound A1-79

Compound A1-79 amounting to 6.9 g was obtained in the same manner as in the synthesis of compound A1-69 except that 10.0 g of sulfonium salt A was changed to 5.0 g of below-shown sulfonium salt E.

(E)

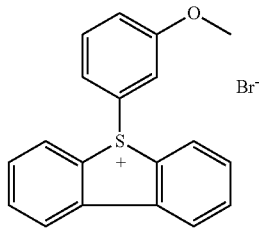

(18) Synthesis of Compound A1-83

Compound A1-83 amounting to 5.2 g was obtained in the same manner as in the synthesis of compound A1-69 except that 10.0 g of sulfonium salt A was changed to 5.0 g of below-shown sulfonium salt F.

(F)

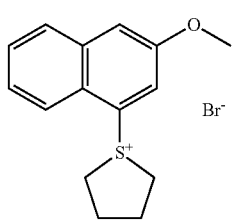

(19) Synthesis of Compound A1-91

Compound A1-91 amounting to 6.3 g was obtained in the same manner as in the synthesis of compound A1-69 except that 10.0 g of 2,4,6-tricyclohexylphenol was changed to 5.0 g of 2,6-diisopropylphenol.

(20) Synthesis of Compound A1-96

First, 10.0 g of 2,4,6-tricyclohexylphenol was dissolved in 400 ml of THF. In a nitrogen atmosphere, 18.7 ml of n-butyllithium (1.65M hexane solution) was added to the solution at 0° C. and agitated at 0° C. for an hour. The resultant reaction solution was dropped into a solution obtained by dissolving 9.28 g of 1,1,2,2,3,3-hexafluoropropane-1,3-disulfonyl difluoride in 100 ml of THF at 0° C. over a period of 30 minutes. After the completion of dropping, the mixture was further agitated for 30 minutes, and 10 ml of triethylamine and 4.50 g of trifluorosulfonamide were added thereto. The mixture was agitated at 0° C. for an hour, and 200 ml of distilled water was added thereto. The thus obtained organic phase was washed with saturated saline twice. The solvent was distilled off, and the thus obtained solid was dissolved in 100 ml of methanol. Triphenylsulfonium bromide A amounting to 10 g was added to the solution and agitated for two hours. The solvent was distilled off, and the thus obtained solid was dissolved in 100 ml of methanol. The above-mentioned sulfonium salt A amounting to 10 g was added to the solution and agitated for an hour. The solvent was distilled off, and ethyl acetate was added to the residue. The thus obtained organic phase was sequentially washed with a saturated aqueous sodium hydrogen carbonate solution and water. The solvent was distilled off, thereby obtaining 11.5 g of desired compound (A1-96).

(21) Synthesis of Compound A1-98

Compound A1-98 amounting to 7.3 g was obtained in the same manner as in the synthesis of compound A1-96 except that 10.0 g of the above-mentioned sulfonium salt A was changed to 5.0 g of below-shown sulfonium salt G.

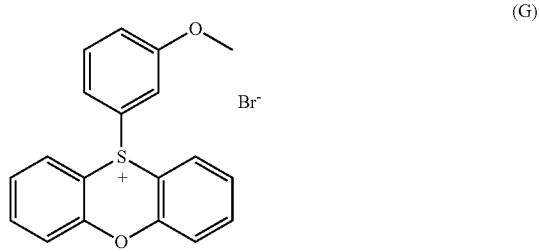

(G)

EXAMPLE A

Examples 1A to 15A and Comparative Examples 1A to 5A

<Preparation of Resist>

Referring to Table 4 below, with respect to each of the resists, the individual components were dissolved in the solvent, thereby obtaining a solution of 4.0 mass % solid content. This solution was passed through a polytetrafluoroethylene filter of 0.03 μm pore size, thereby obtaining a positive resist solution. The thus prepared positive resist solutions were evaluated by the following methods, and the results are given in Table 4.

<Evaluation of Resist>

An organic antireflection film ARC29A (produced by Nissan Chemical Industries, Ltd.) was applied onto a silicon wafer and baked at 205° C. for 60 seconds, thereby forming a 78 nm-thick antireflection film. Each of the prepared positive resist compositions was applied thereonto and baked at 130° C. for 60 seconds, thereby forming a 120 nm-thick resist film. The resultant wafer was exposed through a 6% half-tone mask of 75 nm 1:1 line and space pattern by means of an ArF excimer laser scanner (manufactured by ASML, PAS5500/1100, NA0.75). Thereafter, the exposed wafer was baked at 130° C. for 60 seconds, developed with an aqueous solution of tetramethylammonium hydroxide (2.38 mass %) for 30 seconds, rinsed with pure water and spin dried, thereby obtaining a resist pattern.

[Sensitivity, Resolution (γ)]

Surface exposure was carried out while changing the exposure amount by 0.5 mJ at a time within the range of 10 to 40 mJ/cm$^2$, and the exposed film was baked at 110° C. for 90 seconds. Thereafter, using a 2.38 mass % aqueous tetramethylammonium hydroxide (TMAH) solution, the dissolution rate in each of the exposure amounts was measured, thereby obtaining a solubility curve.

The sensitivity was defined as the exposure amount in which the dissolution rate of the resist was saturated on the solubility curve. Further, the dissolution contrast (γ value) was calculated from the gradient of the straight line portion of the solubility curve. The larger the γ value, the more favorable the dissolution contrast and the greater the advantage in resolution.

[Line Edge Roughness (LER)]

In the measurement of line edge roughness (nm), a 75 nm width line and space (1/1) pattern was observed by means of a critical dimension scanning electron microscope (SEM, model S-8840 manufactured by Hitachi, Ltd.). In a 2 μm region along the longitudinal direction of the line pattern, the distances of actual edges from a reference line on which edges were to be present were measured on 50 points by the above scanning electron microscope. The standard deviation of measurements was determined, and 3σ was computed therefrom. The smaller the value thereof, the more favorable the performance exhibited.

[Pattern Profile]

The optimum exposure amount was defined as the exposure amount that reproduced a line-and-space (L/S=1/1) mask pattern of 75 nm line width. The profile realized in the optimum exposure amount was observed by means of a scanning electron microscope (SEM).

[Outgassing Performance: Ratio of Change in Film Thickness by Exposure]

Exposure to an electron beam was carried out in the exposure amount equal to 2.0 times the exposure amount realizing the above sensitivity. The film thickness after the exposure but before postbake was measured, and the ratio of change from the film thickness before the exposure was calculated by the following formula.

Ratio of change in film thickness (%)=[(film thickness before exposure−film thickness after exposure)/(film thickness before exposure)]×100.

The obtained measurement results are given in Table 4 below.

TABLE 4

(ArF: positive)

| | Acid generator (A1) [0.4 g] | Acid generator (A2) [0.4 g] | Resin (B) (9.6 g) | Basic compound (0.02 g) | Surfactant (0.1 mass %) | Solvent [mass ratio] | Sensitivity (mJ/cm$^2$) | Resolution γ | LER (nm) | Configuration of pattern | Outgassing performance (%) |
|---|---|---|---|---|---|---|---|---|---|---|---|
| Ex. 1A | A1-1 | — | RA-2 | C-1 | W-1 | A1/B1 [6/4] | 27.0 | 7.2 | 4.0 | Rectangle | 5.5 |
| Ex. 2A | A1-2 | — | RA-2 | C-1 | W-1 | A1/B1 [6/4] | 29.0 | 7.0 | 4.1 | Rectangle | 3.5 |
| Ex. 3A | A1-16 | Z | RA-2 | C-1 | W-1 | A1/B1 [6/4] | 28.0 | 7.1 | 4.2 | Rectangle | 3.0 |
| Ex. 4A | A1-19 | — | RA-2 | C-1 | W-1 | A1/B1 [6/4] | 29.0 | 6.4 | 5.5 | Rectangle | 4.0 |
| Ex. 5A | A1-24 | — | RA-2 | C-1 | W-1 | A1/B1 [6/4] | 28.0 | 6.7 | 5.0 | Rectangle | 3.5 |

TABLE 4-continued (ArF: positive)

| | Acid generator (A1) [0.4 g] | Acid generator (A2) [0.4 g] | Resin (B) (9.6 g) | Basic compound (0.02 g) | Surfactant (0.1 mass %) | Solvent [mass ratio] | Sensitivity (mJ/cm$^2$) | Resolution γ | LER (nm) | Configuration of pattern | Outgassing performance (%) |
|---|---|---|---|---|---|---|---|---|---|---|---|
| Ex. 6A | A1-35 | — | RA-3 | C-3 | W-1 | A1/B1 [6/4] | 29.0 | 5.4 | 6.3 | Rectangle | 4.5 |
| Ex. 7A | A1-54 | — | RA-1 | C-1 | W-1 | A2/B2 [6/4] | 29.0 | 5.2 | 6.5 | Rectangle | 5.5 |
| Ex. 8A | A1-69 | — | RA-2 | C-1 | W-2 | A1/B1 [6/4] | 26.0 | 7.3 | 4.2 | Rectangle | 5.5 |
| Ex. 9A | A1-70 | Z | RA-2 | C-1 | W-3 | A3/B1 [6/4] | 27.0 | 6.6 | 4.3 | Rectangle | 3.0 |
| Ex. 10A | A1-79 | — | RA-2 | C-1 | W-3 | A3/B1 [6/4] | 27.0 | 6.5 | 4.8 | Rectangle | 3.0 |
| Ex. 11A | A1-83 | — | RA-4 | C-1 | W-3 | A3/B1 [6/4] | 28.0 | 6.0 | 6.2 | Rectangle | 5.0 |
| Ex. 12A | A1-96 | — | RA-3 | C-2 | W-4 | A4/B1 [6/4] | 27.0 | 6.8 | 4.4 | Rectangle | 5.5 |
| Ex. 13A | A1-1 | — | RA-4 | C-3 | W-4 | A4/B1 [6/4] | 27.0 | 6.8 | 4.2 | Rectangle | 5.5 |
| Ex. 14A | A1-69 | — | RA-3 | C-2 | W-4 | A4/B1 [6/4] | 26.0 | 6.4 | 4.3 | Rectangle | 5.5 |
| Ex. 15A | A1-96 | — | RA-4 | C-3 | W-4 | A4/B1 [6/4] | 27.0 | 6.6 | 4.7 | Rectangle | 5.5 |
| Comp. 1A | Comparative compound 1 | — | RA-2 | C-1 | W-1 | A1/B1 [6/4] | 30.0 | 4.2 | 7.4 | Taper | 6.8 |
| Comp. 2A | Comparative compound 2 | — | RA-2 | C-1 | W-1 | A1/B1 [6/4] | 33.0 | 5.1 | 7.2 | Taper | 6.2 |
| Comp. 3A | Comparative compound 3 | — | RA-2 | C-1 | W-1 | A1/B1 [6/4] | 30.0 | 4.8 | 6.9 | Taper | 6.4 |
| Comp. 4A | Comparative compound 4 | — | RA-2 | C-1 | W-1 | A1/B1 [6/4] | 31.0 | 4.8 | 6.7 | Taper | 6.4 |
| Comp. 5A | Comparative compound 5 | — | RA-2 | C-1 | W-1 | A1/B1 [6/4] | 33.0 | 4.6 | 6.5 | Rectangle | 6.4 |

The employed components are as follows.

[Acid Generator]

The acid generators (A1) according to the present invention are those mentioned hereinbefore by way of example.

The acid generator (A2) used in combination therewith is compound Z shown below.

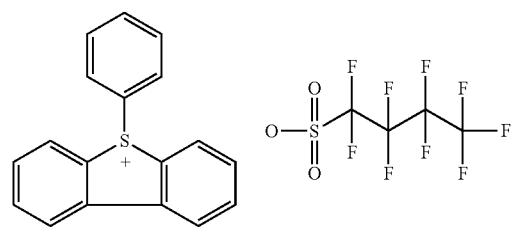

(Z)

Comparative compounds 1 to 5 are shown below. With respect to comparative compound 2, the volume (216 Å$^3$) of the acid resulting from bonding of a proton to the anion moiety thereof is indicated. The volume is a value computed by the above-mentioned method.

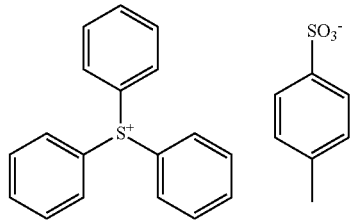

Comparative compound 1

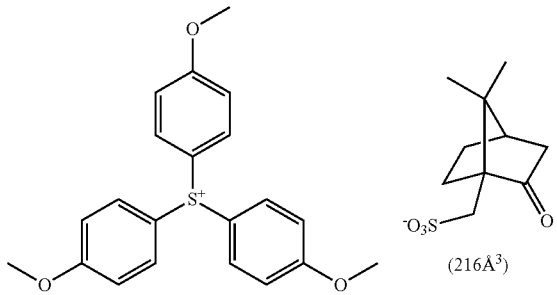

Comparative compound 2

(216Å$^3$)

-continued

Comparative compound 3

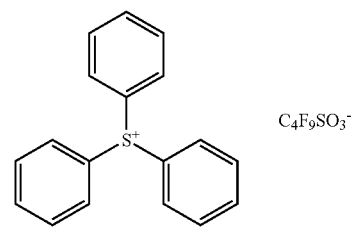

Comparative compound 4

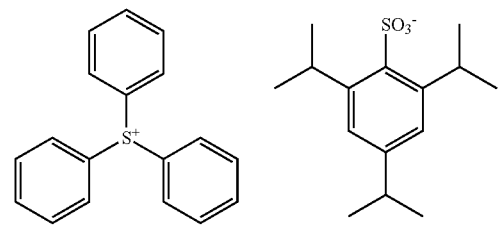

Comparative compound 5

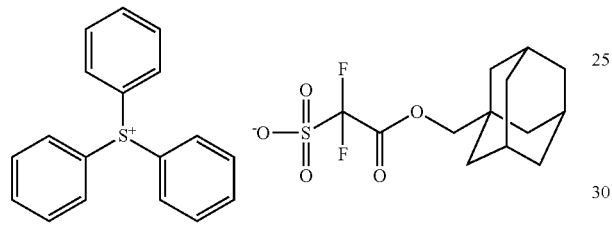

[Resin]

Any of resins (RA-1) to (RA-4) shown below was used as the resin. In the following formulae, the numerics appearing on the right side of individual repeating units indicate a molar ratio of repeating units. Mw means the weight average molecular weight, and Mw/Mn means the molecular weight dispersity.

(RA-1)

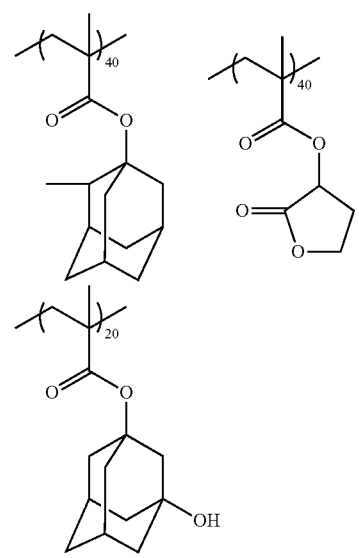

Mw = 10700
Mw/Mn = 1.81

-continued (RA-2)

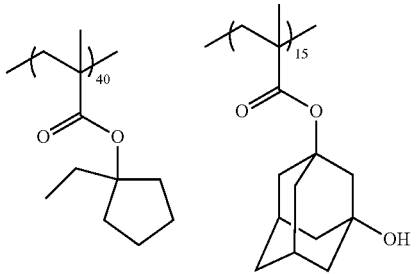

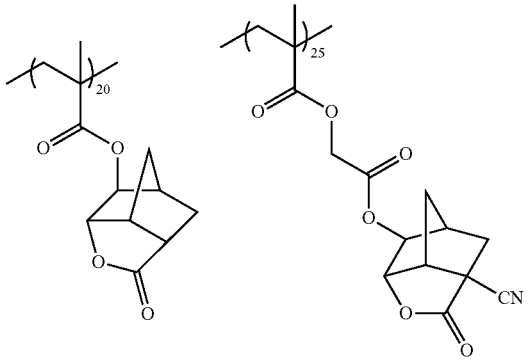

Mw = 8500
Mw/Mn = 1.60

(RA-3)

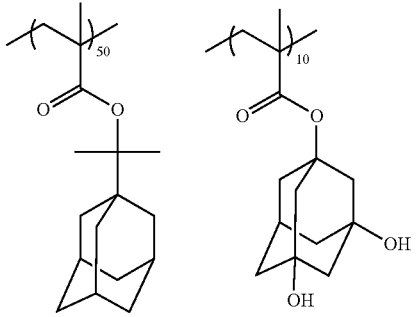

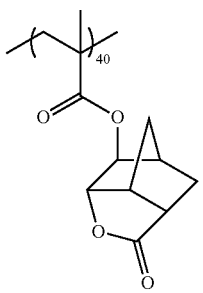

Mw = 8800
Mw/Mn = 1.90

-continued (RA-4)

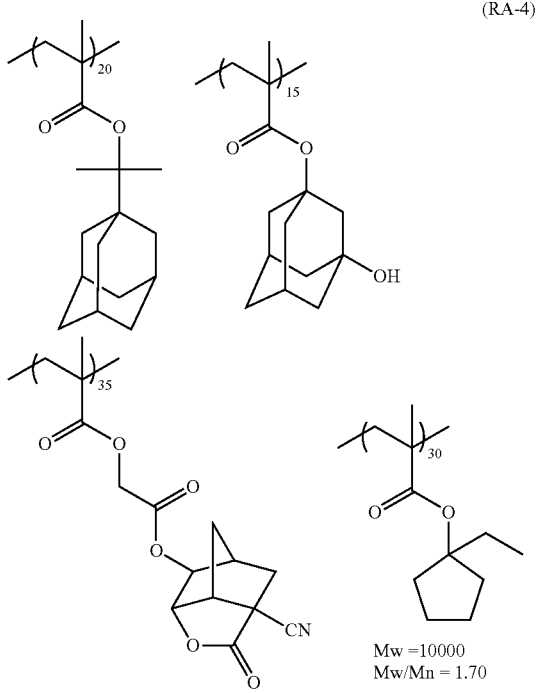

Mw =10000
Mw/Mn = 1.70

<Basic Compound>

The following compounds C-1 to C-3 were used as the basic compound.
C-1: 2,4,5-triphenylimidazole,
C-2: tetrabutylammonium hydroxide, and
C-3: 1,5-diazabicyclo[4.3.0]non-5-ene.

<Surfactant>

The following surfactants W-1 to W-4 were used.
W-1: Megafac F176 (produced by Dainippon Ink & Chemicals, Inc.; fluorinated),
W-2: Megafac R08 (produced by Dainippon Ink & Chemicals, Inc.; fluorinated and siliconized),
W-3: polysiloxane polymer KP-341 (produced by Shin-Etsu Chemical Co., Ltd.; siliconized), and
W-4: Troy Sol S-366 (produced by Troy Chemical Co., Ltd.; fluorinated).

<Solvent>

The following solvents A1 to A4 and B1 and B2 were used. These solvents were used in appropriate combination.
A1: propylene glycol monomethyl ether acetate,
A2: 2-heptanone,
A3: cyclohexanone,
A4: γ-butyrolactone,
B1: propylene glycol monomethyl ether, and
B2: ethyl acetate.

It is apparent from the results of Table 4 that in the employment of ArF exposure, the actinic-ray- or radiation-sensitive resin composition of the present invention excels in all of the sensitivity, resolution, LER, pattern profile and outgassing performance.

EXAMPLE B

A resist solution was prepared according to the same procedure as in Example A except that 0.06 g of polymer shown below was added to the composition of Example 1A. The resist solution was applied in the same manner, thereby obtaining a resist film. The obtained resist film was patternwise exposed through an immersion liquid (pure water) by means of an ArF excimer laser liquid-immersion scanner (manufactured by ASML, XT1700i, NA 1.2), thereby accomplishing the same pattern formation as in Example A. With respect to the obtained pattern, it was ascertained that in all of the sensitivity, resolution, LER, pattern profile and outgassing performance, the same evaluation results were obtained.

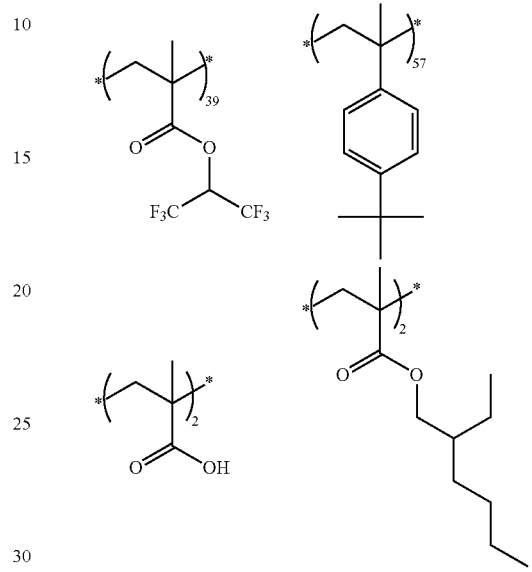

Weight average molecular weight: 4500
Dispersity: 1.4

EXAMPLE C

Examples 1C to 10C and Comparative Examples 1C and 2C

<Preparation of Resist>

Referring to Table 5 below, with respect to each of the resists, the individual components were dissolved in the solvent and passed through a polytetrafluoroethylene filter of 0.1 μm pore size, thereby obtaining a positive resist solution of 8 mass % solid content.

<Evaluation of Resist>

Each of the obtained positive resist solutions was uniformly applied onto a silicon substrate having undergone a hexamethyldisilazane treatment by means of a spin coater, and dried by heating on a hot plate at 120° C. for 90 seconds, thereby obtaining a 0.4 μm-thick resist film.

The obtained resist film was patternwise exposed through a line-and-space mask by means of a KrF excimer laser stepper (NA=0.63). Immediately after the exposure, the resist film was baked on a hot plate at 110° C. for 90 seconds. Thereafter, the resist film was developed with a 2.38 mass % aqueous tetramethylammonium hydroxide solution at 23° C. for 60 seconds, rinsed with pure water for 30 seconds and dried. Thus, an intended line pattern was obtained.

[Sensitivity, Resolution (γ)]

Surface exposure was carried out while changing the exposure amount by 0.5 mJ at a time within the range of 10 to 40 mJ/cm², and the exposed film was baked at 110° C. for 90 seconds. Thereafter, using a 2.38 mass % aqueous tetramethylammonium hydroxide (TMAH) solution, the dissolution rate in each of the exposure amounts was measured, thereby obtaining a solubility curve.

The sensitivity was defined as the exposure amount in which the dissolution rate of the resist was saturated on the solubility curve. Further, the dissolution contrast (γ value) was calculated from the gradient of the straight line portion of the solubility curve. The larger the γ value, the more favorable the dissolution contrast and the greater the advantage in resolution.

[Line Edge Roughness (LER)]

In the measurement of line edge roughness (nm), a 0.2 μm width line and space (1/1) pattern was observed by means of a critical dimension scanning electron microscope (SEM, model S-8840 manufactured by Hitachi, Ltd.). In a 5 μm region along the longitudinal direction of the line pattern, the distances of actual edges from a reference line on which edges were to be present were measured on 50 points by the above scanning electron microscope. The standard deviation of measurements was determined, and 3σ was computed therefrom. The smaller the value thereof, the more favorable the performance exhibited.

[Pattern Profile]

The optimum exposure amount was defined as the exposure amount that reproduced a line-and-space (L/S=1/1) mask pattern of 0.20 μm line width. The profile realized in the optimum exposure amount was observed by means of a scanning electron microscope (SEM).

[Outgassing Performance: Ratio of Change in Film Thickness by Exposure]

Exposure to an electron beam was carried out in the exposure amount equal to 2.0 times the exposure amount realizing the above sensitivity. The film thickness after the exposure but before postbake was measured, and the ratio of change from the film thickness before the exposure was calculated by the following formula.

Ratio of change in film thickness (%)=[(film thickness before exposure−film thickness after exposure)/(film thickness before exposure)]×100.

The obtained measurement results are given in Table 5 below.

The photoacid generators (A1) and (A2), basic compound, surfactant and solvent were appropriately selected from among those set forth hereinbefore and used.

The resin was appropriately selected from among the resins (R-1) to (R-30) set forth hereinbefore by way of example and used. With respect to each of the resins (R-18), (R-19), (R-22), (R-27) and (R-29) appearing in Table 2 and the following tables, the molar ratio of individual repeating units and the weight average molecular weight are given in Table 6 below.

TABLE 6

| Resin | Molar ratio of repeating units (corresponding to individual repeating units in order from the left in each structural formula) | Weight average molecular weight (Mw) |
|---|---|---|
| R-18 | 75/25 | 10000 |
| R-19 | 60/20/20 | 12000 |
| R-22 | 70/30 | 12000 |
| R-27 | 50/45/5 | 15000 |
| R-29 | 50/45/5 | 15000 |

It is apparent from the results of Table 5 that in the application of KrF exposure, the composition of the present invention excels in the sensitivity, resolution, LER, pattern profile and outgassing performance. That is, it is apparent that the composition of the present invention can also exhibit excellent performance as a positive resist composition exposed to an KrF excimer laser.

EXAMPLE D

Examples 1D to 26D and Comparative Examples 1D to 5D

<Preparation of Resist>

Referring to Table 7 below, with respect to each of the resists, the individual components were dissolved in the sol-

TABLE 5

(KrF: positive)

| | Acid generator (A1) [0.3 g] | Acid generator (A2) [0.1 g] | Resin (B) (10 g) | Basic compound (0.02 g) | Surfactant (0.1 mass %) | Solvent [mass ratio] | Sensitivity (mJ/cm²) | Resolution γ | LER (nm) | Configuration of pattern | Outgassing performance (%) |
|---|---|---|---|---|---|---|---|---|---|---|---|
| Ex. 1C | A1-1 | — | R-18 | C-1 | W-1 | A1/B1 [6/4] | 20.5 | 7.5 | 4.5 | Rectangle | 5.5 |
| Ex. 2C | A1-2 | — | R-18 | C-1 | W-1 | A1/B1 [6/4] | 21.5 | 6.4 | 4.3 | Rectangle | 3.5 |
| Ex. 3C | A1-12 | — | R-19 | C-1 | W-1 | A3/B1 [6/4] | 21.0 | 6.1 | 4.4 | Rectangle | 4.0 |
| Ex. 4C | A1-13 | — | R-18 | C-2 | W-1 | A4/B1 [6/4] | 22.0 | 5.8 | 4.9 | Rectangle | 3.0 |
| Ex. 5C | A1-16 | — | R-18 | C-1 | W-1 | A1/B1 [6/4] | 20.5 | 7.1 | 4.5 | Rectangle | 6.0 |
| Ex. 6C | A1-19 | — | R-19 | C-1 | W-1 | A1/B1 [6/4] | 22.5 | 6.4 | 4.5 | Rectangle | 4.0 |
| Ex. 7C | A1-24 | — | R-18 | C-3 | W-1 | A1/B1 [6/4] | 22.0 | 6.1 | 4.5 | Rectangle | 3.5 |
| Ex. 8C | A1-31 | Z | R-22 | C-1 | W-2 | A1/B1 [6/4] | 21.0 | 7.2 | 4.8 | Rectangle | 5.5 |
| Ex. 9C | A1-69 | — | R-27 | C-1 | W-3 | A1/B1 [6/4] | 21.0 | 7.0 | 4.9 | Rectangle | 5.5 |
| Ex. 10C | A1-96 | — | R-29 | C-2 | W-1 | A1/B1 [6/4] | 21.0 | 6.8 | 4.8 | Rectangle | 6.0 |
| Comp. 1C | Comparative compound 1 | — | R-18 | C-1 | W-1 | A1/B1 [6/4] | 23.0 | 4.5 | 7.5 | Taper | 7.0 |
| Comp. 2C | Comparative compound 4 | — | R-18 | C-1 | W-1 | A1/B1 [6/4] | 24.0 | 5.5 | 5.5 | Taper | 7.5 | vent and passed through a polytetrafluoroethylene filter of 0.1 μm pore size, thereby obtaining a positive resist solution of 4 mass % solid content.

<Evaluation of Resist>

Each of the prepared positive resist solutions was uniformly applied onto a silicon substrate having undergone a hexamethyldisilazane treatment by means of a spin coater, and dried by heating on a hot plate at 120° C. for 60 seconds, thereby obtaining a 0.12 μm-thick resist film.

Each of the resist films was exposed to an electron beam by means of an electron beam projection lithography system (acceleration voltage 100 KeV) manufactured by Nikon Corporation. Immediately after the exposure, the film was baked on a hot plate at 110° C. for 90 seconds. Thereafter, the baked film was developed with a 2.38 mass % aqueous tetramethylammonium hydroxide solution at 23° C. for 60 seconds. After the development, the film was rinsed with pure water for 30 seconds and dried. Thus, a line-and-space pattern was formed.

[Sensitivity]

Each of the obtained patterns was observed by means of a scanning electron microscope (model S-9220 manufactured by Hitachi, Ltd.). The sensitivity (Eo) was defined as the electron beam exposure amount in which 0.10 μm (line: space=1:1) was resolved.

[Resolution]

The resolution (dense) was defined as the limiting resolving power (minimum line width at which the line and space were separated and resolved from each other) of 1:1 line space in the exposure amount exhibiting the above sensitivity.

[Line Edge Roughness (LER)]

LER was determined in the same manner as in Example A.

[Pattern Profile]

The profile of 1:1 line space in the exposure amount exhibiting the above sensitivity was observed by means of a scanning electron microscope (SEM).

[Outgassing Performance: Ratio of Change in Film Thickness by Exposure]

The outgassing performance was evaluated in the same manner as in Example A.

These evaluation results are given in Table 7 below.

TABLE 7

(EB: positive)

| | Acid generator (A1) [0.3 g] | Acid generator (A2) [0.1 g] | Resin (B) (10 g) | Basic compound (0.02 g) | Surfactant (0.1 mass %) | Solvent [mass ratio] | Sensitivity (μC/cm$^2$) | Resolution (nm) | LER (nm) | Configuration of pattern | Outgassing performance (%) |
|---|---|---|---|---|---|---|---|---|---|---|---|
| Ex. 1D | A1-1 | — | R-18 | C-1 | W-1 | A1/B1 [6/4] | 18.5 | 45 | 4.0 | Rectangle | 4.4 |
| Ex. 2D | A1-2 | — | R-18 | C-1 | W-1 | A2/B2 [6/4] | 20.0 | 50 | 4.5 | Rectangle | 2.4 |
| Ex. 3D | A1-12 | — | R-18 | C-1 | W-1 | A3/B1 [6/4] | 20.0 | 50 | 4.4 | Rectangle | 2.2 |
| Ex. 4D | A1-13 | — | R-19 | C-1 | W-1 | A4/B1 [6/4] | 20.5 | 60 | 5.2 | Rectangle | 3.0 |
| Ex. 5D | A1-15 | — | R-18 | C-1 | W-1 | A1/B1 [6/4] | 20.0 | 65 | 5.5 | Rectangle | 2.0 |
| Ex. 6D | A1-16 | — | R-18 | C-1 | W-1 | A1/B1 [6/4] | 19.5 | 55 | 4.9 | Rectangle | 2.0 |
| Ex. 7D | A1-19 | — | R-18 | C-1 | — | A1/B1 [6/4] | 18.5 | 65 | 6.5 | Rectangle | 3.5 |
| Ex. 8D | A1-24 | — | R-18 | C-1 | W-1 | A1/B1 [6/4] | 19.0 | 65 | 6.3 | Rectangle | 2.8 |
| Ex. 9D | A1-31 | Z | R-19 | C-1 | W-2 | A1/B1 [6/4] | 18.5 | 65 | 6.8 | Rectangle | 5.2 |
| Ex. 10D | A1-35 | — | R-29 | C-1 | W-3 | A1/B1 [6/4] | 20.5 | 70 | 6.9 | Rectangle | 5.9 |
| Ex. 11D | A1-38 | — | R-29 | C-2 | W-1 | A1/B1 [6/4] | 21.0 | 60 | 5.6 | Rectangle | 1.9 |
| Ex. 12D | A1-50 | — | R-22 | C-1 | W-4 | A1/B1 [6/4] | 19.5 | 65 | 6.8 | Rectangle | 2.4 |
| Ex. 13D | A1-54 | — | R-22 | C-1 | W-4 | A1/B1 [6/4] | 18.5 | 70 | 5.8 | Rectangle | 5.2 |
| Ex. 14D | A1-64 | — | R-29 | C-1 | W-4 | A1/B1 [6/4] | 19.0 | 75 | 5.5 | Rectangle | 6.5 |
| Ex. 15D | A1-69 | — | R-29 | C-1 | W-4 | A1/B1 [6/4] | 17.0 | 45 | 4.0 | Rectangle | 3.5 |
| Ex. 16D | A1-70 | — | R-29 | C-3 | W-4 | A1/B1 [6/4] | 18.5 | 55 | 5.2 | Rectangle | 2.4 |
| Ex. 17D | A1-79 | — | R-29 | C-1 | W-4 | A1/B1 [6/4] | 19.0 | 55 | 5.5 | Rectangle | 2.1 |
| Ex. 18D | A1-83 | Z | R-29 | C-1 | W-4 | A1/B1 [6/4] | 20.5 | 65 | 6.4 | Rectangle | 2.1 |
| Ex. 19D | A1-91 | — | R-27 | C-2 | W-1 | A1/B1 [6/4] | 17.5 | 50 | 4.4 | Rectangle | 2.2 |
| Ex. 20D | A1-96 | — | R-29 | C-1 | W-1 | A1/B1 [6/4] | 18.0 | 50 | 4.2 | Rectangle | 1.9 |
| Ex. 21D | A1-98 | — | R-29 | C-1 | W-1 | A1/B1 [6/4] | 17.0 | 55 | 4.8 | Rectangle | 2.5 |
| Ex. 22D | A1-1 | — | R-19 | C-1 | W-1 | A1/B1 [6/4] | 17.5 | 45 | 4.5 | Rectangle | 1.8 |
| Ex. 23D | A1-1 | — | R-18 | C-2 | W-1 | A1/B1 [6/4] | 17.5 | 45 | 4.4 | Rectangle | 1.8 |

TABLE 7-continued (EB: positive)

| | Acid generator (A1) [0.3 g] | Acid generator (A2) [0.1 g] | Resin (B) (10 g) | Basic compound (0.02 g) | Surfactant (0.1 mass %) | Solvent [mass ratio] | Sensitivity ($\mu C/cm^2$) | Resolution (nm) | LER (nm) | Configuration of pattern | Outgassing performance (%) |
|---|---|---|---|---|---|---|---|---|---|---|---|
| Ex. 24D | A1-69 | — | R-22 | C-1 | W-1 | A1/B1 [6/4] | 17.5 | 45 | 4.4 | Rectangle | 1.8 |
| Ex. 25D | A1-69 | — | R-27 | C-1 | W-1 | A1/B1 [6/4] | 17.5 | 50 | 4.5 | Rectangle | 1.8 |
| Ex. 26D | A1-96 | — | R-22 | C-1 | W-1 | A1/B1 [6/4] | 17.5 | 50 | 4.4 | Rectangle | 1.8 |
| Comp. 1D | Comparative compound 1 | — | R-18 | C-1 | W-1 | A1/B1 [6/4] | 21.5 | 80 | 8.0 | Taper | 4.7 |
| Comp. 2D | Comparative compound 2 | — | R-29 | C-1 | W-1 | A1/B1 [6/4] | 21.5 | 75 | 7.5 | Taper | 4.2 |
| Comp. 3D | Comparative compound 3 | — | R-29 | C-1 | W-1 | A1/B1 [6/4] | 21.0 | 75 | 7.8 | Taper | 3.4 |
| Comp. 4D | Comparative compound 4 | — | R-18 | C-1 | W-1 | A1/B1 [6/4] | 23.0 | 70 | 7.4 | Taper | 3.1 |
| Comp. 5D | Comparative compound 5 | — | R-29 | C-1 | W-1 | A1/B1 [6/4] | 22.0 | 70 | 7.2 | Rectangle | 3.1 |

It is apparent from the results of Table 7 that in the exposure to an electron beam, the composition of the present invention excels in all of the sensitivity, resolution, LER, pattern profile and outgassing performance. That is, it is apparent that the actinic-ray- or radiation-sensitive resin composition of the present invention can also exhibit excellent performance as a positive resist composition exposed to an electron beam.

EXAMPLE E

Examples 1E to 9E and Comparative Examples 1E and 2E (Preparation of Resist)
Referring to Table 8 below, with respect to each of the resists, the individual components were dissolved in the solvent and passed through a polytetrafluoroethylene filter of 0.1 μm pore size, thereby obtaining a negative resist solution of 4 mass % solid content.

<Evaluation of Resist>
Each of the prepared negative resist solutions was uniformly applied onto a silicon substrate having undergone a hexamethyldisilazane treatment by means of a spin coater, and dried by heating on a hot plate at 120° C. for 60 seconds, thereby obtaining a 0.12 μm-thick resist film.
Each of the resist films was exposed to an electron beam by means of an electron beam projection lithography system (acceleration voltage 100 KeV) manufactured by Nikon Corporation. Immediately after the exposure, the film was baked on a hot plate at 110° C. for 90 seconds. Thereafter, the baked film was developed with a 2.38 mass % aqueous tetramethylammonium hydroxide solution at 23° C. for 60 seconds. After the development, the film was rinsed with pure water for 30 seconds and dried. Thus, a line-and-space pattern was formed.
Evaluation was conducted in the same manner as in Example D. The evaluation results are given in Table 8.

TABLE 8

(EB: negative)

| | Acid generator (A1) (0.3 g) | Resin (C) (10 g) | Cross-linking agent (3.0 g) | Basic compound (0.02 g) | Surfactant (0.1 mass %) | Solvent [mass ratio] | Sensitivity ($\mu C/cm^2$) | Resolution (nm) | LER (nm) | Configuration of pattern | Outgassing performance (%) |
|---|---|---|---|---|---|---|---|---|---|---|---|
| Ex. 1E | A1-1 | P-3 | CL-1 | C-1 | W-1 | A1/B1 [6/4] | 19.0 | 55 | 9.5 | Rectangle | 6.5 |
| Ex. 2E | A1-2 | P-3 | CL-1 | C-1 | W-1 | A1/B1 [6/4] | 21.0 | 65 | 10.8 | Rectangle | 4.9 |
| Ex. 3E | A1-16 | P-3 | CL-1 | C-1 | W-1 | A1/B1 [6/4] | 22.0 | 65 | 10.5 | Rectangle | 4.0 |
| Ex. 4E | A1-19 | P-3 | CL-1 | C-1 | W-1 | A1/B1 [6/4] | 18.5 | 60 | 9.9 | Rectangle | 5.8 |
| Ex. 5E | A1-35 | P-3 | CL-1 | C-1 | W-1 | A1/B1 [6/4] | 23.5 | 70 | 10.2 | Rectangle | 3.9 |
| Ex. 6E | A1-54 | P-3 | CL-1 | C-1 | W-1 | A1/B1 [6/4] | 22.5 | 50 | 10.5 | Rectangle | 3.5 |
| Ex. 7E | A1-69 | P-1 | CL-1 | C-1 | W-1 | A1/B1 [6/4] | 20.0 | 55 | 9.3 | Rectangle | 6.6 |
| Ex. 8E | A1-70 | P-2 | CL-2 | C-1 | W-2 | A1/B1 [6/4] | 20.5 | 60 | 10.1 | Rectangle | 6.9 |
| Ex. 9E | A1-96 | P-1 | CL-3 | C-1 | W-3 | A1/B1 [6/4] | 20.0 | 60 | 10.5 | Rectangle | 6.1 |

TABLE 8-continued (EB: negative)

| | Acid generator (A1) (0.3 g) | Resin (C) (10 g) | Cross-linking agent (3.0 g) | Basic compound (0.02 g) | Surfactant (0.1 mass %) | Solvent [mass ratio] | Sensitivity ($\mu C/cm^2$) | Resolution (nm) | LER (nm) | Configuration of pattern | Outgassing performance (%) |
|---|---|---|---|---|---|---|---|---|---|---|---|
| Comp. 1E | Comparative compound 1 | P-3 | CL-1 | C-1 | W-1 | A1/B1 [6/4] | 25.6 | 75 | 13.4 | Taper | 9.5 |
| Comp. 2E | Comparative compound 2 | P-3 | CL-1 | C-1 | W-1 | A1/B1 [6/4] | 25.5 | 70 | 12.4 | Taper | 8.2 |

The structures, molecular weights and molecular weight distributions of employed alkali-soluble resins (C) are shown below. Also, the structures of employed acid crosslinking agents are shown below.

| | | Mw | Mw/Mn |
|---|---|---|---|
| P-1 | | 16000 | 2.30 |
| P-2 | | 12000 | 1.2 |
| P-3 | | 6000 | 12 |

VP-5000 produced by Nippon Soda Co., Ltd.

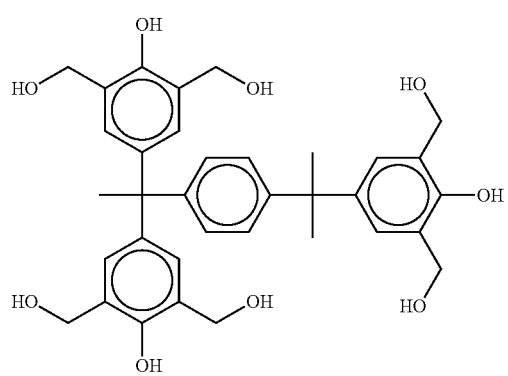

CL-1

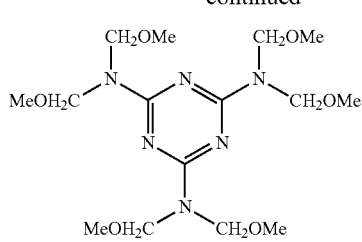

CL-2

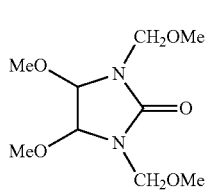

CL-3

It is apparent from the results of Table 8 that in the exposure to an electron beam, the composition of the present invention excels in all of the sensitivity, resolution, LER, pattern profile and outgassing performance. That is, it is apparent that the actinic-ray- or radiation-sensitive resin composition of the present invention can also exhibit excellent performance as a negative resist composition exposed to an electron beam.

EXAMPLE F

Examples 1F to 8F and Comparative Examples 1F and 2F

<Preparation of Resist>

Referring to Table 9 below, with respect to each of the resists, the individual components were dissolved in the solvent and passed through a polytetrafluoroethylene filter of 0.1 μm pore size, thereby obtaining a positive resist solution of 4 mass % solid content.

<Evaluation of Resist>

Each of the prepared positive resist solutions was uniformly applied onto a silicon substrate having undergone a hexamethyldisilazane treatment by means of a spin coater, and dried by heating on a hot plate at 120° C. for 60 seconds, thereby obtaining a 0.12 μm-thick resist film.

Each of the formed resist films was exposed to EUV by means of an EUV exposure apparatus (wavelength 13 nm). Immediately after the exposure, the film was baked on a hot plate at 110° C. for 90 seconds. The baked film was developed with a 2.38 mass % aqueous tetramethylammonium hydroxide solution at 23° C. for 60 seconds, rinsed with pure water for 30 seconds and dried. Thus, line and space patterns (line: space=1:1) were formed. The obtained patterns were evaluated by the following methods.

[Sensitivity]

Each of the obtained patterns was observed by means of a scanning electron microscope (model S-9220, manufactured by Hitachi, Ltd.). The sensitivity (Eo) was defined as the electron beam exposure amount in which 0.10 μm (line:space=1:1) could be resolved.

[Line Edge Roughness (LER)]

A 50 nm line pattern (L/S=1/1) was formed in the exposure amount realizing the above sensitivity. At arbitrary 30 points in a 50 μm region in the longitudinal direction thereof, the distance of actual edge from a reference line on which edges were to be present was measured by means of a scanning electron microscope (model S-9220, manufactured by Hitachi, Ltd.). The standard deviation of measured distances was determined, and 3 σ was computed.

[Pattern Profile]

The pattern profile resulting from exposure to EUV was evaluated in the same manner as in Example D.

[Outgassing Performance: Ratio of Change in Film Thickness by Exposure]

The ratio of change in film thickness by exposure to EUV was determined in the same manner as in Example D.

The obtained evaluation results are given in Table 9 below.

of the sensitivity, LER, pattern profile and outgassing performance. That is, it is apparent that the actinic-ray- or radiation-sensitive resin composition of the present invention can also exhibit excellent performance as a positive resist composition exposed to EUV.

EXAMPLE G

Examples 1G to 3G and Comparative Examples 1G and 2G

<Preparation of Resist>

Referring to Table 10 below, with respect to each of the resists, the individual components were dissolved in the solvent and passed through a polytetrafluoroethylene filter of 0.1 μm pore size, thereby obtaining a negative resist solution of 4 mass % solid content. The negative resist solution was evaluated in the following manner.

<Evaluation of Resist>

Each of the prepared negative resist solutions was uniformly applied onto a silicon substrate having undergone a hexamethyldisilazane treatment by means of a spin coater, and dried by heating on a hot plate at 120° C. for 60 seconds, thereby obtaining a 0.12 μm-thick resist film.

TABLE 9

(EUV: positive)

| | Acid generator (A1) (0.3 g) | Resin (B) (10 g) | Basic compound (0.02 g) | Surfactant (0.1 mass %) | Solvent [mass ratio] | Sensitivity (mJ/cm$^2$) | LER (nm) | Configuration of pattern | Outgassing performance (%) |
|---|---|---|---|---|---|---|---|---|---|
| Ex. 1F | A1-1 | R-23 | C-1 | W-1 | A1/B1 [6/4] | 17.5 | 4.1 | Rectangle | 5.4 |
| Ex. 2F | A1-2 | R-23 | C-1 | W-1 | A1/B1 [6/4] | 18.0 | 4.8 | Rectangle | 4.4 |
| Ex. 3F | A1-35 | R-23 | C-1 | W-1 | A1/B1 [6/4] | 18.0 | 5.4 | Rectangle | 3.6 |
| Ex. 4F | A1-69 | R-23 | C-1 | W-2 | A1/B1 [6/4] | 17.5 | 3.9 | Rectangle | 4.9 |
| Ex. 5F | A1-70 | R-23 | C-1 | W-1 | A1/B1 [6/4] | 18.5 | 4.2 | Rectangle | 3.4 |
| Ex. 6F | A1-79 | R-23 | C-1 | W-1 | A1/B1 [6/4] | 19.5 | 4.9 | Rectangle | 3.8 |
| Ex. 7F | A1-91 | R-22 | C-2 | W-1 | A1/B1 [6/4] | 18.5 | 4.8 | Rectangle | 5.8 |
| Ex. 8F | A1-13 | R-22 | C-2 | W-1 | A1/B1 [6/4] | 17.5 | 4.2 | Rectangle | 4.8 |
| Comp. 1F | Comparative compound 1 | R-23 | C-1 | W-1 | A1/B1 [6/4] | 20.5 | 8.5 | Taper | 8.4 |
| Comp. 2F | Comparative compound 2 | R-23 | C-1 | W-1 | A1/B1 [6/4] | 22.2 | 8.8 | Taper | 8.0 |

It is apparent from the results of Table 9 that in the exposure to EUV, the composition of the present invention excels in all The obtained resist films were evaluated in the same manner as in Example F. The results are given in Table 10 below.

TABLE 10

(EUV: negative)

| | Acid generator (A1) (0.3 g) | Resin (B) (10 g) | Cross-linking agent (C) (3.0 g) | Basic compound (0.02 g) | Surfactant (0.1 mass %) | Solvent [mass ratio] | Sensitivity (mJ/cm$^2$) | LER (nm) | Configuration of pattern | Outgassing performance (%) |
|---|---|---|---|---|---|---|---|---|---|---|
| Ex. 1G | A1-1 | P-3 | CL-1 | C-1 | W-1 | A1/B1 [6/4] | 26.8 | 7.8 | Rectangle | 7.0 |
| Ex. 2G | A1-69 | P-3 | CL-1 | C-1 | W-1 | A1/B1 [6/4] | 27.2 | 7.9 | Rectangle | 6.8 |
| Comp. 1G | Comparative compound 1 | P-3 | CL-1 | C-1 | W-1 | A1/B1 [6/4] | 30.0 | 13.5 | Taper | 7.9 |

It is apparent from the results of Table 10 that in the exposure to EUV, the composition of the present invention excels in all of the sensitivity, LER, pattern profile and outgassing performance. That is, it is apparent that the actinic-ray- or radiation-sensitive resin composition of the present invention can also exhibit excellent performance as a negative resist composition exposed to EUV.

What is claimed is:

1. An actinic-ray- or radiation-sensitive resin composition comprising an arylsulfonium salt that when exposed to actinic rays or radiation, generates an acid, the arylsulfonium salt containing at least one aryl ring on which there are a total of one or more electron donating groups, the acid generated upon exposure to actinic rays or radiation having a volume of 240 Å3 or greater, wherein the arylsulfonium salt contains any of cation moieties of general formula (I):

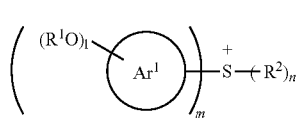

(I)

in which

Ar1 represents an aromatic ring, in which a substituent other than —(OR1) groups may further be introduced, R1 represents a linear or branched alkyl group or a cycloalkyl group, R2 represents an optionally substituted aryl group, an optionally substituted alkyl group or an optionally substituted cycloalkyl group, l is an integer of 1 or greater, and m is an integer of 1 to 3, and n an integer of 0 to 2, provided that m+n=3 is satisfied, provided that when m is 1 and n is 2, two $R^2$s may be bonded to each other to thereby form a tetrahydrothiophene ring or a tetrahydrothiopyran ring in cooperation with the sulfur atom appearing in the formula, and provided that when m is 2 and n is 1, or when m is 3 and n is 0, two $Ar^1$s, or $Ar^1$ and $R^2$ may be bonded to each other to thereby form a ring structure in cooperation with the sulfur atom appearing in the formula, in which two $Ar^1$s, or $Ar^1$ and $R^2$ are simultaneously phenyl groups and the ring structure formed is a dibenzothiophene ring or a dibenzothiopyran ring;

wherein the arylsulfonium salt contains any of anion moieties of general formula (II):

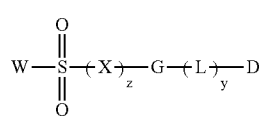

(II)

in which

X represents an optionally substituted alkylene group or an optionally substituted fluoroalkylene group, z being an integer of 0 or greater, G represents an alkylene group or arylene group optionally containing an ether oxygen, a group constituted of a combination thereof, or a single bond, L represents a bivalent connecting group, y being an integer of 0 or greater, D represents an optionally substituted organic group, and W represents any of groups of formulae:

(III)

(IV)

wherein Rf represents a fluoroalkyl group having at least one fluorine atom introduced therein as a substituent; and wherein in general formula (II), D represents any of groups of formula (V):

(V)

in which

Ar2 represents an aromatic ring, in which a substituent other than -(A-B) groups may further be introduced, p is an integer of 1 or greater, A represents a single bond, B represents a cycloaliphatic group, provided that when p is 2 or greater, a plurality of -(A-B) groups may be identical to or different from each other, and

* represents a site of connection to L of general formula (II).

2. The actinic-ray- or radiation-sensitive resin composition according to claim 1, wherein in general formula (I), m is 2 or 3.

3. The actinic-ray- or radiation-sensitive resin composition according to claim 2, wherein m is 3 and n is 0 in general formula (I).

4. The actinic-ray- or radiation-sensitive resin composition according to claim 1, further comprising a resin that when acted on by an acid, is decomposed to thereby increase its solubility in an alkali developer.

5. The actinic-ray- or radiation-sensitive resin composition according to claim 4, wherein the resin that when acted on by an acid, is decomposed to thereby increase its solubility in an alkali developer contains a repeating unit represented by the following general formula (A):

(A)

in which each of $R_{01}$, $R_{02}$ and $R_{03}$ independently represents a hydrogen atom, an alkyl group, a cycloalkyl group, a halogen atom, a cyano group or an alkoxycarbonyl group;

Ar$_1$ represents an aromatic ring group, and alternatively, R$_{03}$ and Ar$_1$ may be simultaneously alkylene groups and bonded to each other so as to form a 5-membered or 6-membered ring in cooperation with —C—C—;

each of n Y's independently represents a hydrogen atom or a group that is eliminated by the action of an acid, provided that at least one of the Y's is a group that is eliminated by the action of an acid; and n is an integer of 1 to 4.

6. The actinic-ray- or radiation-sensitive resin composition according to claim 5, wherein in general formula (A), at least one group of Ys that is eliminated by the action of an acid has a structure represented by the following general formula (B):

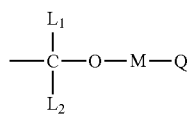

(B)

in which each of L$_1$ and L$_2$ independently represents a hydrogen atom, an alkyl group, a cycloalkyl group, an aryl group or an aralkyl group;

M represents a single bond or a bivalent connecting group;

Q represents an alkyl group, a cycloalkyl group, an alicyclic group, an aromatic ring group, an amino group, an ammonium group, a mercapto group, a cyano group or an aldehyde group, and the alicyclic group and the aromatic ring group may contain a heteroatom; and at least two of Q, M and L$_1$ may be bonded to each other to thereby form a 5-membered or 6-membered ring.

7. The actinic-ray- or radiation-sensitive resin composition according to claim 1, further comprising a resin soluble in an alkali developer and an acid crosslinking agent capable of cros slinking with the resin soluble in an alkali developer under the action of an acid.

8. A resist film formed from the actinic-ray- or radiation-sensitive resin composition according to claim 1.

9. A method of forming a pattern, comprising forming the actinic-ray- or radiation-sensitive resin composition according to claim 1 into a film, exposing the film and developing the exposed film.

10. The method of forming a pattern according to claim 9, wherein the exposure is performed using X-rays, an electron beam or EUV.

11. The actinic-ray- or radiation-sensitive resin composition according to claim 1, wherein p is 3 in general formula (V).

12. The actinic-ray- or radiation-sensitive resin composition according to claim 11, wherein B is a cycloaliphatic group in general formula (V).

13. The actinic-ray- or radiation-sensitive resin composition according to claim 12, wherein B is a cyclohexyl group in general formula (V).

14. The actinic-ray- or radiation-sensitive resin composition according to claim 1, wherein the anion moiety of general formula (II) has the following structure:

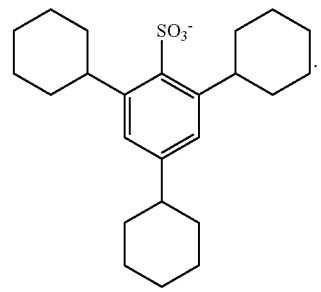

15. The actinic-ray- or radiation-sensitive resin composition according to claim 1, wherein in general formula (V), the cycloaliphatic group represented by B is limited to a cyclohexyl group.

16. The actinic-ray-or radiation-sensitive resin composition according to claim 1, wherein in general formula (I), Ar$^1$ is a phenyl group substituted at its m-position by at least one —(OR$^1$) group.

17. The actinic-ray- or radiation-sensitive resin composition according to claim 1, wherein in general formula (I), the two members selected from among m Ar$^1$s and n R$^2$s are not bonded to each other.

18. The actinic-ray- or radiation-sensitive resin composition according to claim 1, wherein in general formula (I), m is an integer of 3.

19. A compound of general formula (VI) that when exposed to actinic rays or radiation, generates an acid having a volume of 240 Å3 or greater,

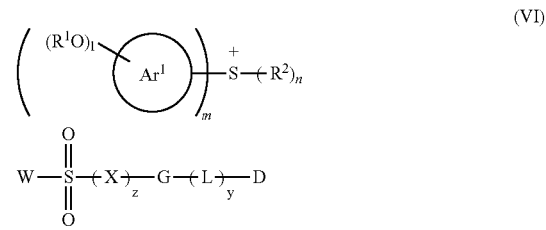

(VI)

in which

Ar1 represents an aromatic ring, in which a substituent other than —(OR1) groups may further be introduced, R1 represents a linear or branched alkyl group or a cycloalkyl group, R2 represents an optionally substituted aryl group, an optionally substituted alkyl group or an optionally substituted cycloalkyl group, l is an integer of 1 or greater, m is an integer of 1 to 3, and n an integer of 0 to 2, provided that m+n=3 is satisfied, provided that when m is 1 and n is 2, two R$^2$s may be bonded to each other to thereby form a tetrahydrothiophene ring or a tetrahydrothiopyran ring in cooperation with the sulfur atom appearing in the formula, and provided that when m is 2 and n is 1, or when m is 3 and n is 0, two Ar$^1$s, or Ar$^1$ and R$^2$ may be bonded to each other to thereby form a ring structure in cooperation with the sulfur atom appearing in the formula, in which two Ar$^1$s, or Ar$^1$ and R$^2$ are simultaneously phenyl groups and the ring structure formed is a dibenzothiophene ring or a dibenzothiopyran ring, X represents an optionally substituted alkylene group or an optionally substituted fluoroalkylene group, z being an integer of 0 or greater, G represents an alkylene group or arylene group optionally containing an ether oxygen, a group constituted of a combination thereof, or a single bond, L represents a bivalent connecting group, y being an integer of 0 or greater, D represents an optionally substituted organic group, and W represents any of groups of formulae:

$$\overset{-}{O}— \quad (III)$$

$$Rf—\overset{\overset{O}{\|}}{\underset{\underset{O}{\|}}{S}}—\overset{-}{N}— \quad (IV)$$

wherein Rf represents a fluoroalkyl group having at least one fluorine atom introduced therein as a substituent and wherein in general formula (VI), D represents any of groups of formula (V):

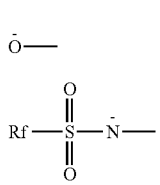

in which

Ar2 represents an aromatic ring, in which a substituent other than -(A-B) groups may further be introduced, p is an integer of 1 or greater, A represents a single bond, B represents a cycloaliphatic group, provided that when p is 2 or greater, a plurality of -(A-B) groups may be identical to or different from each other, and

* represents a site of connection to L of general formula (II).

20. The compound according to claim 19, wherein in general formula (VI), m is 2 or 3.

21. An actinic-ray- or radiation-sensitive resin composition comprising an arylsulfonium salt that when exposed to actinic rays or radiation, generates an acid, the arylsulfonium salt containing at least one aryl ring on which there are a total of one or more electron donating groups, the acid generated upon exposure to actinic rays or radiation having a volume of 240 Å3 or greater, wherein the arylsulfonium salt contains any of cation moieties of general formula (I):

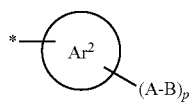

in which

Ar1 represents a phenyl group substituted at is m-position by at least one —(OR$^1$) group, R1 represents a linear or branched alkyl group or a cycloalkyl group, R2 represents an optionally substituted aryl group, an optionally substituted alkyl group or an optionally substituted cycloalkyl group, l is an integer of 1 or greater, and m is an integer of 1 to 3, and n an integer of 0 to 2, provided that m+n=3 is satisfied, provided that when m is 1 and n is 2, two R$^2$s may be bonded to each other to thereby form a tetrahydrothiophene ring or a tetrahydrothiopyran ring in cooperation with the sulfur atom appearing in the formula, and provided that when m is 2 and n is 1, or when m is 3 and n is 0, two Ar$^1$s, or Ar$^1$ and R$^2$ may be bonded to each other to thereby form a ring structure in cooperation with the sulfur atom appearing in the formula, in which two Ar$^1$s, or Ar$^1$ and R$^2$ are simultaneously phenyl groups and the ring structure formed is a dibenzothiophene ring or a dibenzothiopyran ring;

wherein the arylsulfonium salt contains any of anion moieties of general formula (II):

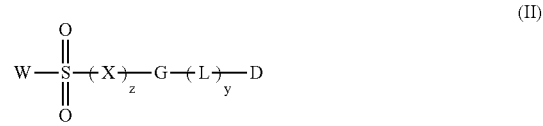

in which

X represents an optionally substituted alkylene group or an optionally substituted fluoroalkylene group, z being an integer of 0 or greater, G represents an alkylene group or arylene group optionally containing an ether oxygen, a group constituted of a combination thereof, or a single bond, L represents a bivalent connecting group, y being an integer of 0 or greater, D represents an optionally substituted organic group, and W represents any of groups of formulae:

$$\overset{-}{O}— \quad (III)$$

$$Rf—\overset{\overset{O}{\|}}{\underset{\underset{O}{\|}}{S}}—\overset{-}{N}— \quad (IV)$$

wherein Rf represents a fluoroalkyl group having at least one fluorine atom introduced therein as a substituent; and wherein in general formula (II), D represents any of groups of formula (V):

in which

Ar2 represents an aromatic ring, in which a substituent other than -(A-B) groups may further be introduced, p is an integer of 1 or greater, A represents a single bond or any one, or a combination of two or more members selected from among an alkylene group, —O—, —S—, —C(=O)—, —C(=O)O—, —S(=O)—, —S(=O)2-and —OS(=O)2-, B represents a group containing an aliphatic group having 3 or more carbon atoms, provided that when p is 2 or greater, a plurality of -(A-B) groups may be identical to or different from each other, and \* represents a site of connection to L of general formula (II).

\* \* \* \* \*